United States Patent
Ecker et al.

(10) Patent No.: US 9,447,462 B2
(45) Date of Patent: *Sep. 20, 2016

(54) METHODS FOR CONCURRENT IDENTIFICATION AND QUANTIFICATION OF AN UNKNOWN BIOAGENT

(71) Applicant: Ibis Biosciences, Inc., Carlsbad, CA (US)

(72) Inventors: David J. Ecker, Encinitas, CA (US); Rangarajan Sampath, San Diego, CA (US); Lawrence B. Blyn, Mission Viejo, CA (US); Steven A. Hofstadler, Vista, CA (US); Thomas A. Hall, Oceanside, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 247 days.

This patent is subject to a terminal disclaimer.

(21) Appl. No.: 14/164,559

(22) Filed: Jan. 27, 2014

(65) Prior Publication Data

US 2014/0141502 A1    May 22, 2014

Related U.S. Application Data

(63) Continuation of application No. 13/447,678, filed on Apr. 16, 2012, now abandoned, which is a continuation of application No. 12/684,742, filed on Jan. 8, 2010, now Pat. No. 8,187,814, which is a continuation of application No. 11/059,776, filed on Feb. 17, 2005, now Pat. No. 7,666,592.

(60) Provisional application No. 60/545,425, filed on Feb. 18, 2004, provisional application No. 60/559,754, filed on Apr. 5, 2004.

(51) Int. Cl.
*C12Q 1/68* (2006.01)
*C12P 19/34* (2006.01)
*C07H 21/04* (2006.01)

(52) U.S. Cl.
CPC .......... *C12Q 1/6851* (2013.01); *C12Q 1/6872* (2013.01); *C07H 21/04* (2013.01)

(58) Field of Classification Search
None
See application file for complete search history.

(56) References Cited

U.S. PATENT DOCUMENTS

| | | |
|---|---|---|
| 4,075,475 A | 2/1978 | Risby et al. |
| 4,683,195 A | 7/1987 | Mullis et al. |
| 4,965,188 A | 10/1990 | Mullis et al. |
| 4,683,202 B1 | 11/1990 | Mullis |
| 5,015,845 A | 5/1991 | Allen et al. |
| 5,072,115 A | 12/1991 | Zhou |
| 5,143,905 A | 9/1992 | Sivasubramanian et al. |
| 5,213,961 A | 5/1993 | Bunn et al. |
| 5,219,727 A | 6/1993 | Wang et al. |
| 5,288,611 A | 2/1994 | Kohne |
| 5,436,129 A | 7/1995 | Stapleton |
| 5,451,500 A | 9/1995 | Stapleton |
| 5,472,843 A | 12/1995 | Milliman |
| 5,476,774 A | 12/1995 | Wang et al. |
| 5,484,908 A | 1/1996 | Froehler et al. |
| 5,502,177 A | 3/1996 | Matteucci et al. |
| 5,503,980 A | 4/1996 | Cantor |
| 5,504,327 A | 4/1996 | Sproch et al. |
| 5,504,329 A | 4/1996 | Mann et al. |
| 5,523,217 A | 6/1996 | Lupski et al. |
| 5,527,669 A | 6/1996 | Resnick et al. |
| 5,527,675 A | 6/1996 | Coull et al. |
| 5,547,835 A | 8/1996 | Koster |
| 5,567,587 A | 10/1996 | Kohne |
| 5,576,204 A | 11/1996 | Blanco et al. |
| 5,580,733 A | 12/1996 | Levis et al. |
| 5,605,798 A | 2/1997 | Koester |
| 5,608,217 A | 3/1997 | Franzen et al. |
| 5,612,179 A | 3/1997 | Simons |
| 5,622,824 A | 4/1997 | Koster |
| 5,625,184 A | 4/1997 | Vestal et al. |
| 5,639,606 A | 6/1997 | Willey |
| 5,641,632 A | 6/1997 | Kohne |

(Continued)

FOREIGN PATENT DOCUMENTS

| | | |
|---|---|---|
| DE | 19732086 A1 | 1/1999 |
| DE | 19802905 A1 | 7/1999 |

(Continued)

OTHER PUBLICATIONS

Aaserud D.J., et al., "Accurate Base Composition of Double-Strand DNA by Mass Spectrometry," American Society for Mass Spectrometry, 1996, vol. 7 (12), pp. 1266-1269.

(Continued)

*Primary Examiner* — David Thomas
(74) *Attorney, Agent, or Firm* — David A. Casimir; Casimir Jones, S.C.

(57) ABSTRACT

The present invention provides methods for the quantification of an unknown bioagent in a sample by amplification of nucleic acid of the bioagent, and concurrent amplification of a known quantity of a calibration polynucleotide from which are obtained a bioagent identifying amplicon and a calibration amplicon. Upon molecular mass analysis, mass and abundance data are obtained. The identity of the bioagent is then determined from the molecular mass of the bioagent identifying amplicon and the quantity of the identified bioagent in the sample is determined from the abundance data of the bioagent identifying amplicon and the abundance data of the calibration amplicon.

20 Claims, 3 Drawing Sheets

(56) References Cited

U.S. PATENT DOCUMENTS

| | | |
|---|---|---|
| 5,645,985 A | 7/1997 | Froehler et al. |
| 5,683,869 A | 11/1997 | Ramsay Shaw et al. |
| 5,686,242 A | 11/1997 | Bruice et al. |
| 5,691,141 A | 11/1997 | Koster |
| 5,700,642 A | 12/1997 | Monforte et al. |
| 5,702,895 A | 12/1997 | Matsunaga et al. |
| 5,707,802 A | 1/1998 | Sandhu et al. |
| 5,712,125 A | 1/1998 | Uhlen |
| 5,716,825 A | 2/1998 | Hancock et al. |
| 5,727,202 A | 3/1998 | Kucala |
| 5,745,751 A | 4/1998 | Nelson et al. |
| 5,747,246 A | 5/1998 | Pannetier et al. |
| 5,747,251 A | 5/1998 | Carson et al. |
| 5,753,467 A | 5/1998 | Jensen et al. |
| 5,753,489 A | 5/1998 | Kistner et al. |
| 5,759,771 A | 6/1998 | Tilanus |
| 5,763,169 A | 6/1998 | Sandhu et al. |
| 5,763,588 A | 6/1998 | Matteucci et al. |
| 5,770,367 A | 6/1998 | Southern et al. |
| 5,777,324 A | 7/1998 | Hillenkamp |
| 5,814,442 A | 9/1998 | Natarajan et al. |
| 5,822,824 A | 10/1998 | Dion |
| 5,828,062 A | 10/1998 | Jarrell et al. |
| 5,830,653 A | 11/1998 | Froehler et al. |
| 5,830,655 A | 11/1998 | Monforte et al. |
| 5,830,853 A | 11/1998 | Backstrom et al. |
| 5,832,489 A | 11/1998 | Kucala |
| 5,834,255 A | 11/1998 | Van Gemen et al. |
| 5,845,174 A | 12/1998 | Yasui et al. |
| 5,849,492 A | 12/1998 | Rogan |
| 5,849,497 A | 12/1998 | Steinman |
| 5,849,901 A | 12/1998 | Mabilat et al. |
| 5,851,765 A | 12/1998 | Koster |
| 5,856,174 A | 1/1999 | Lipshutz et al. |
| 5,864,137 A | 1/1999 | Becker et al. |
| 5,866,429 A | 2/1999 | Bloch |
| 5,869,242 A | 2/1999 | Kamb |
| 5,871,697 A | 2/1999 | Rothberg et al. |
| 5,872,003 A | 2/1999 | Koster |
| 5,876,936 A | 3/1999 | Ju |
| 5,876,938 A | 3/1999 | Stolowitz et al. |
| 5,885,775 A | 3/1999 | Haff et al. |
| 5,900,481 A | 5/1999 | Lough et al. |
| 5,928,905 A | 7/1999 | Stemmer et al. |
| 5,928,906 A | 7/1999 | Koster et al. |
| 5,965,363 A | 10/1999 | Monforte et al. |
| 5,965,383 A | 10/1999 | Vogel et al. |
| 5,972,693 A | 10/1999 | Rothberg et al. |
| 5,976,798 A | 11/1999 | Parker et al. |
| 5,981,176 A | 11/1999 | Wallace |
| 5,981,190 A | 11/1999 | Israel |
| 5,994,066 A | 11/1999 | Bergeron et al. |
| 6,001,564 A | 12/1999 | Bergeron et al. |
| 6,005,096 A | 12/1999 | Matteucci et al. |
| 6,007,690 A | 12/1999 | Nelson et al. |
| 6,007,992 A | 12/1999 | Lin et al. |
| 6,015,666 A | 1/2000 | Springer et al. |
| 6,018,713 A | 1/2000 | Coli et al. |
| 6,024,925 A | 2/2000 | Little et al. |
| 6,028,183 A | 2/2000 | Lin et al. |
| 6,043,031 A | 3/2000 | Koester et al. |
| 6,046,005 A | 4/2000 | Ju et al. |
| 6,051,378 A | 4/2000 | Monforte et al. |
| 6,054,278 A | 4/2000 | Dodge et al. |
| 6,055,487 A | 4/2000 | Margery et al. |
| 6,060,246 A | 5/2000 | Summerton et al. |
| 6,061,686 A | 5/2000 | Gauvin et al. |
| 6,063,031 A | 5/2000 | Cundari et al. |
| 6,074,823 A | 6/2000 | Koster |
| 6,074,831 A | 6/2000 | Yakhini et al. |
| 6,090,558 A | 7/2000 | Butler et al. |
| 6,104,028 A | 8/2000 | Hunter et al. |
| 6,110,710 A | 8/2000 | Smith et al. |
| 6,111,251 A | 8/2000 | Hillenkamp |
| 6,133,436 A | 10/2000 | Koster et al. |
| 6,140,053 A | 10/2000 | Koster |
| 6,146,144 A | 11/2000 | Fowler et al. |
| 6,146,854 A | 11/2000 | Koster et al. |
| 6,153,389 A | 11/2000 | Haarer et al. |
| 6,159,681 A | 12/2000 | Zebala |
| 6,180,339 B1 | 1/2001 | Sandhu et al. |
| 6,180,372 B1 | 1/2001 | Franzen |
| 6,187,842 B1 | 2/2001 | Kobayashi et al. |
| 6,194,144 B1 | 2/2001 | Koster |
| 6,197,498 B1 | 3/2001 | Koster |
| 6,214,555 B1 | 4/2001 | Leushner et al. |
| 6,218,118 B1 | 4/2001 | Sampson et al. |
| 6,221,587 B1 | 4/2001 | Ecker et al. |
| 6,221,598 B1 | 4/2001 | Schumm et al. |
| 6,221,601 B1 | 4/2001 | Koster et al. |
| 6,221,605 B1 | 4/2001 | Koster |
| 6,225,450 B1 | 5/2001 | Koster |
| 6,235,476 B1 | 5/2001 | Bergmann et al. |
| 6,235,478 B1 | 5/2001 | Koster |
| 6,235,480 B1 | 5/2001 | Shultz et al. |
| 6,238,871 B1 | 5/2001 | Koster |
| 6,238,927 B1 | 5/2001 | Abrams et al. |
| 6,239,159 B1 | 5/2001 | Brown et al. |
| 6,258,538 B1 | 7/2001 | Koster et al. |
| 6,261,769 B1 | 7/2001 | Everett et al. |
| 6,265,716 B1 | 7/2001 | Hunter et al. |
| 6,265,718 B1 | 7/2001 | Park et al. |
| 6,266,131 B1 | 7/2001 | Hamada et al. |
| 6,266,144 B1 | 7/2001 | Li |
| 6,268,129 B1 | 7/2001 | Gut et al. |
| 6,268,131 B1 | 7/2001 | Kang et al. |
| 6,268,144 B1 | 7/2001 | Koster |
| 6,268,146 B1 | 7/2001 | Shultz et al. |
| 6,270,973 B1 | 8/2001 | Lewis et al. |
| 6,270,974 B1 | 8/2001 | Shultz et al. |
| 6,274,726 B1 | 8/2001 | Laugharn et al. |
| 6,277,573 B1 | 8/2001 | Koster |
| 6,277,578 B1 | 8/2001 | Shultz et al. |
| 6,277,634 B1 | 8/2001 | McCall et al. |
| 6,300,076 B1 | 10/2001 | Koster |
| 6,303,297 B1 | 10/2001 | Lincoln et al. |
| 6,312,893 B1 | 11/2001 | Van Ness et al. |
| 6,312,902 B1 | 11/2001 | Shultz et al. |
| 6,322,970 B1 | 11/2001 | Little et al. |
| 6,361,940 B1 | 3/2002 | Van Ness et al. |
| 6,372,424 B1 | 4/2002 | Brow et al. |
| 6,389,428 B1 | 5/2002 | Rigault et al. |
| 6,391,551 B1 | 5/2002 | Shultz et al. |
| 6,393,367 B1 | 5/2002 | Tang et al. |
| 6,419,932 B1 | 7/2002 | Dale |
| 6,423,966 B2 | 7/2002 | Hillenkamp et al. |
| 6,428,955 B1 | 8/2002 | Koster et al. |
| 6,428,956 B1 | 8/2002 | Crooke et al. |
| 6,432,651 B1 | 8/2002 | Hughes et al. |
| 6,436,635 B1 | 8/2002 | Fu et al. |
| 6,436,640 B1 | 8/2002 | Simmons et al. |
| 6,453,244 B1 | 9/2002 | Oefner |
| 6,458,533 B1 | 10/2002 | Felder et al. |
| 6,468,743 B1 | 10/2002 | Romick et al. |
| 6,468,748 B1 | 10/2002 | Monforte et al. |
| 6,475,143 B2 | 11/2002 | Iliff |
| 6,475,736 B1 | 11/2002 | Stanton |
| 6,475,738 B2 | 11/2002 | Shuber et al. |
| 6,479,239 B1 | 11/2002 | Anderson et al. |
| 6,500,621 B2 | 12/2002 | Koster |
| 6,553,317 B1 | 4/2003 | Lincoln et al. |
| 6,558,902 B1 | 5/2003 | Hillenkamp |
| 6,563,025 B1 | 5/2003 | Song et al. |
| 6,566,055 B1 | 5/2003 | Monforte et al. |
| 6,568,055 B1 | 5/2003 | Tang et al. |
| 6,582,916 B1 | 6/2003 | Schmidt et al. |
| 6,586,584 B2 | 7/2003 | McMillian et al. |
| 6,589,485 B2 | 7/2003 | Koster |
| 6,602,662 B1 | 8/2003 | Koster et al. |
| 6,605,433 B1 | 8/2003 | Fliss et al. |
| 6,610,492 B1 | 8/2003 | Stanton et al. |
| 6,613,509 B1 | 9/2003 | Chen |
| 6,613,520 B2 | 9/2003 | Ashby |
| 6,623,928 B2 | 9/2003 | Van Ness et al. |

(56) References Cited

U.S. PATENT DOCUMENTS

| | | | |
|---|---|---|---|
| 6,638,714 B1 | 10/2003 | Linnen et al. | |
| 6,680,476 B1 | 1/2004 | Hidalgo et al. | |
| 6,682,889 B1 | 1/2004 | Wang et al. | |
| 6,705,530 B2 | 3/2004 | Kiekhaefer | |
| 6,706,530 B2 | 3/2004 | Hillenkamp | |
| 6,783,939 B2 | 8/2004 | Olmsted et al. | |
| 6,800,289 B2 | 10/2004 | Nagata et al. | |
| 6,813,615 B1 | 11/2004 | Colasanti et al. | |
| 6,836,742 B2 | 12/2004 | Brekenfeld | |
| 6,852,487 B1 | 2/2005 | Barany et al. | |
| 6,856,914 B1 | 2/2005 | Pelech | |
| 6,875,593 B2 | 4/2005 | Froehler et al. | |
| 6,906,316 B2 | 6/2005 | Sugiyama et al. | |
| 6,906,319 B2 | 6/2005 | Hoyes | |
| 6,914,137 B2 | 7/2005 | Baker | |
| 6,977,148 B2 | 12/2005 | Dean et al. | |
| 6,994,962 B1 | 2/2006 | Thilly | |
| 7,022,835 B1 | 4/2006 | Rauth et al. | |
| 7,024,370 B2 | 4/2006 | Epler et al. | |
| 7,108,974 B2 | 9/2006 | Ecker et al. | |
| 7,198,893 B1 | 4/2007 | Köster et al. | |
| 7,217,510 B2 | 5/2007 | Ecker et al. | |
| 7,226,739 B2 | 6/2007 | Ecker et al. | |
| 7,255,992 B2 | 8/2007 | Ecker et al. | |
| 7,285,422 B1 | 10/2007 | Little et al. | |
| 7,312,036 B2 | 12/2007 | Sampath et al. | |
| 7,321,828 B2 | 1/2008 | Cowsert et al. | |
| 7,349,808 B1 | 3/2008 | Kreiswirth et al. | |
| 7,390,458 B2 | 6/2008 | Burow et al. | |
| 7,419,787 B2 | 9/2008 | Köster | |
| 7,501,251 B2 | 3/2009 | Köster et al. | |
| 7,666,588 B2 | 2/2010 | Ecker et al. | |
| 7,666,592 B2* | 2/2010 | Ecker | C12Q 1/6872 435/6.11 |
| 7,718,354 B2 | 5/2010 | Ecker et al. | |
| 7,741,036 B2 | 6/2010 | Ecker et al. | |
| 7,781,162 B2 | 8/2010 | Ecker et al. | |
| 8,187,814 B2* | 5/2012 | Ecker | C12Q 1/6872 435/6.12 |
| 2001/0039263 A1 | 11/2001 | Matthes et al. | |
| 2002/0006611 A1 | 1/2002 | Portugal et al. | |
| 2002/0042112 A1 | 4/2002 | Koster et al. | |
| 2002/0042506 A1 | 4/2002 | Kristyanne et al. | |
| 2002/0045178 A1 | 4/2002 | Cantor et al. | |
| 2002/0055101 A1 | 5/2002 | Bergeron et al. | |
| 2002/0120408 A1 | 8/2002 | Kreiswirth et al. | |
| 2002/0137057 A1 | 9/2002 | Wold et al. | |
| 2002/0138210 A1 | 9/2002 | Wilkes et al. | |
| 2002/0150927 A1 | 10/2002 | Matray et al. | |
| 2002/0168630 A1 | 11/2002 | Fleming et al. | |
| 2002/0187490 A1 | 12/2002 | Tiedje et al. | |
| 2003/0017487 A1 | 1/2003 | Xue et al. | |
| 2003/0027135 A1 | 2/2003 | Ecker et al. | |
| 2003/0039976 A1 | 2/2003 | Haff | |
| 2003/0050470 A1 | 3/2003 | An et al. | |
| 2003/0064483 A1 | 4/2003 | Shaw et al. | |
| 2003/0073112 A1 | 4/2003 | Zhang et al. | |
| 2003/0084483 A1 | 5/2003 | Simpson et al. | |
| 2003/0101172 A1 | 5/2003 | De La Huerga | |
| 2003/0104410 A1 | 6/2003 | Mittmann | |
| 2003/0104699 A1 | 6/2003 | Minamihaba et al. | |
| 2003/0113738 A1 | 6/2003 | Liu et al. | |
| 2003/0113745 A1 | 6/2003 | Monforte et al. | |
| 2003/0119018 A1 | 6/2003 | Omura et al. | |
| 2003/0129589 A1 | 7/2003 | Koster et al. | |
| 2003/0134312 A1 | 7/2003 | Burgoyne | |
| 2003/0143201 A1 | 7/2003 | Nagata et al. | |
| 2003/0148281 A1 | 8/2003 | Glucksmann | |
| 2003/0148284 A1 | 8/2003 | Vision et al. | |
| 2003/0167133 A1 | 9/2003 | Ecker et al. | |
| 2003/0167134 A1 | 9/2003 | Ecker et al. | |
| 2003/0175695 A1 | 9/2003 | Ecker et al. | |
| 2003/0175696 A1 | 9/2003 | Ecker et al. | |
| 2003/0175697 A1 | 9/2003 | Ecker et al. | |
| 2003/0175729 A1 | 9/2003 | Van Eijk et al. | |
| 2003/0186247 A1 | 10/2003 | Smarason et al. | |
| 2003/0187588 A1 | 10/2003 | Ecker et al. | |
| 2003/0187593 A1 | 10/2003 | Ecker et al. | |
| 2003/0190605 A1 | 10/2003 | Ecker et al. | |
| 2003/0190635 A1 | 10/2003 | McSwiggen | |
| 2003/0194699 A1 | 10/2003 | Lewis et al. | |
| 2003/0203398 A1 | 10/2003 | Bramucci et al. | |
| 2003/0220844 A1 | 11/2003 | Marnellos et al. | |
| 2003/0224377 A1 | 12/2003 | Wengel et al. | |
| 2003/0225529 A1 | 12/2003 | Ecker et al. | |
| 2003/0228571 A1 | 12/2003 | Ecker et al. | |
| 2003/0228597 A1 | 12/2003 | Cowsert et al. | |
| 2003/0228613 A1 | 12/2003 | Bornarth et al. | |
| 2004/0005555 A1 | 1/2004 | Rothman et al. | |
| 2004/0013703 A1 | 1/2004 | Ralph et al. | |
| 2004/0014957 A1 | 1/2004 | Eldrup et al. | |
| 2004/0023207 A1 | 2/2004 | Polansky | |
| 2004/0023209 A1 | 2/2004 | Jonasson | |
| 2004/0029129 A1 | 2/2004 | Wang et al. | |
| 2004/0038206 A1 | 2/2004 | Zhang et al. | |
| 2004/0038208 A1 | 2/2004 | Fisher et al. | |
| 2004/0038234 A1 | 2/2004 | Gut et al. | |
| 2004/0038385 A1 | 2/2004 | Langlois et al. | |
| 2004/0081993 A1 | 4/2004 | Cantor et al. | |
| 2004/0101809 A1 | 5/2004 | Weiss et al. | |
| 2004/0110169 A1 | 6/2004 | Ecker et al. | |
| 2004/0111221 A1 | 6/2004 | Beattie et al. | |
| 2004/0117129 A1 | 6/2004 | Ecker et al. | |
| 2004/0117354 A1 | 6/2004 | Azzaro et al. | |
| 2004/0121309 A1 | 6/2004 | Ecker et al. | |
| 2004/0121310 A1 | 6/2004 | Ecker et al. | |
| 2004/0121311 A1 | 6/2004 | Ecker et al. | |
| 2004/0121312 A1 | 6/2004 | Ecker et al. | |
| 2004/0121313 A1 | 6/2004 | Ecker et al. | |
| 2004/0121314 A1 | 6/2004 | Ecker et al. | |
| 2004/0121315 A1 | 6/2004 | Ecker et al. | |
| 2004/0121329 A1 | 6/2004 | Ecker et al. | |
| 2004/0121335 A1 | 6/2004 | Ecker et al. | |
| 2004/0121340 A1 | 6/2004 | Ecker et al. | |
| 2004/0122598 A1 | 6/2004 | Ecker et al. | |
| 2004/0122857 A1 | 6/2004 | Ecker et al. | |
| 2004/0126764 A1 | 7/2004 | Lasken et al. | |
| 2004/0137013 A1 | 7/2004 | Katinger et al. | |
| 2004/0185438 A1 | 9/2004 | Ecker | |
| 2004/0191769 A1 | 9/2004 | Marino et al. | |
| 2004/0202997 A1 | 10/2004 | Ecker et al. | |
| 2004/0253583 A1 | 12/2004 | Ecker et al. | |
| 2004/0253619 A1 | 12/2004 | Ecker et al. | |
| 2005/0026147 A1 | 2/2005 | Walker et al. | |
| 2005/0026641 A1 | 2/2005 | Hokao | |
| 2005/0027459 A1 | 2/2005 | Ecker et al. | |
| 2005/0065813 A1 | 3/2005 | Mishelevich et al. | |
| 2005/0130216 A1 | 6/2005 | Becker et al. | |
| 2005/0142584 A1 | 6/2005 | Willson et al. | |
| 2005/0250125 A1 | 11/2005 | Novakoff | |
| 2005/0266411 A1 | 12/2005 | Hofstadler et al. | |
| 2006/0020391 A1 | 1/2006 | Kreiswirth et al. | |
| 2006/0172330 A1 | 8/2006 | Osborn et al. | |
| 2006/0205040 A1 | 9/2006 | Sampath | |
| 2006/0240412 A1 | 10/2006 | Hall et al. | |
| 2006/0259249 A1 | 11/2006 | Sampath et al. | |
| 2008/0311558 A1 | 12/2008 | Ecker et al. | |
| 2009/0004643 A1 | 1/2009 | Ecker et al. | |
| 2009/0023150 A1 | 1/2009 | Koster et al. | |
| 2009/0042203 A1 | 2/2009 | Koster | |
| 2009/0092977 A1 | 4/2009 | Koster | |
| 2009/0182511 A1 | 7/2009 | Ecker et al. | |
| 2010/0145626 A1 | 6/2010 | Ecker et al. | |
| 2010/0184035 A1 | 7/2010 | Hall et al. | |

FOREIGN PATENT DOCUMENTS

| | | |
|---|---|---|
| DE | 19824280 A1 | 12/1999 |
| DE | 19852167 A1 | 5/2000 |
| DE | 19943374 A1 | 3/2001 |
| DE | 10132147 A1 | 2/2003 |
| EP | 281390 A2 | 9/1988 |
| EP | 633321 A1 | 1/1995 |
| EP | 620862 B1 | 4/1998 |

(56) References Cited

FOREIGN PATENT DOCUMENTS

| | | |
|---|---|---|
| EP | 1035219 A1 | 9/2000 |
| EP | 1138782 A2 | 10/2001 |
| EP | 1234888 A2 | 8/2002 |
| EP | 1308506 A1 | 5/2003 |
| EP | 1310571 A2 | 5/2003 |
| EP | 1333101 A1 | 8/2003 |
| EP | 1365031 A1 | 11/2003 |
| EP | 1234888 A3 | 1/2004 |
| EP | 1748072 A1 | 1/2007 |
| FR | 2811321 A1 | 1/2002 |
| GB | 2325002 A | 11/1998 |
| GB | 2339905 A | 2/2000 |
| JP | 5276999 A2 | 10/1993 |
| JP | 11137259 A | 5/1999 |
| JP | 24024206 A2 | 1/2004 |
| JP | 2004000200 A2 | 1/2004 |
| JP | 24201679 A2 | 7/2004 |
| JP | 2004201641 A | 7/2004 |
| WO | WO-8803957 A1 | 6/1988 |
| WO | WO-9015157 A1 | 12/1990 |
| WO | WO-9205182 A1 | 4/1992 |
| WO | WO-9208117 A1 | 5/1992 |
| WO | WO-9209703 A1 | 6/1992 |
| WO | WO-9219774 A1 | 11/1992 |
| WO | WO-9303186 A1 | 2/1993 |
| WO | WO-9305182 A1 | 3/1993 |
| WO | WO-9308297 A1 | 4/1993 |
| WO | WO-9416101 A2 | 7/1994 |
| WO | WO-9419490 A1 | 9/1994 |
| WO | WO-9421822 A1 | 9/1994 |
| WO | WO-9504161 A1 | 2/1995 |
| WO | WO-9511996 A1 | 5/1995 |
| WO | WO-9513395 A1 | 5/1995 |
| WO | WO-9513396 A2 | 5/1995 |
| WO | WO-9531997 A1 | 11/1995 |
| WO | WO-9606187 A1 | 2/1996 |
| WO | WO-9616186 A1 | 5/1996 |
| WO | WO-9629431 A2 | 9/1996 |
| WO | WO-9632504 A2 | 10/1996 |
| WO | WO-9635450 A1 | 11/1996 |
| WO | WO-9637630 A1 | 11/1996 |
| WO | WO-9733000 A1 | 9/1997 |
| WO | WO-9734909 A1 | 9/1997 |
| WO | WO-9737041 A2 | 10/1997 |
| WO | WO-9747766 A1 | 12/1997 |
| WO | WO-9803684 A1 | 1/1998 |
| WO | WO-9812355 A1 | 3/1998 |
| WO | WO-9814616 A1 | 4/1998 |
| WO | WO-9815652 A1 | 4/1998 |
| WO | WO-9820020 A2 | 5/1998 |
| WO | WO-9820157 A2 | 5/1998 |
| WO | WO-9820166 A2 | 5/1998 |
| WO | WO-9826095 A1 | 6/1998 |
| WO | WO-9831830 A1 | 7/1998 |
| WO | WO-9835057 A1 | 8/1998 |
| WO | WO-9840520 A1 | 9/1998 |
| WO | WO-9854571 A1 | 12/1998 |
| WO | WO-9854751 A1 | 12/1998 |
| WO | WO-9905319 A2 | 2/1999 |
| WO | WO-9912040 A2 | 3/1999 |
| WO | WO-9913104 A1 | 3/1999 |
| WO | WO-9914375 A2 | 3/1999 |
| WO | WO-9929898 A2 | 6/1999 |
| WO | WO-9931278 A1 | 6/1999 |
| WO | WO-9957318 A2 | 11/1999 |
| WO | WO-9958713 A2 | 11/1999 |
| WO | WO-9960183 A1 | 11/1999 |
| WO | WO-0032750 A1 | 6/2000 |
| WO | WO-0038636 A1 | 7/2000 |
| WO | WO-0063362 A1 | 10/2000 |
| WO | WO-0066762 A2 | 11/2000 |
| WO | WO-0066789 A2 | 11/2000 |
| WO | WO-0077260 A1 | 12/2000 |
| WO | WO-0100828 A2 | 1/2001 |
| WO | WO-0107648 A1 | 2/2001 |
| WO | WO-0112853 A1 | 2/2001 |
| WO | WO-0120018 A2 | 3/2001 |
| WO | WO-0123604 A2 | 4/2001 |
| WO | WO-0123608 A2 | 4/2001 |
| WO | WO-0132930 A1 | 5/2001 |
| WO | WO-0140497 A2 | 6/2001 |
| WO | WO-0146404 A1 | 6/2001 |
| WO | WO-0151661 A2 | 7/2001 |
| WO | WO-0151662 A1 | 7/2001 |
| WO | WO-0157263 A1 | 8/2001 |
| WO | WO-0157518 A2 | 8/2001 |
| WO | WO-0173119 A2 | 10/2001 |
| WO | WO-0173199 A1 | 10/2001 |
| WO | WO-0177392 A2 | 10/2001 |
| WO | WO-0196388 A2 | 12/2001 |
| WO | WO-0202811 A2 | 1/2002 |
| WO | WO-0210186 A1 | 2/2002 |
| WO | WO-0210444 A1 | 2/2002 |
| WO | WO-0218641 A2 | 3/2002 |
| WO | WO-0221108 A2 | 3/2002 |
| WO | WO-0222873 A1 | 3/2002 |
| WO | WO-0224876 A2 | 3/2002 |
| WO | WO-0250307 A1 | 6/2002 |
| WO | WO-02057491 A2 | 7/2002 |
| WO | WO-02070664 A2 | 9/2002 |
| WO | WO-02070728 A2 | 9/2002 |
| WO | WO-02070737 A2 | 9/2002 |
| WO | WO-02077278 A1 | 10/2002 |
| WO | WO-02099034 A2 | 12/2002 |
| WO | WO-02099095 A2 | 12/2002 |
| WO | WO-02099129 A2 | 12/2002 |
| WO | WO-02099130 A2 | 12/2002 |
| WO | WO-03001976 A2 | 1/2003 |
| WO | WO-03002750 A2 | 1/2003 |
| WO | WO-03008636 A2 | 1/2003 |
| WO | WO-03012058 A2 | 2/2003 |
| WO | WO-03012074 A2 | 2/2003 |
| WO | WO-03014382 A2 | 2/2003 |
| WO | WO-03016546 A1 | 2/2003 |
| WO | WO-03018636 A2 | 3/2003 |
| WO | WO-03020890 A2 | 3/2003 |
| WO | WO-03033732 A2 | 4/2003 |
| WO | WO-03054162 A2 | 7/2003 |
| WO | WO-03054755 A2 | 7/2003 |
| WO | WO-03060163 A2 | 7/2003 |
| WO | WO-03075955 A1 | 9/2003 |
| WO | WO-03088979 A2 | 10/2003 |
| WO | WO-03093506 A2 | 11/2003 |
| WO | WO-03097869 A2 | 11/2003 |
| WO | WO-03100035 A2 | 12/2003 |
| WO | WO-03100068 A1 | 12/2003 |
| WO | WO-03102191 A1 | 12/2003 |
| WO | WO-03104410 A2 | 12/2003 |
| WO | WO-03106635 A2 | 12/2003 |
| WO | WO-2004003511 A2 | 1/2004 |
| WO | WO-2004009849 A1 | 1/2004 |
| WO | WO-2004011651 A2 | 2/2004 |
| WO | WO-2004013357 A2 | 2/2004 |
| WO | WO-2004040013 A1 | 5/2004 |
| WO | WO-2004044123 A2 | 5/2004 |
| WO | WO-2004044247 A2 | 5/2004 |
| WO | WO-2004052175 A2 | 6/2004 |
| WO | WO-2004053076 A2 | 6/2004 |
| WO | WO-2004053141 A2 | 6/2004 |
| WO | WO-2004053164 A1 | 6/2004 |
| WO | WO-2004060278 A2 | 7/2004 |
| WO | WO-2004070001 A2 | 8/2004 |
| WO | WO-2004072230 A2 | 8/2004 |
| WO | WO-2004072231 A2 | 8/2004 |
| WO | WO-2004101809 A2 | 11/2004 |
| WO | WO-2005003384 A1 | 1/2005 |
| WO | WO-2005009202 A2 | 2/2005 |
| WO | WO-2005012572 A1 | 2/2005 |
| WO | WO-2005024046 A2 | 3/2005 |
| WO | WO-2005036369 A2 | 4/2005 |
| WO | WO-2005054454 A1 | 6/2005 |
| WO | WO-2005075686 A1 | 8/2005 |
| WO | WO-2005086634 A2 | 9/2005 |
| WO | WO-2005091971 A2 | 10/2005 |

(56) References Cited

FOREIGN PATENT DOCUMENTS

| WO | WO-2005098047 A2 | 10/2005 |
|---|---|---|
| WO | WO-2005116263 A2 | 12/2005 |
| WO | WO-2006089762 A1 | 8/2006 |
| WO | WO-2006094238 A2 | 9/2006 |
| WO | WO-2006116127 A2 | 11/2006 |
| WO | WO-2006135400 A2 | 12/2006 |
| WO | WO-2007014045 A2 | 2/2007 |
| WO | WO-2007086904 A2 | 8/2007 |
| WO | WO-2008104002 A2 | 8/2008 |
| WO | WO-2008118809 A1 | 10/2008 |

OTHER PUBLICATIONS

Aaserud D.J., et al., "DNA Sequencing with Blackbody Infrared Radioactive Dissociation of Electrosprayed Ions," International Journal of Mass Spectrometry and Icon Processes, 1997, vol. 167/168, pp. 705-712.
Adam E., et al., "Characterization of Intertype Specific Epitopes on Adenovirus Hexons," Archives of Virology, 1998, vol. 143 (9), pp. 1669-1682.
Adam E., et al., "Intertype Specific Epitope Structure of Adenovirus Hexon," Acta Microbiologica et Immunologica Hungarica, 1998, vol. 45 (3-4), pp. 311-316.
Adam E., et al., "Molecular Structure of the Two-Dimensional Hexon Crystalline Array and of Adenovirus Capsid," Acta Microbiologica et Immunologica Hungarica, 1998, vol. 45 (3-4), pp. 305-310.
Adrian T., et al., "DNA Restriction Analysis of Adenovirus Prototypes 1 to 41," Archives of Virology, 1986, vol. 91 (3-4), pp. 277-290.
Adzhar A., et al., "Universal Oligonucleotides for the Detection of Infectious Bronchitis Virus by Thepolymerase Chain Reaction," Avian Pathology, 1996, vol. 25 (4), pp. 817-836.
Agostini H.T., et al., "Complete Genome of a JC Virus Genotype Type 6 from the Brain of an African American with Progressive Multifocal Leukoencephalopathy," Journal of Human Virology, 1998, vol. 1 (4), pp. 267-272.
Aires De Sousa M., et al., "Bridges from Hospitals to the Laboratory: Genetic Portraits of Methicillin-Resistant *Staphylococcus aureus* Clones," FEMS Immunology and Medical Microbiology, 2004, vol. 40 (2), pp. 101-111.
Akalu A., et al., "Rapid Identification of Subgenera of Human Adenovirus by Serological and PCR Assays," Journal of Virological Methods, 1998, vol. 71 (2), pp. 187-196.
Alba M.M., et al., "VIDA: A Virus Database System for the Organization of Animal Virus Genome Open Reading Frames," Nucleic Acids Research, 2001, vol. 29 (1), pp. 133-136.
Allaouchiche B., et al., "Clinical Impact of Rapid Oxacillin Susceptibility Testing Using a PCR Assay in *Staphylococcus aureus* Bactaeremia," The Journal of Infection, 1999, vol. 39 (3), pp. 198-204.
Allawi H.T., et al., "Thermodynamics and NMR of Internal G.T. Mismatches in DNA," Biochemistry, 1997, vol. 36 (34), pp. 10581-10594.
Altschuel S.F., et al., "Basic Local Alignment Search Tool," Journal of Molecular Biology, 1990, vol. 215 (3), pp. 403-410.
Altschul S.F., et al., "Gapped BLAST and PSI-BLAST: A New Generation of Protein Database Search Programs," Nucleic Acids Research, 1997, 25 (17), 3389-3402.
Alves-Silva J., et al., "The Ancestry of Brazilian mtDNA Linages," The American Journal of Human Genetics, 2000, vol. 67 (2), pp. 444-461.
Amano Y., et al., "Detection of Influenza Virus: Traditional Approaches and Development of Biosensors," Analytical and Bioanalytical Chemistry, 2005, vol. 381 (1), pp. 156-164.
Amexis G., et al., "Quantitative Mutant Analysis of Viral Quasispecies by Chip-Based Matrix Assisted LaserDesorption Ionization Time-of-Flight Mass Spectrometry," Proceedings of the National Academy of Sciences, 2001, vol. 98 (21), pp. 12097-12102.
Anderson M.L.M., "Quantitative Filter Hybridization" in: Nucleic Acid Hybridization, Hames B.D., ed., IRL Press, 1985, pp. 73-111.
Anderson S., et al., "Sequence and Organization of the Human Mitochondrial Genome," Nature, 1981, vol. 290 (5806), pp. 457-465.
Andreasson H., et al., "Mitochondrial Sequence Analysis for Forensic Identification Using Pyrosequencing Technology," BioTechniques, 2002, vol. 32 (1), pp. 124-133.
Anthony R.M., et al., "Use of the Polymerase Chain Reaction for Rapid Detection of High-Level Mupirocin Resistance in *Staphylococci*," European Journal of Clinical Microbiology & Infectious Diseases, 1999, vol. 18 (1), pp. 30-34.
Arbique J., et al., "Comparison of the Velogene Rapid MRSA Identification Assay, Denka MRSAScreen Assay, and BBL Crystal MRSA ID System for Rapid Identification of Methicillin-Resistant *Staphylococcus aureus*," Diagnositic Microbiology and Infectious Diseases, 2001, vol. 40 (1-2), pp. 5-10.
Archer G.L., et al., "Detection of Methicillin Resistance in *Staphylococci* by Using a DNA Probe," Antimicrobial Agents and Chemotherapy, 1990, vol. 34 (9), pp. 1720-1724.
Armstrong P., et al., "Sensitive and Specific Colorimetric Dot Assay to Detect Eastern Equine Encephalomyelitis Viral RNA in Mosquitoes After PCR Amplification," Journal of Medicinal Entomology, 1995, vol. 32 (1), pp. 42-52.
Arnal C., et al., "Quantification of Hepatitis A Virus in Shellfish by Competitive Reverse Transcription PCR with Coextraction of Standard RNA," Applied and Environmental Microbiology, 1999, vol. 65 (1), pp. 322-326.
Aronsson F., et al., "Persistence of the Influenza A/WSN/33 Virus RNA at Midbrain Levels of Immunodefective Mice," Journal of Neurovirology, 2001, vol. 7 (2), pp. 117-124.
Ausubel F.M., et al., Eds., Current Protocols in Molecular Biology, vol. 1, John Wiley & Sons Inc., 2004, Table of Contents.
Ausubel F.M., et al., eds., Short Protocols in Molecular Biology: A Compendium of Methods from Current Protocols in Molecular Biology, 2nd Edition, John Wiley & Sons, 1992, Units 2.9, 3.4-3.17, 4.6-4.10, and 10.8.
Ausubel F.M., et al., "Unit 2.11 "Synthesis and Purification of Oligonucleotides," in: Current Protocols in Molecular Biology," 1998, John Wiley & Sons, Inc., pp. 2.11-2.11.21.
Avellon A., et al., "Rapid and Sensitive Diagnosis of Human Adenovirus Infections by a Generic Polymerase Chain Reaction," Journal of Virological Methods, 2001, vol. 92 (2), pp. 113-120.
Azevedo A.M., et al., "Detection of Influenza, Parainfluenza, Adenovirus and Respiratory Syncytial Virus during Asthma Attacks in Children Older than 2 Years Old," Allergologia Immunopathologia, 2003, vol. 31 (6), pp. 311-317.
Baba T., et al., "Genome and Virulence Determinants of High Virulence Community-Acquired MRSA," Lancet, 2002, vol. 359 (9320), pp. 1819-1827.
Bahrmahd A.R., et al., "Polymerise Chain Reaction of Bacterial Genomes with Single Universal Primer: Application to Distinguishing Mycobacteria Species," Molecular and Cellular Probes, 1996, vol. 10 (2), pp. 117-122.
Bahrmahd A.R., et al., "Use of Restriction Enzyme Analysis of Amplified DNA Coding for the hsp65 Gene and Polymerase Chain Reaction with Universal Primer for Rapid Differtiation of Mycobacterium Species in the Clinical Laboratory," Scandinavian Journal of Infectious Diseases, 1998, vol. 30 (5), pp. 477-480.
Bai J., et al., "Matrix-Assisted Laser Desorption/Ionization Mass Spectrometry of Restriction Enzyme-Digested Plasmid DNA Using an Active Nafion Substrate," Rapid Communications in Mass Spectrometry, 1994, vol. 8 (9), pp. 687-691.
Baker G.C., et al., "Review and Re-Analysis of Domain-Specific 16S Primers," Journal of Microbiological Methods, 2003, vol. 55 (3), pp. 541-555.
Banik U., et al., "Multiplex PCR Assay for Rapid Identification of Oculopathogenic Adenoviruses by Amplification of the Fiber and Hexon Genes," Journal of Clincal Microbiology, 2005, vol. 43 (3), pp. 1064-1068.
Barbour A.G., et al., "Identification of an Uncultivatable *Borrelia* Species in the Hard Tick Amblyomma Americanum: Possible Agent of a Lyme Disease-Like Illness," The Journal of Infectious Diseases, 1996, vol. 173 (2), pp. 403-409.

(56) References Cited

OTHER PUBLICATIONS

Barns S.M., et al., "Detection of Diverse New Francisella-like Bacteria in Environmental Samples," Applied and Environmental Microbiology, 2005, vol. 71 (9), pp. 5494-5500.
Baron E.J., "Genetic Aspects of Methicillin Resistance in *Staphylococcus aureus* and MethodsUsed for its Detection in Clinical Laboratories in the United States," Journal of Chemotherapy, 1995, vol. 7 (Suppl. 3), pp. 87-92.
Barr I.G., et al., "An Influenza A(H3) Reassortant was Epidemic in Australia and New Zealand in 2003," Journal of Medical Virology, 2005, vol. 76 (3), pp. 391-397.
Barski P., et al., "Rapid Assay for Detection of Methicillin-Resistant *Staphylococcus aureus* Using Multiplex PCR," Molecular and Cellular Probes, 1996, vol. 10 (6), pp. 471-475.
Bastia T., et al., "Organelle DNA Analysis of Solanum and Brassica Somatic Hybrids by PCR with Universal Primers," Theoretical and Applied Genetics, 2001, vol. 102 (8), pp. 1265-1272.
Batey R.T., et al., "Preparation of Isotopically Labeled Ribonucleotides for Multidimensional NMR Spectroscopy of RNA," Nucleic Acids Research, 1992, vol. 20 (17), pp. 4515-4523.
Baumer A., et al., "Age-Related Human mtDNA Deletions: A Heterogeneous Set of Deletions Arising at aSingle Pair of Directly Repeated Sequences," American Journal of Human Jenetics, 1994, vol. 54 (4), pp. 618-630.
Beall B., et al., "Sequencing emm-Specific PCR Products for Routine andAccurate Typing of Group A *Streptococci*," Journal of Clincal Microbiology, 1996, vol. 34 (4), pp. 953-958.
Beall B., et al., "Survey of emm Gene Sequences and T-Antigen Types from Systemic *Streptococcus pyogenes* Infection Isolates Collected in San Francisco, California; Atlanta, Georgia; and Connecticut in 1994 and 1995," Journal of Clincal Microbiology, 1997, vol. 35 (5), pp. 1231-1235.
Benko, M. et al., "Family Adenoviridae," Virus taxonomy. VIIIth report of the International Committee on Taxonomy of Viruses, 2004, Academic Press, New York, pp. 213-228.
Benson D.A., et al., "GenBank," Nucleic Acids Research, 1999, vol. 27 (1), pp. 12-17.
Benson L.M., et al, "Advantages of Thermococcus Kodakaraenis (KOD) DNA Polymerase for PCR-Mass Spectrometry Based Analyses," American Society for Mass Spectrometry, 2003, vol. 14 (6), pp. 601-604.
Berencsi G., et al., "Molecular Biological Characterization of Adenovirus DNA," Acta Microbiologica et Immunologica Hungarica, 1998, vol. 45 (3-4), pp. 297-304.
Bishop M.J., et al., "Molecular Sequence Databases" in: Nucleic Acid and Protein Sequence Analysis, 4th Chapter, Bishop M.J., et al., Eds, IRL Press, 1987, pp. 83-113.
Bisno A.L., "*Streptococcus pyogenes* " in: Infectious Diseases and Their Etiologic Agents, vol. 2, Mandell, Eds., Churchill Livingston, New York, 1995, pp. 1786-1799.
Black R.M., et al., "Detection of Trace Levels of Tricothecene Mycotoxins in Human Urineby Gas Chromatography-Mass Spectrometry," Journal of Chromatography, 1986, vol. 367 (1), pp. 103-115.
Blaiotta G., et al., "PCR Detection of *Staphylococcal enterotoxin* Genes in *Staphyiococcus* Spp. Strains Isolated from Meat and Dairy Products. Evidence for New Variants of seG and Sel in *S. aureus* AB-8802," Journal of Applied Microbiology, 2004, vol. 97 (4), pp. 719-730.
BLAST Search results, Mar. 7, 2006.
Boivin-Jahns V., et al., "Bacterial Diversity in a Deep-Subsurface Clay Environment," Applied and Environmental Microbiology, 1996, vol. 62 (9), pp. 3405-3412.
Bolton E.T., et al., "A General Method for the Isolation of RNA Complementary to DNA," Proceedings of the National Academy of Sciences, 1962, vol. 48, pp. 1390-1397.
Bonk T., et al., "Matrix-Assisted Laser Desorption/Ionization Time-of-Flight Mass Spectrometry-Based Detection of Microsatellite Instabilities in Coding DNA Sequences: A Novel Approach to Identify DNA-Mismatch Repair-Deficient Cancer Cells," Clinical Chemistry, 2003, vol. 49 (4), pp. 552-561.
Borrow R., et al., "SiaD PCR Elisa for Confirmation and Identification of Serogroup Y and W135 Meningococcal Infections," FEMS Microbiology Letters, 1998, vol. 159 (2), pp. 209-214.
Boubaker K., et al., "Panton-Valentine Leukocidin and *Staphylococcal* Skin Infections in Schoolchildren," Emerging Infectious Diseases, 2004, vol. 10 (1), pp. 121-124.
Bowen J.E., et al., "The Native Virulence Plasmid Combination Affects the Segregational Stability of a Thetareplicating Shuttle Vector in *Bacillus anthracis* Var," Journal of Applied Microbiology, 1999, vol. 87 (2), pp. 270-278.
Bowers K.M., et al., "Screening for Methicillin Resistance in *Staphylococars aureus* and Coagulasenegative *Staphylococci*: Evaluation of Three Selective and Mastalex-MRSA latex Agglutination," British Journal of Biomedical Science, 2003, vol. 60 (2), pp. 71-74.
Brakstad O.G., et al., "Direct Identification of *Staphylococcus aureus* in Blood Cultures Bydetection of the Gene, Encoding the Thermostable Nuclease or the Gene Product," Acta Pathologica, Microbiologica et Immunologica Scandinavica, 1995, vol. 103 (3), pp. 209-218.
Brakstad O.G., et al., "Multiplex Polymerase Chain Reaction for Detection of Genes for *Staphylococcus aureus* Themonuclease and Methicillin Resistance and Correlation with Oxacillin Resistance," Acta Pathologica, Microbiologica et Immunologica Scandinavica, 1993, vol. 101 (9), pp. 681-688.
Brandt C.D., et al., "Infections in 18,000 Infants and Children in a Controlled Study of Respiratory Tract Disease. I. Adenovirus Pathogenicity in Relation to Serologic Type and Illness Syndrome," American Journal of Epidemiology, 1969, vol. 90 (6), pp. 484-500.
Brayshaw D.P., "Methicillin-Resistant *Staphylococcus aureus* : Evaluation of Detection Techniques on Laboratory-Passaged Organisms," British Journal of Biomedical Science, 1999, vol. 56 (3), pp. 170-176.
Brightwell G., et al., "Development of Internal Controls for PCR Detection of Bacillus Anthracis," Molecular and Cellular Probes, 1998, vol. 12 (6), pp. 367-377.
Brightwell G., et al., "Genetic Targets for the Detection and Identifiaction of Venezuelan Equine Encephalitis Viruses," Archives of Virology, 1998, vol. 143 (4), pp. 731-742.
Bronzoni R.V.M., et al., "Duplex Reverse Transcription-PCR Followed by Nested PCR Assays for Detection and Identification of Brazilian Alphaviruses and Flaviviruses," Journal of Clincal Microbiology, 2005, vol. 43 (2), pp. 696-702.
Bronzoni R.V.M., et al., "Multiplex Nested PCR for Brazilian Alphavirus Diagnosis," Transactions of the Royal Society of Tropical Medicine and Hygiene, 2004, vol. 98 (8), pp. 456-461.
Brown I.H., "Advances in Molecular Diagnostics for Avian Influenza," Developments in Biologicals, 2006, vol. 124, pp. 93-97.
Brownstein M.J., et al., "Modulation of Non-Templated Nucleotide Addition by Taq DNA Polymerase: Primer Modifications that Facilitate Genotyping," BioTechniques, 1996, vol. 20 (6), pp. 1004-1010.
Brunaud V., et al., "T-DNA Integration into the Arabidopsis Genome Depends on Sequence of Pre-Insertion Sites," EMBO Reports, 2002, vol. 3 (12), pp. 1152-1157.
Buck G.A., et al., "Design Strategies and Performance of Custom DNA Sequencing Primers," BioTechniques, 1999, vol. 27 (3), pp. 528-536.
Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.
Butel J.S., et al., "Cell and Molecular Biology of Simian Virus 40: Implications for Human Infections and Disease," Journal of the National Cancer Institute, 1999, vol. 91 (2), pp. 119-134.
Butler J., "DNA Profiling and Quantitation of Human DNA," CCQM Bio Analysis Working Group, 2005.

(56) References Cited

OTHER PUBLICATIONS

Butler J.M., et al., High Throughput Genotyping of Forensic STRs and SNPs using Time-of-Flight Mass Spectrometry, 9th International Symposium on Human Identification, 1998, Orlando FL.

Campbell W.P., et al., "Detection of California Serogroup Bunyavirus in Tissue Culture and Mosquito Pools by PCR," Journal of Virological Methods, 1996, vol. 57 (2), pp. 175-179.

Carracedo A., et al., "DNA Commission of the International Society for Forensic Genetics: Guidelines Formitochondrial DNA Typing," Forensic Science International, 2000, vol. 110 (2), pp. 79-85.

Carroll K.C., et al., "Rapid Detection of the Staphylococcal mecA Gene from BACTEC BloodCulture Bottles by the Polymerase Chain Reaction," American Journal of Clincal Pathology, 1996, vol. 106 (5), pp. 600-605.

Case J.T., et al., "Maternal Inheritance of Mitochondrial DNA Polymorphisms in Cultured Human Fibroblasts," Somatic Cell Genetics, 1981, vol. 7 (1), pp. 103-108.

Cattoli G., et al., "Comparison of Three Rapid Detection Systems for Type A Influenza Virus on Tracheal Swabs of Experimentally and Naturally Infected Birds," Avian Pathology, 2004, vol. 33 (4), pp. 432-437.

Cavassini M., et al., "Evaluation of MRSA-Screen, a Simple Anti-PBP 2a Slide Latex AgglutinationKit, for Rapid Detection of Methicillin Resistance in *Staphylococcus aureus*," Journal of Clinical Microbiology, 1999, vol. 37 (5), pp. 1591-1594.

Certificate of Correction mailed Jan. 6 2009 for U.S. Appl. No. 10/660,996, filed Sep. 12, 2003.

Certificate of Correction mailed Aug. 7, 2007 for U.S. Appl. No. 10/660,997, filed Sep. 12, 2003.

Certificate of Correction mailed Dec. 12, 2006 for U.S. Appl. No. 10/156,608, filed May 24, 2002.

Certificate of Correction mailed Jul. 17, 2007 for U.S. Appl. No. 09/891,793, filed Jun. 26, 2001.

Certificate of Correction mailed Mar. 31, 2008 for U.S. Appl. No. 09/891,793, filed Jun. 26, 2001.

Certificate of Correction mailed Mar. 31, 2008 for U.S. Appl. No. 10/156,608, filed May 24, 2002.

Certificate of Correction mailed Mar. 31, 2008 for U.S. Appl. No. 10/660,997, filed Sep. 12, 2003.

Cespedes A., et al., "Polymerase Chain Reaction-Restriction Fragment Length Polymorphism Analysis of a Short Fragment of the Cytochrome b Gene for Identification of Flatfish Species," Journal of Food Protection, 1998, vol. 61 (12), pp. 1684-1685.

Chamberlin M., et al., "New RNA Polymerase from *Escerichia coli* Infected with Bacteriophage T7," Nature, 1970, vol. 228 (5268), pp. 227-231.

Chandra S., et al., "Virus Reduction in the Preparation and Intravenous Globulin: In Vitro Experiments," Transfusion, 1999, vol. 39 (3), pp. 249-257.

Chang P.K., et al., "aflT, a MFS Transporter-Encoding Gene Located in the Aflatoxin Gene Cluster, does not have a Significant Role in Aflatoxin Secretion," Fungal Genetics and Biology, 2004, vol. 41 (10), pp. 911-920.

Chaves F., et al., "Molecular Characterization of Resistance to Mupirocin in Methicillin-Susceptible and -Resistant Isolates of *Staphylococcus aureus* from Nasal Samples," Journal of Clincal Microbiology, 2004, vol. 42 (2), pp. 822-824.

Chelly J., et al., "Transcription of the Dystrophin Gene in Human Muscle and Non-Muscle Tissue," Nature, 1988, vol. 333 (6176), pp. 858-860.

Chen C.A., et al., "Universal Primers for Amplification of Mitochondrial Small Subunit Ribosomal RNA-Encoding Gene in Scleractinian Corals," Marine Biotechnology, 2000, vol. 2 (2), pp. 146-153.

Chen C.H., et al., Laser Desorption Mass Spectrometry for FastDNA Sequencing [online], Nov. 1994, Retrieved from the Internet<URL:http://www.ornl.gove/sci/techresources/Human_Genome/publicat/94SANTA/sequencing/seqtoc.shtml>.

Chen J., et al., "A Universal PCR Primer to Detect Members of the Potyviridae and its Use to Examine the Taxonomic Status of Several Members of the Family," Archives of Virology, 2001, vol. 146 (4), pp. 757-766.

Chen N., et al., "The Genomic Sequence of Ectromelia Virus, the Causative Agent of Mousepox," Virology, 2003, vol. 317 (1), pp. 165-186.

Chen R., et al., "Trapping, Detection, and Charge and Mass Measurement of Large Individual Ions (up to 1.1 X 108 Daltons) by Electrospray Ionization FTICR MS," 42nd ASMS Conference on Mass Spectrometry, 1994.

Chen Y.Z., et al., "A BAC-Based STS-Content Map Spanning a 35-Mb Region of Human Chromosome 1p35-36," Genomics, 2001, vol. 74 (1), pp. 55-70.

Chen Z., et al., "Genetic Mapping of the Cold-Adapted Phenotype of B/Ann Arbor/1/66, the Master Donor Virus for Live Attenuated Influenza Vaccines (FluMist)," Virology, 2006, vol. 345 (2), pp. 416-423.

Chiu N. H., et al., "Mass Spectrometry of Single-Stranded Restriction Fragments Captured by an Undigested Complementary Sequence," Nucleic Acids Research, 2000, vol. 28 (8), pp. E31.

Chmielewicz B., et al., "Development of a PCR-Based Assay for Detection, Quantification, and Genotyping of Human Adenoviruses," Clinical Chemistry, 2005, vol. 51 (8), pp. 1365-1373.

Cho M., et al., "Application of the Ribonuclease P (RNaseP) RNA Gene Sequence for Phylogenetic Analysis of the Genus *Saccharomonospora*," International Journal of Systematic Bacteriology, 1998, vol. 48 (4), pp. 1223-1230.

Choi S., et al., "Real-Time PCR Quantification of Human Adenoviruses in Urban Rivers Indicates Genome Prevalence but Low Infectivity," Applied and Environmental Microbiology, 2005, vol. 71 (11), pp. 7426-7433.

Choi Y.K., et al., "Detection and Subtying of Swine Influenza H1N1, H1 N2 and H3N2 Viruses in Clinical Samples Using Two Multiplex RT-PCR Assays," Journal of Virological Methods, 2002, vol. 102 (1-2), pp. 53-59.

Christel L.A., et al., "Rapid, Automated Nucleic Acid Probe Assays Using Silicon Microstructures for Nucleic Acid Concentration," Journal of Biomechanical Engineering, 1999, vol. 121 (1), pp. 22-27.

Claas E.C., et al., "Internally Controlled Real-Time PCT Monitoring of Adenovirus DNA Load inSerum or Plasma of Transplant Recipients," Journal of Clincal Microbiology, 2005, vol. 43 (4), pp. 1738-1744.

Cloney L., et al., "Rapid Detection of mecA in Methicillin Resistant *Staphylococcus aureus* Using Cycling Probe Technology," Molecular and Cellular Probes, 1999, vol. 13 (13), pp. 191-197.

Collins D.W., et al., "Numerical Classification of Coding Sequences," Nucleic Acids Research, 1992, vol. 20 (6), pp. 1405-1410.

Conrads G., et al., "16S-23S rDNA Internal Transcribed Spacer Sequences for Analysis of the Phylogenetic Relationships Among Species of the Genus *Fusobacterium*," International Journal of Systematic and Evolutionary Microbiology, 2002, vol. 52 (2), pp. 493-499.

Contreras-Salazar B., et al., "Up Regulation of the Epstein-Barr Virus (EBV)-Encoded Membrane Protein LMP in the Burkitt's Lymphoma Line Daudi after Exposure to N-Butyrate and after EBV Superinfection," Journal of Virology, 1990, vol. 64 (11), pp. 5441-5447.

Co-pending U.S. Appl. No. 10/318,463, filed Dec. 13, 2002.
Co-pending U.S. Appl. No. 10/323,186, filed Dec. 18, 2002.
Co-pending U.S. Appl. No. 10/323,187, filed Dec. 18, 2002.
Co-pending U.S. Appl. No. 10/324,721, filed Dec. 18, 2002.
Co-pending U.S. Appl. No. 10/521,662, filed Jul. 21, 2003.
Co-pending U.S. Appl. No. 10/807,019, filed Mar. 23, 2004.
Co-pending U.S. Appl. No. 10/845,052, filed May 12, 2004.
Co-pending U.S. Appl. No. 10/964,571, filed Oct. 12, 2004.
Co-pending U.S. Appl. No. 11/209,439, filed Aug. 23, 2005.
Co-pending U.S. Appl. No. 90/010,209, filed Jun. 27, 2008.
Co-pending U.S. Appl. No. 90/010,210, filed Jun. 27, 2008.
Co-pending U.S. Appl. No. 90/010,447, filed Apr. 9, 2009.

(56) References Cited

OTHER PUBLICATIONS

Co-pending U.S. Appl. No. 90/010,448, filed Apr. 9, 2009.
Co-pending U.S. Appl. No. 60/639,068, filed Dec. 22, 2004.
Co-pending U.S. Appl. No. 60/648,188, filed Jan. 28, 2005.
Co-pending U.S. Appl. No. 60/369,405, filed Apr. 1, 2002.
Co-pending U.S. Appl. No. 60/397,365, filed Jul. 19, 2002.
Co-pending U.S. Appl. No. 60/431,319, filed Dec. 6, 2002.
Co-pending U.S. Appl. No. 60/443,443, filed Jan. 29, 2003.
Co-pending U.S. Appl. No. 60/443,788, filed Jan. 30, 2003.
Co-pending U.S. Appl. No. 60/447,529, filed Feb. 14, 2003.
Co-pending U.S. Appl. No. 60/453,607, filed Mar. 10, 2003.
Co-pending U.S. Appl. No. 60/461,494, filed Apr. 9, 2003.
Co-pending U.S. Appl. No. 60/470,175, filed May 12, 2003.
Co-pending U.S. Appl. No. 60/501,926, filed Sep. 11, 2003.
Co-pending U.S. Appl. No. 60/509,911, filed Oct. 9, 2003.
Co-pending U.S. Appl. No. 60/604,329, filed Aug. 24, 2004.
Co-pending U.S. Appl. No. 60/615,387, filed Sep. 30, 2004.
Co-pending U.S. Appl. No. 60/701,404, filed Jul. 21, 2005.
Co-pending U.S. Appl. No. 60/705,631, filed Aug. 3, 2005.
Co-pending U.S. Appl. No. 60/720,843, filed Sep. 27, 2005.
Co-pending U.S. Appl. No. 60/747,607, filed May 18, 2006.
Co-pending U.S. Appl. No. 60/771,101, filed Feb. 6, 2006.
Co-pending U.S. Appl. No. 60/773,124, filed Feb. 13, 2006.
Co-pending U.S. Appl. No. 60/891,479, filed Feb. 23, 2007.
Co-pending U.S. Appl. No. 60/941,641, filed Jun. 1, 2007.
Cornel A.J., et al., "Polymerase Chain Reaction Species Diagnostic Assay for *Anopheles quadrimaculatus* Cryptic Species (*Diptera culicidae*) Based on Ribosomal DNA ITS2 Sequences," Journal of Medical Entomology, 1996, vol. 33 (1), pp. 109-116.
Couto I., et al., "Development of Methicillin Resistance in Clinical Isolates of *Staphylococcus sciuri* by Transcriptional Activation of the mecA Homologue Native to the Species," Journal of Bacteriology, 2003, vol. 185 (2), pp. 645-653.
Crain P.F., et al., "Applications of Mass Spectrometry to the Characterization of Oligonucleotides and Nucleic Acids," Current Opinion in Biotechnology, 1998, vol. 9 (1), pp. 25-34.
Crawford-Miksza L., et al., "Analysis of 15 Adenovirus Hexon Proteins Reveals the Location and Structure of Seven Hypervariable Regions Containing Serotype-Specific Residues," Journal of Virology, 1996, vol. 70 (3), pp. 1836-1844.
Crawford-Miksza L.K., et al., "Adenovirus Serotype Evolution is Driven by Illegitimate Recombination in the Hypervariable Regions of the Hexon Protein," Virology, 1996, vol. 224 (2), pp. 357-367.
Crawford-Miksza L.K., et al., "Strain Variation in Adenovirus Serotypes 4 and 7a Causing Acute Respiratory Disease," Journal of Clincal Microbiology, 1999, vol. 37 (4), pp. 1107-1112.
Crespillo M., et al., "Mitochondrial DNA Sequences for 118 Individuals from Northeastern Spain," International Journal of Legal Medicine, 2000, vol. 114 (1-2), pp. 130-132.
Cui L., et al., "Contribution of a Thickened Cell Wall and Its Glutamine Nonamidated Component to the Vancomycin Resistance Expressed by *Staphylococcus aureus* Mu50," Antimicrobial Agents and Chemotherapy, 2000, vol. 44 (9), pp. 2276-2285.
Dasen G., et al., "Classification and Identification of Propiolbacteria based on Ribosomal RNA Genes and PCR," Systematic and Applied Microbiology, 1998, vol. 21 (2), pp. 251-259.
De Jong J.C., et al., "Adenoviruses from Human Immunodeficiency Virus-Infected Individuals, Including Two Strains that Represent New Candidate Serotypes Ad50 and Ad51 of Species B1 and D, Respectively," Journal of Clincal Microbiology, 1999, vol. 37 (12), pp. 3940-3945.
De La Puente-Redondo V.A., et al., "Comparison of Different PCR Approaches for Typing of Francisella Tularensis Strains," Journal of Clinical Microbiology, 2000, vol. 38 (3), pp. 1016-1022.
Deforce D.L., et al., "Analysis of Oligonucleotides by ESI-MS," Advances in Chromatography, 2000, vol. 40, pp. 539-566.
Deforce D.L.D., et al., "Characterization of DNA Oligonudeotides by Coupling of Capillary zone Electrophoresis to Electrospray Ionization Q-TOF Mass Spectrometry," Analytical Chemistry, 1998, vol. 70 (14), pp. 3060-3068.

Del Blanco Garcia N., et al., "Genotyping of Francisella Tularensis Strains by Pulsed-field gel Electrophoresis, Amplified Fragment Length Polymorphism Fingerprinting, and 16S rRNA gene Sequencing," Journal of Clinical Microbiology, 2002, vol. 40 (8), pp. 2964-2972.
Del Vecchio V.G., et al., "Molecular Genotyping of Methicillin-Resistant *Staphylococcus aureus* via Fluorophore-Enhanced Repetitive-Sequence PCR," Journal of Clincal Microbiology, 1995, vol. 33 (8), pp. 2141-2144.
Demesure B., et al., "A Set of Universal Primers for Amplification of Polymorphic Non-Coding Regions of Mitochondrial and Chioroplast DNA in Plants," Molecular Ecology, 1995, vol. 4, pp. 129-131.
Denis M., et al., "Development of a Semiquantitative PCR Assay Using Internal Standard and Colorimetricdetection on Microwell Plate for Pseudorabies Virus," Molecular and Cellular Probes, 1997, vol. 11 (6), pp. 439-448.
Deurenberg R.H., et al., "Rapid Detection of Panton-Valentine Leukocidin from Clinical Isolates of *Staphylococcus aureus* Strains by Real-Time PCR," FEMS Microbiology Letters, 2004, vol. 240 (2), pp. 225-228.
Deurenberg R.H., et al., "The Prevalence of the *Staphylococcus aureus* tst Gene among Community- and Hospital-Acquired Strains and Isolates from Wegener's Granulomatosis Patients," FEMS Microbiology Letters, 2005, vol. 245 (1), pp. 185-189.
Deyde V.M., et al., "Genomic Signature-Based Identification of Influenza A Viruses Using RT-PCR/Electro-Spray Ionization Mass Spectrometry (ESI-MS) Technology," PLoS One, 2010, vol. 5 (10), pp. e13293.
Di Guilmi A.M., et al., "Human Adenovirus Serotype 3 (Ad3) and the Ad3 fiber Protein Bind to a 130-kDa Membrane Protein on HLa Cells," Virus Research, 1995, vol. 38 (1), pp. 71-81.
Dias Neto E., et al., "Shotgun Sequencing of the Human Transcriptome with ORF Expressed Sequence Tags," Proceedings of the National Academy of Sciences, 2000, vol. 97 (7), pp. 3491-3496.
Diep B.A., et al., "Complete Genome Sequence of USA300, an Epidemic Clone of Community Acquired Meticillin-Resistant *Staphylococcus aureus*," Lancet, 2006, vol. 367 (9512), pp. 731-739.
Dinauer D.M., et al., "Sequence-Based Typing of HLA Class II DQB1," Tissue Antigens, 2000, vol. 55 (4), pp. 364-368.
Ding C., et al., "A High-Throughput Gene Expression Analysis Technique Using Compettiive PCR and Matrixassisted Laser Desorption Ionization Time-of-Flight MS," Proceedings of the National Academy of Sciences, 2003, vol. 100 (6), pp. 3059-3064.
Donehower L.A., et al., "The Use of Primers from Highly Conserved Pol Regions to Identify Uncharacterized Retroviruses by the Polymerase Chain Reaction," Journal of Virological Methods, 1990, vol. 28 (1), pp. 33-46.
Donofrio J.C., et al., "Detection of Influenza A and B in Respiratory Secretions with the Polymerase Chain Reaction," PCR Methods and Applications, 1992, vol. 1 (4), pp. 263-268.
Doty P., et al., "Strand Separation and Specific Recombination in Deoxyribonucleic Acids: Physical Chemical Studies," Proceedings of the National Academy of Sciences, 1960, vol. 46 (4), pp. 461-476.
Drosten C., et al., "Identification of a Novel Coronavirus in Patients with Severe Acute Respiratory Syndrome," New England Journal of Medicine, 2003, vol. 348 (20), pp. 1967-1976.
Dubernet S., et al., "A PCR-Based Method for Identification of *Lactobacilli* at to Genus Level," FEMS Microbiology Letters, 2002, vol. 214 (2), pp. 271-275.
Ebner K., et al., "Molecular Detection and Quantitative Analysis of the Entire Spectrum of Human Adenoviruses by a Two-Reaction Real-Time PCR Assay," Journal of Clinical Microbiology, 2005, vol. 43 (7), pp. 3049-3053.
Ebner K., et al., "Typing of Human Adenoviruses in Specimens from Immunosuppressed Patients by PCR-Fragment Length Analysis and Real-Time Quantitative PCR," Journal of Clinical Microbiology, 2006, vol. 44 (8), pp. 2808-2815.
Echavarria M., et al., "Detection of Adenoviruses (AdV) in Culture-Negative EnvironmentalSamples by PCR During an AdV-Associ-

(56) References Cited

OTHER PUBLICATIONS ated Respiratory Disease Outbreak," Journal of Clinical Microbiology, 2000, vol. 38 (8), pp. 2982-2984.
Echavarria M., et al., "PCR Method for Detection of Adenovirus in Urine of Healthy and Human Immunodeficiency Virus-Infected Individuals," Journal of Clinical Microbiology, 1998, vol. 36 (11), pp. 3323-3326.
Echavarria M., et al., "Prediction of Severe Disseminated Adenovirus Infection by Serum PCR," Lancet, 2001, vol. 358 (9279), pp. 384-385.
Echavarria M., et al., "Rapid Detection of Adenovirus in Throat Swab Specimens by PCR During Respiratory Disease Outbreaks among Military Recruits," Journal of Clinical Microbiology, 2003, vol. 41 (2), pp. 810-812.
Echavarria M., et al., "Use of PCR to Demonstrate Presence of Adenovirus Species B, C, or F as Well as Coinfection with Two Adenovirus Species in Children with Flu-Like Symptoms," Journal of Clinical Microbiology, 2006, vol. 44 (2), pp. 625-627.
Ecker D.J., et al., "Ibis T5000: A Universal Biosensor Approach for Microbiology," Nature Reviews Microbiology, 2008, vol. 6 (7), pp. 553-558.
Ecker D.J., et al., "Rapid Identification and Strain-Typing of Respiratory Pathogens for Epidemic Surveillance," Proceedings of the National Academy of Sciences, 2005, vol. 102 (22), pp. 8012-8017.
Ecker D.J., et al., "The Ibis T5000 Universal Biosensor. An Automated Platform for Pathogen Identification and Strain Typing," Journal of the Association for Laboratory Automation, 2006, vol. 11 (6), pp. 341-351.
Ecker Supporting Information [online], May 23, 2005 [retrieved on Jul. 31, 2011]. Retrieved from the Internet:<URL: http://www.pnas.org/content/102/22/8012/suppl/DC1>.
Edwards K.M., et al., "Adenovirus Infections in Young Children," Pediatrics, 1985, vol. 76 (3), pp. 420-424.
Ellis J.S., et al., "Molecular Diagnosis of Influenza," Reviews in Medical Virology, 2002, vol. 12 (6), pp. 375-389.
Ellis J.S., et al., "Multiplex Reverse Transcription-PCR for Surveillance of Influenza A and B Viruses in England and Wales in 1995 and 1996," Journal of Clinical Microbiology, 1997, vol. 35(8), pp. 2076-2082.
Elnifro E.M., et al., "PCR and Restriction Endonuclease Analysis for Rapid Identification of Adenovirus Subgenera," Journal of Clinical Microbiology, 2000, vol. 38 (6), pp. 2055-2061.
Elsayed S., et al., "Development and Validation of a Molecular Beacon Probe-Based Real-Time Polymerase Chain Reaction Assay for Rapid Detection of Methicillin Resistance in *Staphylococcus aureus*," Archives of Pathology and Laboratory Medicine, 2003, vol. 127 (7), pp. 845-849.
EMBL "Arabidopsis Thaliana T-DNA Flanking Sequence, Left Border, Clone 346C06," Accession No. AJ552897, Mar. 29, 2003.
EMBL "Dog (Clone: CXX.147) Primer for STS 147, 3" End, Sequence Tagged Site," Accession No. L15697, Mar. 4, 2000.
EMBL "Sequence 10 from U.S. Pat. No. 6,563,025," Accession No. AR321656, Aug. 18, 2003.
EMBL "Human, muscle, Mitochondrial Mutant, 22 nt, segment 2 of 2," Accession No. S90302, Sep. 1, 2004.
EMBL "Synthetic Construct DNA, Reverse Primer for Human STS sts-AA031654 at 1p36" Accession No. AB068711, May 21, 2003.
Enright M.C., et al., "A Multilocus Sequence Typing Scheme for *Streptococcus pneumoniae*: Identification of Clones Associated with Serious Invasive Disease," MICROBIOLOGY, 1998, vol. 144 (Pt 11), pp. 3049-3060.
Enright M.C., et al., "Multilocus Sequence Typing for Characterization of Methicillin-Resistant and Methicillin-Susceptible Clones of *Staphylococcus aureus*," Journal of Clinical Microbiology, 2000, vol. 38 (3), pp. 1008-1015.
Enright M.C., et al., "Multilocus Sequence Typing of *Streptococcus pyogenes* and theRelationships between Emm Type and Clone," Infection and Immunity, 2001, vol. 69 (4), pp. 2416-2427.

Enright M.C., et al., "The Evolutionary History of Methicillin-Resistant *Staphylococcus aureus* (MRSA)," Proceedings of the National Academy of Sciences, 2002, vol. 99 (11), pp. 7687-7692.
Enright M.C., "The Evolution of a Resistant Pathogen—the Case of MRSA," Current Opinion in Pharmacology, 2003, vol. 3 (5), pp. 474-479.
Eremeeva M.E., et al., "Evaluation of a PCR Assay for Quantitation of Rickettsia rickettsii and Closely Related Spotted Fever Group Rickettsiae," Journal of Clinical Microbiology, 2003, vol. 41 (12), pp. 5466-5472.
Erlich H.A., Ed., PCR Technology: Principles and Applications for DNA Amplification, W.H. Freeman and Company, 1989.
Esmans E.L., et al., "Liquid Chromatography-Mass Spectrometry in Nucleoside, Nucleotide and Modified Nucleotide Characterization," Journal of Chromatography, 1998, vol. 794, pp. 109-127.
Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.
Evans P., et al., "Practical Algorithms for Universal DNA Primer Design: An Exercise in Algorithm Engineering," Currents in Computational Molecular Biology, 2001, pp. 25-26.
Ex Parte Re-Examination Certificate for U.S. Appl. No. 90/010,209 mailed Jul. 7, 2009.
Ex Parte Re-Examination Certificate for U.S. Appl. No. 90/010,210, mailed Dec. 28, 2010.
Ex Parte Re-Examination Certificate for U.S. Appl. No. 90/010,447 mailed Feb. 15, 2011.
Examiner Interview Summary Report mailed Oct. 3, 2005 for U.S. Appl. No. 10/326,046, filed Dec. 18, 2002.
Examiner Interview Summary Report mailed Nov. 6, 2008 for U.S. Appl. No. 10/728,486, filed Dec. 5, 2003.
Examiner Interview Summary Report mailed Jun. 7, 2011 for U.S. Appl. No. 11/930,108, filed Oct. 31, 2007.
Examiner Interview Summary Report mailed Aug. 10, 2004 for U.S. Appl. No. 09/798,007, filed Mar. 2, 2001.
Examiner Interview Summary Report mailed Aug. 10, 2004 for U.S. Appl. No. 09/891,793, filed Jun. 26, 2001.
Examiner Interview Summary Report mailed Aug. 10, 2004 for U.S. Appl. No. 10/156,608, filed May 24, 2002.
Examiner Interview Summary Report mailed Aug. 10, 2004 for U.S. Appl. No. 10/326,642, filed Dec. 18, 2002.
Examiner Interview Summary Report mailed May 19, 2003 for U.S. Appl. No. 09/891,793, filed Jun. 26, 2001.
Examiner Interview Summary Report mailed Oct. 24, 2008 for U.S. Appl. No. 11/582,859, filed Oct. 17, 2006.
Examiner Interview Summary Report mailed Oct. 24, 2008 for U.S. Appl. No. 11/582,930, filed Oct. 17, 2006.
Examiner Interview Summary Report mailed Feb. 27, 2006 for U.S. Appl. No. 10/326,644, filed Dec. 18, 2002.
Examiner Interview Summary Report mailed Jan. 27, 2006 for U.S. Appl. No. 10/323,211, filed Dec. 18, 2002.
Examiner Interview Summary Report mailed May 28, 2008 for U.S. Appl. No. 10/660,998, filed Sep. 12, 2003.
Examiner Interview Summary Report mailed Oct. 28, 2008 for U.S. Appl. No. 11/331,987, filed Jan. 13, 2006.
Examiner Interview Summary Report mailed Oct. 29, 2008 for U.S. Appl. No. 11/331,978, filed Jan. 13, 2006.
Examiner Interview Summary Report mailed Oct. 29, 2009 for U.S. Appl. No. 10/660,122, filed Sep. 11, 2003.
Examiner Interview Summary Report mailed Jul. 31, 2006 for U.S. Appl. No. 10/326,643, filed Dec. 18, 2002.
Extended European Search Report for Application No. EP10175659.1, mailed on Feb. 21, 2011, 8 pages.
Extended European Search Report for Application No. EP10179789.2, mailed on Mar. 22, 2011, 9 pages.
Extended European Search Report for Application No. EP10179791.8, mailed on Mar. 17, 2011, 7 pages.
Extended European Search Report for Application No. EP10179795.9, mailed on Mar. 22, 2011, 9 pages.

(56) References Cited

OTHER PUBLICATIONS

Facklam R., et al., "Emm Typing and Validation of Provisional M Types for Group A *Streptococci*," Emerging Infectious Diseases, 1999, vol. 5 (2), pp. 247-253.

Fang H., et al., "Rapid Screening and Identification of Methicillin-Resistant *Staphylococcus aureus* from Clinical Samples by Selective-Broth and Real-Time PCR Assay," Journal of Clinical Microbiology, 2003, vol. 41 (7), pp. 2894-2899.

Farlow J., et al., "Francisella Tularensis Strain Typing Using Multiple-Locus, Variable-Number Tandem Repeat Analysis," Journal of Critical Microbiology, 2001, vol. 39 (9), pp. 3186-3192.

Farrell D.J., "The Reliability of Microscan Conventional and Rapid Panels to Identify *Staphylococcus aureus* and Detect Methicillin Resistance: An Evaluation Using the Tube Coagulase Test and mecA PCR," Pathology, 1997, vol. 29 (4), pp. 406-410.

Fedele C.G., et al., "Multiplex Polymerase Chain Reaction for the Simultaneous Detection and Typing of Polyomavirus JC, BK and SV40 DNA in Clinical Samples," Journal of Virological Methods, 1999, vol. 82 (2), pp. 137-144.

Fedele C.G., et al., "Quantitation of Polyomavirus DNA by a Competitive Nested Polymerase Chain Reaction," Journal of Virological Methods, 2000, vol. 88 (1), pp. 51-61.

Feng P., "Impact of Molecular Biology on the Detection of Food Pathogens," Molecular Biotechnology, 1997, vol. 7 (3), pp. 267-278.

Figueiredo L.M., et al., "Identification of Brazilian Flavivirus by a Simplified Reverse Transcription-Polymerase Chain Reaction Method Using Flavivirus Universal Primers," American Journal of Tropical Medicine and Hygiene, 1998, vol. 59 (3), pp. 357-362.

Final Office Action mailed Aug. 6, 2010 for U.S. Appl. No. 11/929,910, filed Oct. 30, 2007.

Final Office Action mailed Jul. 8, 2010 for U.S. Appl. No. 12/326,800, filed Dec. 2, 2008.

Final Office Action mailed May 12, 2010 for U.S. Appl. No. 11/674,538, filed Feb. 13, 2007.

Final Office Action mailed Apr. 14, 2011 for U.S. Appl. No. 12/049,949, filed Mar. 17, 2008.

Final Office Action mailed Jun. 14, 2011 for U.S. Appl. No. 12/616,422, filed Nov. 11, 2009.

Final Office Action mailed Oct. 14, 2009 for U.S. Appl. No. 10/943,344, filed Sep. 17, 2004.

Final Office Action mailed Nov. 17, 2009 for U.S. Appl. No. 11/582,875, filed Oct. 17, 2006.

Final Office Action mailed Feb. 18, 2010 for U.S. Appl. No. 10/754,415, filed Jan. 9, 2004.

Final Office Action mailed Nov. 20, 2009 for U.S. Appl. No. 11/331,987, filed Jan. 13, 2006.

Final Office Action mailed Jun. 23, 2010 for U.S. Appl. No. 11/930,017, filed Oct. 30, 2007.

Final Office Action mailed Feb. 26, 2009 for U.S. Appl. No. 11/582,863, filed Oct. 17, 2006.

Final Office Action mailed Jan. 30, 2009 for U.S. Appl. No. 10/844,938, filed May 12, 2004.

Flora J.W., et al, "Dual-Micro-ESI Source for Precise Mass Determination on a Quadrupole Time-of-Flight Mass Spectrometer for Genomic and Proteomic Applications," Analytical and Bioanalytical Chemistry, 2002, vol. 373 (7), pp. 538-546.

Fong W.K., et al., "Rapid Solid-Phase Immunoassay for Detection of Methicillin-Resistant*Staphylococcus aureus* Using Cycling Probe Technology," Journal of Clinical Microbiology, 2000, vol. 38 (7), pp. 2525-2529.

Fox A., et al., "Identification and Detection of Bacteria: Electrospray MS-MS Versus Derivatization/GC-MS," Proceedings of the ERDEC Scientific Conference on Chemical and Biological Defense Research, Aberdeen Proving Ground, MD, Nov. 15-18, 1994, pp. 39-44.

Fox A., et al., "Report of the Bioterrorism Workshop," Journal of Microbiological Methods, 2002, vol. 51 (3), pp. 247-254.

Fox J.P., et al., "The Virus Watch Program: A Continuing Surveillance of Viral Infections in Metropolitan New York Families," American Journal of Epidemiology, 1969, vol. 89 (1), pp. 25-50.

Fox K.F., et al., "Identification of *Brucella* by Ribosomal-Spacer-Region PCR and Differentiation of *Brucell canis* from Other *Brucella* Spp. Pathogenic for Humans by Carbohydrate Profiles," Journal of Clinical Microbiology, 1998, vol. 36 (11), pp. 3217-3222.

Francois J.C., et al., "Sequence-Specific Recognition and Cleavage of Duplex DNA via Triple-Helix Formation by Oligonucleotides Covalently Linked to a Phenanthroline-Copper Chelate," Proceedings of the National Academy of Sciences, 1989, vol. 86 (24), pp. 9702-9706.

Francois P., et al., "Rapid Detection of Methicillin-Resistant *Staphylococcus aureus* Directly from Sterile or Nonsterile Clinical Samples by a New Molecular Assay," Journal of Clinical Microbiology, 2003, vol. 41 (1), pp. 254-260.

Fraser C.M., et al., "The Mimimal Gene Complement of Mycoplasma Genitalium," Science, 1995, vol. 270 (5235), pp. 397-403.

Freiberg C., et al., "Genome-Wide mRNA Profiling: Impact on Compound Evaluation and Target Identification in Anti-Bacterial Research," Targets, 2002, vol. 1 (1), pp. 20-29.

Freymuth F., et al., "Comparison of Multiplex PCR Assays and Conventional Techniques for the Diagnostic of Respiratory Virus Infections in Children Admitted to Hospital With an Acute Respiratory Illness," Journal of Medical Virology, 2006, vol. 78 (11), pp. 1498-1504.

Freymuth F., et al., "Detection of Respiratory Syncytial Virus, Parainfluenzavirus 3, Adenovirus Andrhinovirus Sequences in Respiratory Tract of Infants by Polymerase Chain Reaction and Hybridization," Clinical and Diagnostic Virology, 1997, vol. 8 (1), pp. 31-40.

Fuerstenau S.D., et al., "Molecular Weight Determination of Megadalton DNA Electrospray Ions Using Charge Detection Time-of-flight Mass Spectrometry," Rapid Communications in Mass Spectrometry, 1995, vol. 9 (15), pp. 1528-1538.

Fujimoto T., et al., "Single-Tube Multiplex. PCR for Rapid and Sensitive Diagnosis of Subgenus B and Other Subgenera Adenoviruses in Clinical Samples," Microbiology and Immunology, 2000, vol. 44 (10), pp. 821-826.

Fujimura S., et al., "Characterization of the mupA Gene in Strains of Methicillin-Resistant *Staphylococcus aureus* with a Low Level of Resistance to Mupirocin," Antimicrobial Agents and Chemotherapy, 2001, vol. 45 (2), pp. 641-642.

Fujimura S., et al., "Isoleucyl-tRNA Synthetase Mutations in *Staphylococcus aureus* Clinicallsolates and In Vitro Selection of Low-Level Mupirocin-Resistant Strains," Antimicrobial Agents and Chemotheraphy, 2003, vol. 47 (10), pp. 3373-3374.

Fujioka S., et al., "Analysis of Enterovirus Genotypes using Single-Strand Conformation Polymorphisms of Polymerase Chain Reaction Product," Journal of Virological Methods, 1995, vol. 51 (2-3), pp. 253-258.

Gabriel M.N., et al., "Improved mtDNA Sequence Analysis of Forensic Remains using a "Mini-Primer Set" Amplification Strategy," Journal of Forensic Sciences, 2001, vol. 46 (2), pp. 247-253.

Gall J.G., et al., "Construction and Characterization of Hexon-Chimeric Adenoviruses: Specification of Adenovirus Serotype," Journal of Virology, 1998, vol. 72 (12), pp. 10260-10264.

Gammelin M., et al., "Two Subtypes of Nucleoproteins (NP) of Influenza A Viruses," Virology, 1989, vol. 170 (1), pp. 71-80.

Garcia S., et al., "Quantitative Real-Time PCR Detection of Rift Valley Fever Virus and Its Application to Evaluation of Antiviral Compounds," Journal of Clinical Microbiology, 2001, vol. 39 (12), pp. 4456-4461.

Garcia-Martinez J., et al., "Use of the 16s-23s Ribosomal Genes Spacer Region in Studies of Prokaryotic Diversity," Journal of Microbiological Methods, 1999, vol. 36 (1-2), pp. 55-64.

Gattermann N., et al., "Heteroplasmic Point Mutations of Mitochondrial DNA Affecting Subunit I of Cytochrome c Oxidise in Two Patients with Acquired Idiopathic Siderblastic Anemia," Blood, 1997, vol. 90 (12), pp. 4961-4972.

Gaydos C.A., et al., "Adenovirus Vaccines in the U.S. Military," Military Medicine, 1995, vol. 160 (6), pp. 300-304.

(56) References Cited

OTHER PUBLICATIONS

Geha D.J., et al., "Multiplex PCR for Identification of Methicillin-Resistant *Staphylococci* in the Clinical Laboratory," Journal of Clinical Microbiology, 1994, vol. 32 (7), pp. 1768-1772.
Genbank, "Acinetobacter Genomosp. 10 Strain CIP 70.12 RNA Polymerase Subunit B (rpoB) Gene, Complete Cds," Accession No. 78099429, Mar. 11, 2006.
GenBank, "Bovine Parainfluenza Virus 3 Strain Shipping Fever, Complete Genome," Accesion No. AF178655, Sep. 19, 2000.
GenBank, "Clostridium Tetani E88, Complete Genome," Accession No. AE015927.1, Feb. 4, 2003.
GenBank, "{Deletion 6} [Human, Muscle, Mitochondrial Mutant, 22 nt, Segment 2 of 2]," Accession No. S90302.1, Jun. 10, 1992.
GenBank, "*E. coli* Operon rpoBC Coding for the Beta- and Beta"-Subunits of RNA Polymerase (Genes rpoC and rpoB), and Genes rplL, rlpJ, rplA, and rplK Coding for 50S Ribosomal Subunit Proteins L7/L12, L10, L1, and L11, Respectively. (Map position 89-90 min.), Accession No. 42813, Feb. 28, 1992.
GenBank, "*E.coli* 16S Ribosomal RNA," Accession No. 174375, Aug. 11, 1995.
GenBank, "*E.coli* Open Reading Frame Upstream of Leu Operon," Accession No. M21150, Sep. 15, 1990.
GenBank, "*E.coli* rRNA Operon (rrnB) Coding for Glu-tRNA-2, 5S, 16S and 23S rRNA," Accession No. 147581, Sep. 14, 1992.
GenBank, "Enterococcus malodoratus Strain ATCC43197 Elongation Factor Tu (tufA) Gene, Partial Cds," Accession No. AF274728, Dec. 11, 2000.
GenBank "*Escherichia coli* str. K-12 substr. MG1655, Complete Genome," Accession No. NC000913, Oct. 15, 2001.
GenBank, "*Homo sapiens* Haplotype V Mitochondrion, Complete Genome", Accession No. AF381990.1, Dec. 28, 2001.
GenBank, "Human Adenovirus Type 4 Hexon Gene," for Accession No. X84646, Jun. 30, 1995.
GenBank, "Human Coronavirus 229E, Complete Genome," Accession No. AF304460, Jul. 11, 2001.
GenBank, "Human Isolate L34 Mitochondrion D-loop Region", Accession No. U08081.1, Aug. 16, 1994.
GenBank, "il11b08.y1 Human insulinoma *Homo sapiens* cDNA clone IMAGE:6029534 5- similar to SW:COX3_HUMAN P00414 Cytochrome C Oxidase Polypeptide III ;, mRNA sequence", Accession No. BQ581956.1, Jun. 20, 2002.
GenBank, "Influenza B Virus B/Panama/45/90 Polymerase (PB2) mRNA, Complete Cds", Accession No. AF005737, Oct. 4, 1997, pp. 1-3.
GenBank, "Mastadenovirus h7 Hexon Gene," Accession No. Z48571, Apr. 18, 2005.
GenBank, "or72a01.s1 NCI_CGAP_Lu5 *Homo sapiens* cDNA Clone IMAGE:1601352 3- similar to SW:COX1_HUMAN P00395 Cytochrome C Oxidase Polypeptide I ;, mRNA sequence", Accession No. A1002209.1, Jun. 10, 1998.
GenBank "*Staphylococcus aureus* RN4220 ErmC Gene, Partial Cds," Accession No. 18542231, Sep. 16, 2003.
GenBank "*Staphylococcus aureus* Strain MSSA476, Complete Genome," Accession No. BX571857.1, Jun. 24, 2004.
GenBank, "*Staphylococcus aureus* Subsp. *aureus* Mu50, Complete Genome," Accession No. 15922990, Oct. 4, 2001.
GenBank "*Staphylococcus aureus* Subsp. *aureus* MW2, Complete Genome," Accession No. G121281729, May 31, 2002.
GenBank, "*Staphylococcus epidermidis* ATCC 12228, Complete Genome," Accession No. AE015929.1, Jan. 2, 2003.
GenBank "*Streptococcus agalactiae* 2603V/R, Complete Genome," Accession No. AE009948.1, Aug. 28, 2002.
GenBank, "*Streptococcus anginosus* Elongation Factor Tu (tuf) Gene, Partial cds," Accession No. AF276257.1, Jul. 1, 2001.
GenBank, "*Streptococcus pneumoniae* Isolate 95.11n00S DNA Gyrase Subunit B (gyrB) Gene, Complete Cds," Accession No. 73916349, Sep. 30, 2005.
GenBank, "*Streptococcus pyogenes* Strain MGAS8232, Complete Genome," Accession No. AE009949.1, Apr. 3, 2002.
GenBank, "Venezuelan Equine Encephalitis Virus Nonstructural Polyprotein and Structural Polyprotein Genes, Complete Cds," Accession No. AF375051.1, Jun. 26, 2001.
Gendel S.M., "Computational Analysis of the Specificity of 16S rRNA-Derived Signature Sequencesfor Identifying Food-Related Microbes," Food Microbiology, 1996, vol. 13, pp. 1-15.
Gibb T.R., et al., "Development and Evaluation of a 5" Fluorogenic Nuclease Assay to Detect and Differentiate Between Ebola Virus Subtypes Zaire and Sudan," Journal of Clinical Microbiology, 2001, vol. 39 (11), pp. 4125-4130.
Gilbert N., et al., "Comparison of Commercial Assays for the Quantitation of HBV DNA Load in Healthcare Workers: Calibration Differences," Journal of Virological Methods, 2002, vol. 100 (1-2), pp. 37-47.
Giles R.E., et al., "Maternal Inheritance of Human Mitochondrial DNA," Proceedings of the National Academy of Sciences, 1980, vol. 77 (11), pp. 6715-6719.
Gill S.R., et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidemidis* Strain," Journal of Bacteriology, 2005, vol. 187 (7), pp. 2426-2438.
Gilliland G., et al., "Analysis of Cytokine mRNA and DNA: Detection and Quantitation by Competitive Polymerase Chain Reaction," Proceedings of the National Academy of Sciences, 1990, vol. 87 (7), pp. 2725-2729.
Ginther C., et al., "Identifying Individuals by Sequencing Mitochondrial DNA from Teeth," Nature Genetics, 1992, vol. 2 (2), pp. 135-138.
Gjoen K.V., et al., "Specific Detection of Coxsackie Viruses A by the Polymerase Chain Reaction," Clinical and Diagnostic Virology, 1997, vol. 8 (3), pp. 183-188.
Golden M.R., et al., "Pilot Study of COBAS PCR and Ligase Chain Reaction for Detection of Rectal Infections Due to Chlamydia Trachomatis," Journal of Clinical Microbiology, 2003, vol. 41 (5), pp. 2174-2175.
Goto K., et al., "Applications of the Partial 16S rDNA Sequence as an Index for Rapid Identification of Species in the Genus *Bacillus*," Journal of General and Applied Microbiology, 2000, vol. 46 (1), pp. 1-8.
Gravet A., et al., "Characterization of a Novel Structural Member, LukE-LukD, of the Bi-Component *Staphylococcal leucotoxins* Family," FEBS Letters, 1998, vol. 436 (2), pp. 202-208.
Gray G.C., et al., "Adult Adenovirus Infections: Loss of Orphaned Vaccines Precipitates Military Respiratory Disease Epidemics," Clinical Infectious Diseases, 2000, vol. 31, pp. 663-670.
Greenberg B.D., et al., "Intraspecific Nucleotide Sequence Variability Surrounding the Origin of Replicationin Human Mitochondrial DNA," Gene, 1983, vol. 21, pp. 33-49.
Griffey, et al., "Detection of Base Pair Mismatches in Duplex DNA and RNA Oligonucleotides Using Electrospray Mass Spectrometry," SPIE, 1997, vol. 2985, pp. 82-86.
Griffin T.J., et al., "Direct Genetic Analysis by Matrix-Assisted Laseer Desorption/Ionization Mass Spectrometry," Proceedings of the National Academy of Sciences, 1999, vol. 96 (11), pp. 6301-6306.
Griffin T.J., et al., "Single-Nucleotide Polymorphism Analysis by Maldi-TOF Mass Spectrometry," Trends in Biotechnology, 2000, vol. 18 (2), pp. 77-84.
Grondahl B., et al., "Rapid Identification of Nine Microorganisms Causing Acute Respiratory TractInfections by Single-Tube Multiplex Reverse Transcription-PCR: Feasibility Study," Journal of Clinical Microbiology, 1999, vol. 37 (1), pp. 1-7.
Grundmann H., et al., "Emergence and Resurgence of Meticillin-Resistant *Staphylococcus aureus* as a Public-Health Threat," Lancet, 2006, vol. 368 (9538), pp. 874-885.
Grzybowski T., et al., "Extremely High Levels of Human Mitochondrial DNA Heteroplasmy in Single Hair Roots," Electrophoresis, 2000, vol. 21 (3), pp. 548-553.
Gu Z., et al., "Multiplexed, Real-Time PCR for Quantitative Detection of Human Adenovirus," Journal of Clinical Microbiology, 2003, vol. 41 (10), pp. 4636-4641.

(56) References Cited

OTHER PUBLICATIONS

Guatelli J.C., et al., "Nucleic Acid Amplification In Vitro: Detection of Sequences with Low Copy Numbers and Application to Diagnosis of Human Immunodeficiency Virus Type 1 Infection," Clinical Microbiology Reviews, 1989, vol. 2 (2), pp. 217-226.
Haff L.A., et al., "Multiplex Genotyping of PCR Products with Mass Tag-Labeled Primers," Nucleic Acids Research, 1997, vol. 25 (18), pp. 3749-3750.
Hahner S., et al., "Analysis of Short Tandem Repeat Polymorphisms by Electrospray Ion Trap Mass Spectrometry," Nucleic Acids Research, 2000, vol. 28 (18), pp. E82.1-E82.8.
Haines J.D., et al., "Medical Response to Bioterrorism: Are We Prepared," Journal of Oklahoma State Medical Association, 2000, vol. 93, pp. 187-196.
Hall T.A., et al., "Base Composition Analysis of Human Mitochondrial DNA Using Electrospray Ionization Mass Spectrometry: A Novel Tool for the Identification and Differentiation of Humans," Analytical Biochemistry, 2005, vol. 344 (1), pp. 53-69.
Hamdad F., et al., "Detection of Methicillin/Oxacillin Resistance and Typing in Aminoglycoside-Susceptible Methicillin-Resistant and Kanamycin-Tobramycin-Resistant Methicillin-Susceptible," Microbial Drug Resistance, 2006, 12 (3), 177-185.
Hamel S., et al., "Consensus PCR and Microarray for Diagnosis of the Genus *Staphylococcus*, Species, and Methicillin Resistance," Biotechniques, 2001, vol. 31 (6), pp. 1364-1372.
Hammerle T., et al., "A Sensitive PCR Assay System for the Quantitation of Viral Genome Equivalents:Hepatitis C Virus (HCV)," Archives of Virology, 1996, vol. 141 (11), pp. 2103-2114.
Hannis J.C., et al., "Accurate Characterization of the Tyrosine Hydroxylase Forensic Allele 9.3 through Development of Electrospray Ionization Fourier Transform Ion Cyclotron Resonance Mass Spectrometry," Rapid Communications in Mass Spectrometry, 1999, vol. 13 (10), pp. 954-962.
Hannis J.C., et al., "Detection of Double-Stranded PCR Amplicons at the Attomole Level Electrosprayed from Low Nanomolar Solutions using FT-ICR Mass Spectrometry," Fresenius Journal of Analytical Chemistry, 2001, vol. 369 (3-4), pp. 246-251.
Hannis J.C., et al., "Genotyping Complex Short Tandem Repeats Using Electrospray Ionzation Fourier Transform Ion Cyclotron Resonance Multi-Stage Mass Spectrometry," Proceedings of SPIE, 2000, vol. 3926, pp. 36-47.
Hannis J.C., et al., "Genotyping Short Tandem Repeats Using Flow Injection and Electrospray Ionization, Fourier Transform Ion Cyclotron Resonance Mass Spectrometry," Rapid Communications in Mass Spectrometry, 2001, vol. 15 (5), pp. 348-350.
Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.
Hanssen A.M., et al., "Sccmecin *Staphylococci* : Genes on the Move," FEMS Immuol Medical Microbiol, 2006, vol. 46, pp. 8-20.
Hasebe F. et al., "Combined Detection and Genotyping of Chikungunya Virus by a Specific Reverse Transcription-Polymerase Chain Reaction," Journal of Medical Virology, 2002, vol. 67 (3), pp. 370-374.
Hassan A.A., et al., "Inter- and Intraspecies Variations of the 16S-23S rDNA Intergenic Spacer Region of Various *Streptococcal* Species," Systematic and Applied Microbiology, 2003, vol. 26 (1), pp. 97-103.
Haugland R.A., et al., "Identification of Putative Sequence Specific PCR Primers for Detection of the Toxygenic Fungal Species *Stachybotrys chartarum*," Molecular and Cellular Probes, 1998, vol. 12 (6), pp. 387-396.
Hayashi H., et al., "Phylogenetic Analysis of the Human Gut Microbiota Using 16S rDNA Clone Libraries and Strictly Anaerobic Culture-based Methods," Journal of Microbiology, Immunology, 2002, vol. 46 (8), pp. 535-548.
He L., et al, "Development of a Capillary High-performance Liquid Chromatography Tandem Mass Spectrometry System Using SWIFT Technology in an Ion Trap/Reflectron Time-of-flight Mass Spetrometer," Biochemical and Biophysical Research Communications, 1997, vol. 11, pp. 1739-1748.
Heim A., et al., "Rapid and Quantitative Detection of Human Adenovirus DNA by Real-Time PCR," Journal of Medical Virology, 2003, vol. 70, pp. 228-239.
Henchal E.A., et al., "Sensitivity and Specificity of a Universal Primer Set for the Rapid Diagnosis of Dengue Virus Infections by Polymerase Chain Reaction and Nucleic Acid Hybridization," American Journal of Tropical Medicine and Hygiene, 1991, vol. 45 (4), pp. 418-428.
Herrmann B., et al., "Differentiation of *Chiamydia* spp. by Sequence Determination and Restriction Endonuclease Cleavage of RNase P RNA Genes," Journal of Clinical Microbiology, 1996, vol. 34 (8), pp. 1897-1902.
Higgins G.S., et al., "Competitive Oligonucleotide Single-base Extension Combined with Mass Spectrometric Detection for Mutation Screening," Biotechniques, 1997, vol. 23 (4), pp. 710-714.
Higgins J.A., et al., "Sensitive and Rapid Identification of Biological Threat Agents," Annals of the New York Academy of Sciences, 1999, vol. 894, pp. 130-148.
Hill F., et al., "Polymerase Recognition of Synthetic Oligodeoxyribonucleotides Incorporating Degenerate Pyrimidine and Purine Bases," Proceedings of the National Academy of Sciences, 1998, vol. 95, pp. 4258-4263.
Hiramatsu K., et al., "The Emergence and Evolution of Methicillin-Resistant *Staphylococcusaureus*," Trends Microbiology, 2001, vol. 9 (10), pp. 486-493.
Hodgson J.E., et al., "Molecular Characterization of the Gene Encoding High-Level Mupirocin Resistancein *Staphylococcus aureus* J2870," Antimicrobial Agents and Chemotherapy, 1994, vol. 38 (5), pp. 1205-1208.
Hoffman E., et al., "Rescue of Influenza B Virus from Eight Plasmids," Proceedings of the National Academy of Sciences, 2002, vol. 99 (17), pp. 11411-11416.
Hoffmann E., et al., "Universal Primer Set for the Full-Length Amplification of all Influenza A Viruses," Archives of Virology, 2001, vol. 146 (12), pp. 2275-2289.
Hofstadler S.A., et al., "TIGER: The Universal Biosensor," International Journal of Mass Spectrometry, 2005, vol. 242, pp. 23-41.
Holden M.T., et al., "Complete Genomes of Two Clinical *Staphylocuccus aureus* Strain: Evidence for the Rapid Evolution of Virulence and Drug Resistance," Proceedings of the National Academy of Sciences, 2004, vol. 101 (26), pp. 9786-9791.
Holland M.M., et al., "Mitochondrial DNA Sequence Analsysis—Validation and Use for Forensic Casework," Forensic Science Review, 1999, vol. 11 (1), pp. 22-50.
Holland M.M., et al., "Mitochondrial DNA Sequence Analysis of Human Skeletal Remains: Identification of Remains from the Vietnam War," Journal of Forensic Sciences, 1993, vol. 38 (3), pp. 542-553.
Holm L., et al., "Removing Near-Neighbour Redundancy from Large Protein Sequence Collections," Bioinformatics, 1998, vol. 14 (5), pp. 423-429.
Holmes E.C., et al., "Whole-Genome Analysis of Human Influenza A Virus Reveals Multiple Persistent Lineages and Reassortment among Recent H3N2 Viruses," Public Library of Science Biology, 2005, vol. 3 (9), pp. 1579-1589.
Honda K., et al., "Universal Method of Hypersensitive Nested PCR Toward Forensic DNA typing," International Congress Series, 1998, vol. 7, pp. 28-30.
Hongoh Y., et al., "Evaluation of Primers and PCR Conditions for the Analysis of 16s rRNA Genes from a Naturalenvironment," FEMS Microbiology Letters, 2003, vol. 221 (2), pp. 299-304.
Hood E., et al., "Chemical and Biological Weapons: New Questions, New Answers," Environmental Health Perspectives, 1999, vol. 107 (12), pp. 931-932.
Houng H.S., et al., "Rapid Type-Specific Diagnosis of Adenovirus Type 4 Infection Using a Hexon-Based Quantitative Fluorogenic PCR," Diagnostic Microbiology and Infectious Disease, 2002, vol. 42 (4), pp. 227-236.
Howell N., et al., "Persistent Heteroplasmy of a Mutation in the Human mtDNA Control Region: Hypermutation as an Apparent

(56) References Cited

OTHER PUBLICATIONS

Consequence of Simple-Repeat Expansion/Contraction," American Journal of Human Genetics, 2000, vol. 66 (5), pp. 1589-1598.
Huber C.G., et al., "On-Line Cation Exchange for Suppression of Adduct Formation in Negative-Ion Electrospray Mass Spectrometry of Nucleic Acids," Analytical Chemistry, 1998, vol. 70 (24), pp. 5288-5295.
Huletsky A., et al., "New Real-Time PCR Assay for Rapid Detection of Methicillin-Resistant*staphylococcus aureus* Directly from Specimens Containing a Mixture of *Staphylococci*," Journal of Clinical Microbiology, 2004, vol. 42 (5), pp. 1875-1884.
Hunag C., et al., "Detection of Arboviral RNA Directly from Mosquito Homogenates by Reverse Transcription-Polymerase Chain Reaction," Journal of Virological Methods, 2001, vol. 94 (1-2), pp. 121-128.
Hung E.C., et al., "Detection of SARS Coronavirus RNA in the Cerebrospinal Fluid of a Patient with Severe Acute Respiratory Syndrome," Clinical Chemistry, 2003, vol. 49 (12), pp. 2108-2109.
Hurdle J.G., et al., "Analysis of Mupirocin Resistance and Fitness in *Staphylococcus aureus* by Molecular Genetic and Structural Modeling Techniques," Antimicrobial Agents and Chemotherapy, 2004, vol. 48 (11), pp. 4366-4376.
Hurst G.B., et al., "Detection of Bacterial DNA Polymerase Chain Reaction Products by Matrix-Assisted Laser Desorptionfionization Mass Spectrometry," Rapid Communications in Mass Spectrometry, 1996, vol. 10 (3), pp. 377-382.
Hurst G.B., et al., "MALDI-TOF Analysis of Polymerase Chain Reaction Products from Methanotrophic Bacteria," Analytical Chemistry, 1998, vol. 70 (13), pp. 2693-2698.
Hutchison C.A., et al., "Maternal Inheritance of Mammalian Mitochondrial DNA," Nature, 1974, vol. 251 (5475), pp. 536-538.
Hyde-Deruyscher R., et al., "Polyomavirus Early-Late Switch is not Regulated at the Level of Transcription Initiation and is associated with changes in RNA Processing," Proceedings of the National Academy of Sciences, 1988, vol. 85, pp. 8993-8997.
Ieven M., et al., "Rapid Detection of Methicillin Resistance in Coagulase-Negative *Staphylococci* by Commercially Available Fluorescence Test," Journal of Clinical Microbiology, 1995, vol. 33 (8), pp. 2183-2185.
Ihle O., et al., "Efficient Purification of DNA Fragments using a Protein Binding Membrane," Nucleic Acids Research, 2000, vol. 28 (16), pp. e76.
Inglis T.J., et al., "Rapid Genotypic Confirmation of Methicillin Resistance," Pathology, 1996, vol. 28 (3), pp. 259-261.
Ingman M., et al., "Mitochondrial Genome Variation and the Origin of Modern Humans," Nature, 2000, vol. 408 (6813), pp. 708-713.
International Preliminary Examination Report for Application No. PCT/US2002/06763, mailed on Jun. 11, 2003, 6 pages.
International Preliminary Examination Report for Application No. PCT/US2002/20336, mailed on Apr. 26, 2004, 8 pages.
International Preliminary Examination Report for Application No. PCT/US2003/09802, mailed on Apr. 8, 2005, 7 pages.
International Preliminary Examination Report for Application No. PCT/US2003/22835, mailed on Mar. 5, 2005, 4 pages.
International Preliminary Examination Report for Application No. PCT/US2003/38505, mailed on Mar. 3, 2006, 5 pages.
International Preliminary Examination Report for Application No. PCT/US2003/38757, mailed on Feb. 2, 2007, 5 pages.
International Preliminary Examination Report for Application No. PCT/US2003/38761, mailed on Jun. 27, 2006, 6 pages.
International Preliminary Report on Patentability and Written Opinion for Application No. PCT/US04/007236, mailed on Mar. 16, 2006, 7 pages.
International Preliminary Report on Patentability and Written Opinion for Application No. PCT/US2005/00386, mailed on Jul. 10, 2006, 6 pages.
International Preliminary Report on Patentability and Written Opinion for Application No. PCT/US2005/030058, mailed on Sep. 25, 2007, 6 pages.
International Preliminary Report on Patentability and Written Opinion for Application No. PCT/US2005/033707, mailed on Mar. 20, 2007, 6 pages.
International Preliminary Report on Patentability for Application No. PCT/US2004/033742, mailed on Jun. 20, 2006, 1 page.
International Preliminary Report on Patentability for Application No. PCT/US2005/005168, mailed on Mar. 13, 2007, 1 page.
International Preliminary Report on Patentability for Application No. PCT/US2005/018031, mailed on Nov. 29, 2006, 1 page.
International Preliminary Report on Patentability for Application No. PCT/US2006/028397, mailed on Jan. 22, 2008, 1 page.
International Preliminary Report on Patentability for Application No. PCT/US2008/054926, mailed on Aug. 26, 2009, 1 page.
International Preliminary Report on Patentability, Written Opinion and International Search Report for Application No. PCT/US2004/015123, mailed on Oct. 3, 2005, 8 pages.
International Search Report and Written Opinion for Application No. PCT/US2005/005168, mailed on Feb. 26, 2007, 7 pages.
International Search Report and Written Opinion for Application No. PCT/US2005/018031, mailed on Jun. 28, 2006, 14 pages.
International Search Report and Written Opinion for Application No. PCT/US2006/007747, mailed on Sep. 5, 2006, 13 pages.
International Search Report and Written Opinion for Application No. PCT/US2006/015160, mailed on Oct. 10, 2006, 13 pages.
International Search Report and Written Opinion for Application No. PCT/US2006/028397, mailed on Mar. 5, 2007, 14 pages.
International Search Report and Written Opinion for Application No. PCT/US2006/040747, mailed on Mar. 17, 2009, 19 pages.
International Search Report and Written Opinion for Application No. PCT/US2006/061307, mailed on Jan. 9, 2008, 21 pages.
International Search Report and Written Opinion for Application No. PCT/US2007/020045 mailed on Jan. 8, 2009, 17 pages.
International Search Report and Written Opinion for Application No. PCT/US2008/054926, mailed on Jan. 26, 2009, 15 pages.
International Search Report and Written Opinion for Application No. PCT/US2008/057901, mailed on Aug. 28, 2008, 14 pages.
International Search Report and Written Opinion for Application No. PCT/US2008/064891, mailed on Jun. 29, 2009, 15 pages.
International Search Report for Application No. PCT/US04/007236, mailed on Feb. 24, 2006, 2 pages.
International Search Report for Application No. PCT/US2002/06763, mailed on Oct. 23, 2002, 2 pages.
International Search Report for Application No. PCT/US2002/20336, mailed on Feb. 3, 2003, 4 pages.
International Search Report for Application No. PCT/US2003/009802, mailed on Aug. 3, 2004, 2 pages.
International Search Report for Application No. PCT/US2003/038505, mailed on Apr. 12, 2005, 2 pages.
International Search Report for Application No. PCT/US2003/038830, mailed on Aug. 25, 2004, 4 pages.
International Search Report for Application No. PCT/US2003/22835, mailed on Dec. 12, 2003, 1 page.
International Search Report for Application No. PCT/US2003/38757, mailed on Jun. 24, 2004, 2 pages.
International Search Report for Application No. PCT/US2003/38761, mailed on Dec. 30, 2005, 5 pages.
International Search Report for Application No. PCT/US2003/38795, mailed on Apr. 19, 2004, 3 pages.
International Search Report for Application No. PCT/US2004/011877, mailed on Apr. 20, 2006, 4 pages.
International Search Report for Application No. PCT/US2004/012671, mailed on Sep. 28, 2007, 2 pages.
International Search Report for Application No. PCT/US2004/015196, mailed on Jul. 1, 2005, 3 pages.
International Search Report for Application No. PCT/US2004/028869, mailed on Jul. 17, 2006, 4 pages.
International Search Report for Application No. PCT/US2004/033742, mailed on May 15, 2006, 2 pages.
International Search Report for Application No. PCT/US2005/000386, mailed on May 9, 2006, 3 pages.
International Search Report for Application No. PCT/US2005/005356, mailed on Aug. 7, 2007, 4 pages.

(56) References Cited

OTHER PUBLICATIONS

International Search Report for Application No. PCT/US2005/006133, mailed on Jul. 26, 2007, 4 pages.
International Search Report for Application No. PCT/US2005/007022, mailed on Oct. 20, 2006, 1 page.
International Search Report for Application No. PCT/US2005/009557, mailed on Sep. 19, 2005, 1 page.
International Search Report for Application No. PCT/US2005/018337, mailed on Oct. 10, 2006, 2 pages.
International Search Report for Application No. PCT/US2005/024799, mailed on Dec. 28, 2006, 4 pages.
International Search Report for Application No. PCT/US2005/030058, mailed on Aug. 20, 2007, 1 page.
International Search Report for Application No. PCT/US2005/033707, mailed on Feb. 6, 2006, 3 pages.
International Search Report for Application No. PCT/US2007/066194, mailed on Jan. 15, 2008, 4 pages.
International Search Report for Application No. PCT/US2008/057717, mailed on Jan. 13, 2009, 5 pages.
International Search Report for Application No. PCT/US2008/057901, mailed on Jun. 29, 2009, 15 pages.
International Search Report for Application No. PCT/US2008/065332, mailed on Nov. 28, 2008, 4 pages.
International Search Report for Application No. PCT/US2009/045635, mailed on Oct. 7, 2009, 9 pages.
Inyaku K., et al., "Rapid Detection and Identification of Mycobacteria in Sputum Samples by NestedPolymerase Chain Reaction and Restriction Fragment Length Polymorphisms of dnaJ Heat Shock Protein Gene," Journal of Medical Sciences, 1993, vol. 42 (1), pp. 21-31.
Iqbal S.S., et al., "A Review of Molecular Recognition Technologies for Detection of Biological Threat Agents," Biosensors & Bioelectronics, 2000, vol. 15 (11-12), pp. 549-578.
Isola N. R., et al., "MALDI-TOF Mass Spectrometric Method for Detection of Hybridized DNA Oligomers," Analytical Chemistry, 2001, vol. 73 (9), pp. 2126-2131.
Iteman I., et al., "Comparison of Conserved Structural and Regulatory Domains within Divergent 16S rRNA-235 rRNA Spacer Sequences of Cyanobacteria," Microbiology, 2000, vol. 146 (Pt 6), pp. 1275-1286.
Ito T., et al., "Insights on Antibiotic Resistance of *Staphylococcus aureus* from its Whole Genome: Genomic Island Scc," Drug Resistance Updates, 2003, vol. 6 (1), pp. 41-52.
Ito T., et al., "Structural Comparison of Three Types of *Staphylococcal cassette* Chromosome mecIntegrated in the Chromosome in Methicillin-Resistant *Staphylococcus aureus*," Antimicrobial Agents and Chemotherapy, 2001, vol. 45 (5), pp. 1323-1336.
Jackson P.E., et al., "Mass Spectrometry for Genotyping: an Emerging Tool for Molecular Medicine," Molecular Medicine Today, 2000, vol. 6 (7), pp. 271-276.
James A.M., et al., "Borelia Lonestari Infection after a Bite by an Amblyomma Americanum Tick," The Journal of Infectious Diseases, 2001, vol. 183 (12), pp. 1810-1814.
Jankowski K., et al., "Mass Spectrometry of DNA. Part 2 Quantitative Estimation of Base Composition," European Journal of Mass Spectrometry, 1980, vol. 1 (1), pp. 45-52.
Jansen R.C., et al., "Genotype-by-environment Interaction in Genetic Mapping of Multiple Quantitative Trait Loci," Theoretical and Applied Genetics, 1995, vol. 91, pp. 33-37.
Jaulhac B., et al., "Specific Detection of the Toxic Shock Syndrome Toxin-1 Gene Using the Polymerase Chain Reaction," Molecular and Cellular Probes, 1991, vol. 5, pp. 281-284.
Jaulhac B., et al., "Synthetic DNA Probes for Detection of Genes for Enterotoxins A, B, C, D, E and for Tsst-1 in *Staphylococcal* Strains," Journal of Applied Bacterial, 1992, vol. 72 (5), pp. 386-392.
Jensen M.A., et al., "Rapid Identification of Bacteria on the Basis of Polymcrase Chain Reaction-Amplified Ribosomal DNA Spacer Polymorphisms," Applied and Environmental Microbiology, 1993, vol. 59 (4), pp. 945-952.

Jeong J., et al., "Early Screening of Oxacillin-Resistant *Staphylococcus aureus* and *Staphylococcus epidermidis* from Blood Culture," Journal of Korean Medical Science, 2002, vol. 17, pp. 168-172.
Jiang C., et al., "Multiple Trait Analysis of Genetic Mapping for Quantitative Trait Loci Genetics," Genetics, 1995, vol. 140 (3), pp. 1111-1127.
Jiang Y., et al., "A Highly Efficient and Automated Method for Purifying and Desalting PCR Products for Analysis by Electrospray Ionization Mass Spectrometry," Analytical Biochemistry, 2003, vol. 316 (1), pp. 50-57.
Johansson A., et al., "Evaluation of PCR-based Methods for Discrimination of *Francisella* species and Subspecies and Development of a Specific PCR that Distinguishes the Two Major Subspecies of *Francisella tularensis*," Journal of Clinical Microbiology, 2000, vol. 38 (11), pp. 4180-4185.
Johnson W.M., et al., "Detection of Genes for Enterotoxins, Exfoliative Toxins, and Toxic Shock Syndrome Toxin 1 in *Staphylococcus aureus* by the Polymerase Chain Reaction," Journal of Clinical Microbiology, 1991, vol. 29 (3), pp. 426-430.
Johnson Y.A., et al., "Precise Molecular Weight Determination of PCR Products of the rRNA Intergenic Spacer Region Using Electrospray Quadrupole Mass Spectrometry for Differentiation of *B. subtilis* and *B. atrophaeus*, Closely Related Species of *Bacilli*," Journal of Microbiological Methods, 2000, vol. 40 (3), pp. 241-254.
Jonas D., et al., "Rapid PCR-Based Identification of Methicillin-Resistant *Staphylococcus aureus* from Screening Swabs," Journal of Clinical Microbiology, 2002, vol. 40 (5), pp. 1821-1823.
Jurinke C., et al., "Application of Nested PCR and Mass Spectrometry for DNA Based Virus Detection: HBV-DNA Detected in the Majority of Isolated Anti-Hbc Positive Sera," Genetic Analysis: Biomolecular Engineering, 1998, vol. 14 (3), pp. 97-102.
Jurinke C., et al., "Detection of Hepatitis B: Virus DNA in Serum Samples Via Nested PCR and MALDI-TOF Mass Spectrometry," Genetic Analysis: Biomolecular Engineering, 1996, vol. 13 (3), pp. 67-71.
Jurinke C., et al., "MALDI-TOF Mass Spectrometry. A Versatile Tool for High-Performance DNA Analysis," Molecular Biotechnology, 2004, vol. 26 (2), pp. 147-163.
Kacian D.L., et al., "A Replicating RNA Molecule Suitable for a Detailed Analysis of Extracellular Evolution and Replication," Proceeding of the National Academy of Sciences, 1972, vol. 69 (10), pp. 3038-3042.
Kageyama A., et al. "Rapid Detection of Human Fecal *Eubacterium* Species and Related Genera by Tested PCR Method," Journal of Microbiology, Immunology, 2001, vol. 45 (4), pp. 315-318.
Kajon A.E., et al., "Genome Type Analysis of Brazilian Adenovirus Strains of Serotypes 1, 2, 3, 5,and 7 Collected Between 1976 and 1995," Journal of Medical, 1999, vol. 58 (4), pp. 408-412.
Kasai H., et al., "Construction of the gyrB Database for the Identification and Classification of Bacteria," Genome Informatics. Workshop on Genome Informatics, 1998, pp. 13-21.
Katano H., et al., "Identification of Adeno-Associated Virus Contamination in Cell and Virus Stocks by PCR," Biotechniques, 2004, vol. 36 (4), pp. 676-680.
Katayama Y., et al., "Genetic Organization of the Chromosome Region Surrounding mecA inClinical *Staphylococcal* Strains: Role of IS431-Mediated mecI Deletion in Expression of Resistance inmed-Canying, Low-Level Methicillin-Resistant *Staphylococcus haemolyticus*," Antimicrobial Agents and Chemotherapy, 2001, vol. 45 (7), pp. 1955-1963.
Ke D., et al., "Development of a PCR Assay for Rapid Detection of Enterococci," Journal of Clinical Microbiology, 1999, vol. 37 (11), pp. 3497-3503.
Kearns A.M., et al., "Rapid Detection of Methicillin-Resistant *Staphylococci* by Multiplex PCR," The Journal of Hospital Inspection, 1999, vol. 43 (1), pp. 33-37.
Keller A., et al., "Empirical Statistical Model to Estimate the Accuracy of Peptide Identifications Made by MS/MS and Database Search," Analytical Chemistry, 2002, vol. 74 (20), pp. 5383-5392.

(56) References Cited

OTHER PUBLICATIONS

Khan A.S., et al., "An Outbreak of Crimean-Congo Haemorrhagic Fever in the United Arab Emirates, 1994-1995," The American Journal of Tropical Medicine and Hygiene, 1997, vol. 57 (5), pp. 519-525.

Khan S.A., et al., "Simultaneous Detection of Erythromycin-Resistant Methylase Genes ermA and ermC from *Staphylococcus* Spp. by Multiplex-PCR," Molecular and Cellular Probes, 1999, vol. 13 (5), pp. 381-387.

Kidd A.H., et al., "Rapid Subgenus Identification of Human Adenovirus Isolates by a General PCR," Journal of Clinical Microbiology, 1996, vol. 34 (3), pp. 622-627.

Kidd-Ljunggren K., et al., "The Hepatitis B Virus X Gene: Analysis of Functional Domain Variation and Gene Phylogeny using Multiple Sequences," Journal of General Virology, 1995, vol. 76 (pt 9), pp. 2119-2130.

Kikuchi K., et al., "Restriction Fragment Length Polymorphism Analysis of Clinical Isolates of Mycobacterium Haemophilum," Journal of Clinical Microbiology, 1994, vol. 32 (7), pp. 1763-1767.

Kilbourne E.D., "Influenza Pandemics: Can We Prepare for the Unpredictable," Viral Immunology, 2004, vol. 17 (3), pp. 350-357.

Kilbourne E.D., "Influenza Pandemics of the 20th Century," Emerging Infectious Diseases Journal, 2006, vol. 12 (1), pp. 9-14.

Kilpatrick D.R., et al., "Group-Specific Identification of Polioviruses by PCR Using Primer Containing Mixed-Base or Deoxyinosine Residues at Positions of Codon Degeneracy," Journal of Clinical Microbiology, 1996, vol. 34 (12), pp. 2990-2996.

Kim B.J., et al., "Identification of Mycobacterial Species by Comparative Sequence Analysis of the RNA Polymerase Gene (rpoB)," Journal of Clinical Microbiology, 1999, vol. 37 (6), pp. 1714-1720.

Kinney R.M., et al., "Nucleotide Sequences of the 26S mRNAs of the Viruses Defining the Venezuelan Equine Encephalitis Antigenic Complex," The American Journal of Tropical Medicine and Hygiene, 1998, vol. 59 (6), pp. 952-964.

Kirpekar F., et al., "Matrix Assisted Laser Desorption/Ionization Mass Spectrometry of Enzymatically Synthesized RNA up to 150 kDa," Nucleic Acids Research, 1994, vol. 22 (19), pp. 3866-3870.

Kitagawa Y., et al., "Rapid Diagnosis of Methicillin-Resistant *Staphylococcus aureus* Bacteremia by Nested Polymerase Chain Reaction," Annals of Surgery, 1996, vol. 224 (5), pp. 665-671.

Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.

Kolbert C.P., et al., "Branched-DNA Assay for Detection of the mecA Gene in Oxacillin-Resistant and Oxacillin-Sensitive *Staphylococci*," Journal of Clinical Microbiology, 1998, vol. 36 (9), pp. 2640-2644.

Kowalak J.A., et al., "A Novel Method for the Determination of Post-Transcriptional Modification in RNA by Mass Spectrometry," Nucleic Acids Research, 1993, vol. 21 (19), pp. 4577-4585.

Krafft A.E., et al., "Evaluation of PCR Testing of Ethanol-Fixed Nasal Swab Specimens as anAugmented Surveillance Strategy for Influenza Virus and Adenovirus Identification," Journal of Clincal Microbiology, 2005, vol. 43 (4), pp. 1768-1775.

Krahmer M.T., et al., "Electrospray Quadrupole Mass Spectrometry Analysis of Model Oligonucleotides and Polymerase Chain Reaction Products: Determination of Base Substitutions, Nucleotide Additions/Deletions, and Chemical Modifications," Analytical Chemistry, 1999, vol. 71 (14), pp. 2893-2900.

Krahmer M.T., et al, "MS for Identification of Single Nucleotide Polymorphisms and MS/MS for Discrimination of Isomeric PCR Products," Analytical Chemistry, 2000, vol. 72 (17), pp. 4033-4040.

Kramer L.D., et al., "Dection of Encephalitis Viruses in Mosquitoes (*Diptera culicidea*) and Avian Tissues," Journal of Medical Entomology, 2002, vol. 39 (2), pp. 312-323.

Kramer L.D., et al., "Dection of St. Louis Encephalitis and Western Equine Encephalomyelitis RNAin Mosquitoes Tested Without Maintainance of a Cold Chain," Journal of the American Mosquito Control Association, 2001, vol. 17 (4), pp. 213-215.

Kresken M., et al., "Prevalence of Mupirocin Resistance in Clinical Isolates of *Staphylococccus aureus* and *Staphylococcus epidermidis*: Results of the Antimicrobial Resistance Surveillance Study of the Paul-Ehrlich-Society for Chemotherapy, 2001," International Journal of Antimicrobial Agents, 2004, vol. 23 (6), pp. 577-581.

Krishnan P.U., et al., "Detection of Methicillin and Mupirocin Resistance in *Staphylococcus aureus*isolates Using Conventional and Molecular Methods: A Descriptive Study from a Burns Unit with Highprevalence of MRSA," Journal of Clinical Pathology, 2002, vol. 55 (10), pp. 745-748.

Kroes I., et al., "Bacterial Diversity Within the Human Subgingival Crevice," Proceeding of the National Academy of Sciences, 1999, vol. 96 (25), pp. 14547-14552.

Krossoy B., et al., "The Putative Polymerase Sequence of Infectious Salmon Anemia Virus Suggests a New Genus within the Orthomyxoviridae," Journal of Virology, 1999, vol. 73 (3), pp. 2136-2142.

Ksiazek T.G., et al., "A Novel Coronavirus Associated with Severe Acute Respiratory Syndrome," The New England Journal of Medicine, 2003, vol. 348 (20), pp. 1953-1966.

Kupke T., et al., "Molecular Characterization of Lantibiotic-Synthesizing Enzyme EpiD Reveals a Function for Bacterial Dfp Proteins in Coenzyme A Biosynthesis," Journal of Biological Chemistry, 2000, vol. 275 (41), pp. 31838-31846.

Kuroda M., et al., "Whole Genome Sequencing of Meticillin-Resistant *Staphylococcus aureus*," The Lancet, 2001, vol. 357 (9264), pp. 1225-1240.

Kwok S., et al., "Avoiding False Positives with PCR," Nature, 1989, vol. 339 (6221), pp. 237-238.

Labandeira-Rey, M. et al., "*Staphylococcus aureus* Panton Valentine Leukocidin CausesNecrotizing Pneumonia," ScienceExpress, 2007, 8 pages.

Lacroix J.M., et al, "PCR-Based Technique for the Detection of Bacteria in Semen and Urine," Journal of Microbiological Methods, 1996, vol. 26, pp. 61-71.

Lacroix L., et al., "Triplex Formation by Oligonucleotides Containing 5-(1-Propynyl)-2-deoxyuridine: Decreased Magnesium Dependence and Improved Intracellular Gene Targeting," Biochemistry, 1999, vol. 38 (6), pp. 1893-1901.

Laken S.J., et al., "Genotyping by Mass Spectrometric Analysis of Short DNA Fragments," Nature Biotechnology, 1998, vol. 16 (13), pp. 1352-1356.

Lamb R.A., et al., "Sequence of Interrupted and Uninterrupted mRNAs and Cloned DNA Coding for the Two Overlapping Nonstructural Proteins of Influenza Virus," Cell, 1980, vol. 21 (2), pp. 475-485.

Lambert A.J., et al., "Detection of North American Eastern and Western Equine EncephalitisViruses by Nucleic Acid Amplification Assays," Journal of Clinical Microbiology, 2003, vol. 41 (1), pp. 379-385.

Lau L.T., et al, "A Real-Time PCR for SARS-Coronavirus Incorporating Target Gene Pre-Amplification," Biochemical and Biophysical Research Communications, 2003, vol. 312 (4), pp. 1290-1296.

Lau L.T., et al., "Nucleic Acid Sequence-Based Amplification Methods to Detect Avian Influenza Virus," Biochemical and Biophysical Research Communications, 2004, vol. 313 (2), pp. 336-342.

Le Cann P., et al., "Quantification of Human Astroviruses in Sewage Using Real-Time RT-PCR," Research in Microbiology, 2004, vol. 155 (1), pp. 11-15.

Lebedev Y., et al., "Oligonucleotides Containing 2-Aminoadenine and 5-Methycytosine are More Effective as Primers for PCR Amplification than their Nonmodified Counterparts," Genetic Analysis: Biomolecular Engineering, 1996, vol. 13 (1), pp. 15-21.

Lednicky J.A., et al., "Polyomaviruses and Human Tumors: A Brief Review of Current Concenpts and Interpretations," Frontiers Bioscience, 1999, vol. 4, pp. D153-D164.

Lee J.A., et al., "Rapid Identification of Human Adenovirus Types 3 and 7 from Respiratory Specimens via Multiplex Type-Specific PCR," Journal of Clinical Microbiology, 2005, vol. 43 (11), pp. 5509-5514.

(56) References Cited

OTHER PUBLICATIONS

Lee J.H., et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," Journal of the American Mosquito Control Association, 2002, vol. 18 (1), pp. 26-31.
Leif H., et al., "Isolation and Characterization of the Proton-Translocating NADH: Ubiqu None Oxidoreductase from *Escherichia coli*," European Journal of Biochemistry, 1995, vol. 230 (2), pp. 538-548.
Lengyel A., et al., "Characterization of the Main Protein Components of Adenovirus Virion and itsPossible Use in Laboratory Diagnostics," Acta Microbiologica Immunologica Hungarica, 1998, vol. 43 (3-4), pp. 281-283.
Leroy E.M., et al., "Diagnosis of Ebola Haemorrhagic Fever by RT-PCR in an Epidemic Setting," Journal of Medicinal Virology, 2000, vol. 60 (4), pp. 463-467.
Levi K., et al., "Evaluation of an Isothermal Signal Amplification Method for Rapid Detection of Methicillin-Resistant*Staphylococcus aureus* from Patient-Screening Swabs," Journal of Clinical Microbiology, 2003, vol. 41 (7), pp. 3187-3191.
Levine S.M., et al., "PCR-Based Detection of Bacillus Anthracis in Formalin-Fixed Tissue from a Patient Receiving Ciprofloxacin," Journal of Clinical Microbiology, 2002, vol. 40 (11), pp. 4360-4362.
Levison P.R., et al., "Recent Developments of Magnetic Beads for Use in Nucleic Acid Purification," Journal of Chromatography, 1998, A816, 107-111.
Lewers K.S., et al., "Detection of Linked QTL for Soybean Brown Stem Rot Resistance in "BSR 101" as Expressed in a Growth Chamber Environment," Molecular Breeding, 1999, vol. 5, pp. 33-42.
Li C., et al., "Evolution of H9N2 Influenza Viruses from Domestic Poultry in Mainland China," Virology, 2005, vol. 340 (1), pp. 70-83.
Li J., et al., "Single Nucleotide Polymorphism Determination Using Primer Extension and Time-of-Flight Mass Spectrometry," Electrophoresis, 1999, vol. 20 (6), pp. 1258-1265.
Li Q., et al., "Screening of the High Yield Influenza B Virus on MDCK c14d Cloning of its Whole Genome," International Congress Series, 2004, vol. 1263, pp. 610-614.
Li Q., et al., "Genetic Variability of Hexon Loops 1 and 2 between Seven Genome Types of Adenovirus Serotype 7," Archives of Virology, 1999, vol. 144 (9), pp. 1739-1749.
Li Q.G., et al., "Analysis of 15 Different Genome Types of Adenovirus Type 7 Isolated on FiveContinents," Journal of Virology, 1986, vol. 60 (1), pp. 331-335.
Li Q.G., et al., "Comparison of 17 Genome Types of Adenovirus Type 3 Identified among Strains Recovered from Six Continents," Journal of Clinical Microbiology, 1988, vol. 26 (5), pp. 1009-1015.
Liebermann H., et al., "Mapping of Epitopes on the Fiber Knobs of Human Adenovirus Serotypes 8 and 15," Intervirology, 2002, vol. 45 (1), pp. 59-66.
Liebermann H., et al., "Mapping of Linear Epitopes on Fibre Knob of Human Adenovirus Serotype 5," Virus Research, 2001, vol. 73 (2), pp. 145-151.
Lim L.P., et al., "The MicroRNAs of Caenorhabditis Elegans," Genes and Development, 2003, vol. 17 (8), pp. 991-1008.
Limbach P.A., et al., "Enzymatic Sequencing of Oligonucleotides with Electrospray Mass Spectrometry," 42nd ASMS Conference on Mass Spectrometry, 1994.
Limoncu M.H., et al., "Emergence of Phenotypic Resistance to Ciprofloxacin and Levofloxacin Inmethicillin-Resistant and Methicillin-Sensitive *Staphylococcus aureus* Strains," International Journal of Antimicrobial Agents, 2003, vol. 21 (5), pp. 420-424.
Lin B., et al., "Use of Oligonucleotide Microarrays for Rapid Detection and Serotyping of Acute Respiratory Disease-Associated Adenoviruses," Journal of Clinical Microbiology, 2004, vol. 42 (7), pp. 3232-3239.
Lin P.H., et al., "Oxidative Damage to Mitochondrial DNA in Atrial Muscle of Patients with Atrial Fibrillation," Free Radical Biology and Medicine, 2003, vol. 35 (10), pp. 1310-1318.

Lina G., et al., "Bacterial Competition for Human Nasal Cavity Colonization: Role of *Staphylococcal agr* Alleles," Applied and Environmental Microbiology, 2003, vol. 69 (1), pp. 18-23.
Lina G., et al., "Involvement of Panton-Valentine Leukocidin-Producing *Staphylococcus aureus* in Primary Skin Infections and Pneumonia," Clinical Infectious Diseases, 1999, vol. 29 (5), pp. 1128-1132.
Linssen B., et al., "Development of Reverse Transcription-PCR Assays Specific for Detection of Equine Encephalitis Viruses," Journal of Clinical Microbiology, 2000, vol. 38 (4), pp. 1527-1535.
Little D.P., et al., "MALDI on a Chip: Analysis of Arrays of Low-Femtomole to Subfemtomole Quantities of Synthetic Oligonucleotides and DNA Diagnostic Products Dispensed by a Piezoelectric Pipet," Analytical Chemistry, 1997, vol. 69, pp. 4540-4546.
Little D.P., et al, "Rapid Sequencing of Oligonucleotides by High-Resolution Mass Spectrometry," Journal of the American Chemical Society, 1994, vol. 116 (11), pp. 4893-4897.
Liu C., et al., "Improving the Microdialysis Procedure for Electrospray Ionization Mass Spectrometry of Biological Samples," Journal of Mass Spectrometry, 1997, vol. 32 (4), pp. 425-431.
Liu J.H., et al., "Interregional Transmission of the Internal Protein Genes of H2 Influenza Virus in Migratory Ducks from North America to Eurasia," Virus Genes, 2004, vol. 29 (1), pp. 81-86.
Liu Y., et al., "An Unusual Gene Arrangement for the Putative Chromosome Replication Origin and Circadianexpression of dnaN in *Synechococcus* sp. Strain PCC 7942," Gene, 1996, vol. 172 (1), pp. 105-109.
Livermore D.M., "The Threat from the Pink Corner," Annals of Medicine, 2003, vol. 35 (4), pp. 226-234.
Loakes D., et al., "Nitroindoles as Universal Bases," Nucleosides and Nucleotides, 1995, vol. 14 (3-5), pp. 1001-1003.
Loo J.A., et al., "Applying Charge Discrimination with Electrospray Ionization-Mass Spectrometry to Protein Analysis," Journal of American Society for Mass Spectrometry, 1995, vol. 6, pp. 1098-1104.
Lott T.J., et al., "Nucleotide Sequence Analysis of the 5-8s rDNA and Adjacent ITS2 Region of *Candidaalbicans* and Related Species," Yeast, 1993, vol. 9, pp. 1199-1206.
Louie L., et al., "Evaluation of Three Rapid Methods for Detection of Methicillin Resistance in *Staphylococcus aureus*," Journal of Clinical Microbiology, 2000, vol. 38 (6), pp. 2170-2173.
Love B.C., et al., "Cloning and Sequence of the GroESL Heat-Shock Operon of Pasteurella Multocida," Gene, 1995, vol. 166 (1), pp. 179-180.
Lovseth A., et al., "Modified Multiplex PCR Method for Detection of Pyrogenic Exotoxin Genes in *Staphylococcal* Isolates," Journal of Clinical Microbiology, 2004, vol. 42 (8), pp. 3869-3872.
Lowe T., et al., "A Computer Program for Selection of Oligonucleotide Primers for Polymerase Chain Reactions," Nucleic Acids Research, 1990, 18 (7), 1757-1761.
Lu X., et al., "Molecular Typing of Human Adenoviruses by PCR and Sequencing of a Partial Region of the Hexon Gene," Archives of Virology, 2006, vol. 151 (8), pp. 1587-1602.
Lubman D.M., Application for Continuation Grant by David Mitchell Lubman dated Jun. 4, 1996 and Jun. 14, 1996.
Lubman D.M., Application for Continuation Grant by David Mitchell Lubman dated Jun. 10, 1994 and Jun. 24, 1994.
Lubman D.M., Application for Grant by David Mitchell Lubman dated Sep. 1, 1994 and Sep. 27, 1994.
Lubman D.M., Application for Grant by David Mitchell Lubman dated Oct. 25, 1992 and Oct. 29, 1992.
Ludwig S.L., et al., "Prevalence of Antibodies to Adenovirus Serotypes 4 and 7 among Unimmunized US Army Trainees: Results of a Retrospective Nationwide Seroprevalence Survey," The Journal of Infectious Diseases, 1998, vol. 178 (6), pp. 1776-1778.
Ludwig W., et al., "Bacterial Phylogeny Based on 16S and 23S rRNA Sequence Analysis," FEMS Microbiolofy Reviews, 1994, vol. 15 (2-3), pp. 155-173.
Lukashov V.V., et al., "Evolutionary Relationships among Parvoviruses: Virus-Host Coevolution among Autonomous Primate Parvoviruses and Links between Adeno-Associated and Avian Parvoviruses," Journal of Virology, 2001, vol. 75 (6), pp. 2729-2740.

(56) References Cited

OTHER PUBLICATIONS

Ma X.X., et al., "Novel Type of Staphylococcal cassette Chromosome Mec Identified in Community-Acquired Methicillin-Resistant *Staphylococcus aureus* Strains," Antimicrobial Agents and Chemotherapy, 2002, vol. 46 (4), pp. 1147-1152.

Mack D.H., et al., "A Sensitive Method for the Identification of Uncharacterized Viruses Related to known Virus Groups: Hepadnavirus Model System," Proceedings of the National Academy of Sciences, 1988, vol. 85 (18), pp. 6977-6981.

Magnuson V.L., et al., "Substrate Nucleotide-Determined Non-Templated Addition of Adenine by Tag DNA Polymerase: Implications for PCR-Based Genotyping and Cloning," BioTechniques, 1996, vol. 21 (4), pp. 700-709.

Maiwald M., et al., "Characterization of Contaminating DNA in Taq Polymerase which Occurs During Amplification with a Primer Set for Legionella 5S Ribosomal RNA," Molecular and Cellular Probes, 1994, vol. 8 (1), pp. 11-14.

Malasig M.D., et al., "Simplified Microneutralization Test for Serotyping Adenovirus Isolates," Journal of Clinical Microbiology, 2001, vol. 39 (8), pp. 2984-2986.

Mangrum J.D., et al., "Solution Composition and Thermal Denaturation for the Production of Single-Stranded PCR Amplicons: Piperidine-Induced Destabilization of the DNA Duplex," Journal of the American Society for Mass Spectrometry, 2002, vol. 13 (3), pp. 232-240.

Manian F.A., "Asymptomatic Nasal Carriage of Mupirocin-Resistant, Methicillin-Resistant *Staphylococcus aureus* (MRSA) in a Pet Dog Associated with MRSA Infection in Household Contacts," Clinical Infectious Diseases, 2003, vol. 36 (2), pp. e26-e28.

Marks F., et al., "Genotyping of Plasmodium Falciparum Pyrimethamine Resistance by Matrix-Assisted Laser Desorption-Ionization Time-of-Flight Mass Spectrometry," Antimicrobial Agents and Chemotherapy, 2004, vol. 48 (2), pp. 466-472.

Marmur J., et al., "Strand Separation and Specific Recombination in Deoxyribonucleic Acids: Biological Studies," Proceedings of the National Academy of Sciences, 1960, vol. 46 (4), pp. 453-461.

Martemyanov K.A., et al., "Extremely Thermostable Elongation Factor (3 from Aquifer aeolicus: Cloning, Expression, Purification, and Characterization in a Heterologous Translation System," Protein Expression and Purification, 2000, vol. 18 (3), pp. 257-261.

Martineau F., et al., "Development of a PCR Assay for Identification of *Staphylococci* at Genus and Species Levels," Journal of Clinical Microbiology, 2001, vol. 39 (7), pp. 2541-2547.

Martineau F., et al., "Species-Specific and Ubiquitous-DNA-Based Assays for Rapid Identification of *Staphylococcus aureus*," Journal of Clinical Microbiology, 1998, vol. 36 (3), pp. 618-623.

Martin-Lopez J.V., et al., "Simultaneous PCR Detection of Ica Cluster and Methicillin and Mupirocinresistance Genes in Catheter-Isolated *Staphylococcus*," International Microbiology, 2004, vol. 7 (1), pp. 63-66.

Mason V.P., et al., "Diversity and linkage of Replication and Mobilisation Genes in Bacillus Rolling Irclereplicating Plasmids from Diverse Geographical Origins," FEMS Microbiology Ecology, 2002, vol. 42 (2), pp. 235-241.

Matray T.J., et al., "Synthesis and Properties of RNA Analogs-Oligoribonucleotide N3—>p5 Phosphoramidates," Nucleic Acids Research, 1999, vol. 27 (20), pp. 3976-3985.

Matsuoka M., et al., "Characteristic Expression of Three Genes, msr(A), mph(C) and erm(Y), Thatconfer Resistance to Macrolide Antibiotics on *Staphylococcus aureus*," FEMS Microbiology Letters, 2003, vol. 220 (2), pp. 287-293.

May A.C., "Percent Sequence Identity: The Need to be Explicit," Structure, 2004, vol. 12 (5), pp. 737-738.

McCabe K.M., et al., "Bacterial Species Identification After DNA Amplification with a Universal Primer Pair," Molecular Genetics and Metabolism, 1999, vol. 66 (3), pp. 205-211.

McLafferty F.W., et al., "Comparison of Algorithms and Databases for Matching Unknown Mass Spectra," Journal of the American Society for Mass Spectrometry, 1998, vol. 9 (1), pp. 92-95.

McLuckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740-747.

Mehrotra M., et al., "Multiplex PCR for Detection of Genes for *Staphylococcus aureus* Enterotoxins, Exfoliative Toxins, Toxic Shock Syndrome Toxin 1, and Methicillin Resistance," Journal of Clinical Microbiology, 2000, vol. 38 (3), pp. 1032-1035.

Meiyu F., et al., "Detection of Flaviviruses by Reverse Transcriptase-Polymerase Chain Reaction with the Universal Primer Set," Microbiology and Immunology, 1997, vol. 41 (3), pp. 209-213.

Mellor J., et al., "Genotype Dependence of Hepatitis C Virus Load Measurement in Commercially Available Quantitative Assays," Journal of Clinical Microbiology, 1999, vol. 37 (8), pp. 2525-2532.

Merlino J., et al., "New Chromogenic Identification and Detection of *Staphylococcus aureus* and Methicillin-Resistant *S. aureus*," Journal of Clinical Microbiology, 2000, vol. 38 (6), pp. 2378-2380.

Merlino J., et al., "Rapid Detection of Non-Multidrug-Resistant and Multidrug-Resistant Methicillin-Resistant *Staphylococcus aureus* Using Cycling Probe Technology for the mecA Gene," European Journal of Clinical Microbiology and Infectious Diseases, 2003, vol. 22 (5), pp. 322-323.

Messmer T.O., et al., "Discrimination of *Streptococcus pneumoniae* from Other Upper respiratory tract *Streptococci* by Arbitrary Primed PCR," Clinical Biochemistry, 1995, vol. 28 (6), pp. 567-572.

Metzgar D., et al., "PCR Analysis of Egyptian Respiratory Adenovirus Isolates, Including Identification of Species, Serotypes and Coinfections," Journal of Clinical Microbiology, 2005, vol. 43 (11), pp. 5743-5752.

Miller K.W., et al., "A Compendium of Human Mitochondria! DNA Control Region: Development of an International Standard Forensic Database," Croatian Medical Journal, 2001, vol. 42 (3), pp. 315-327.

Miragaia M., et al., "Genetic Diversity among Methicillin-Resistant *Staphylococcus epidemidis*(MRSE)," Microbial Drug Resistance, 2005, vol. 11 (2), pp. 83-93.

Miura-Ochiai R., et al., "Quantitative Detection and Rapid Identification of Human Adenoviruses," Journal of Clinical Microbiology, 2007, vol. 45 (3), pp. 958-967.

Mollet C., et al., "RpoB Sequence Analysis as a Novel Basis for Bacterial Identification," Molecular Microbiology, 1997, vol. 26 (5), pp. 1005-1011.

Monroy A.M., et al., "Exvaluation of Reverse Transcriptase Polymerase Chain Reaction for the Detection of Eastern Equine Encephalumyelitis Virus during Vector Surveillance," Journal of Medical Entomology, 1996, vol. 33 (3), pp. 449-457.

Moore C., et al., "Development and Evaluation of a Real-Time Nucleic Acid Sequence Based Amplification Assay for Rapid Detection of Influenza A," Journal of Medical Virology, 2004, vol. 74 (4), pp. 619-628.

Moricca S., et al., "Detection of *Fusarium oxysporum f.*sp. *Vasinfectum* in Cotton Tissue by Polymerase Chain Reaction," Plant Pathology, 1998, vol. 47 (4), pp. 486-494.

Morinaga N., et al., "Purification, Cloning and Charactarizarion of Variant LukE-LukD with Strong Leukocidal Activity of *Staphylococcal* Bi-Component Leukotoxin Family," Microbiology and Immunology, 2003, vol. 47 (1), pp. 81-90.

Morse R., et al., "Nucleotide Sequence of Part of the ropC Gene Encoding the B Subunit of DNA Dependent RNA Polymerase from some Gram-Positive Bacteria and Comparative Amino Acid Sequence Analysis," Systematic and Applied Microbiology, 1996, vol. 19, pp. 150-157.

Muddiman D.C., et al., "Application of Secondary Ion and Matrix-Assisted Laser Desorption-Ionization Time-of-Flight Mass Spectrometry for the Quantitative Analysis of Biological Molecules," Mass Spectrometry Reviews, 1995, vol. 14 (6), pp. 383-429.

Muddiman D.C., et al., "Characterization of PCR Products from Bacilli Using Electrospray Ionization FTICR Mass Spectrometry," Analytical Chemistry, 1996, vol. 68 (21), pp. 3705-3712.

Muddiman D.C., et al., "Sequencing and Characterization of Larger Oligonucleotides by Electrospray Ionization Fourier Transform Ion

(56) References Cited

OTHER PUBLICATIONS

Cyclotron Resonance Mass Spectrometry," Reviews in Analytical Chemistry, 1998, vol. 17 (1), pp. 1-68.
Muddiman D.C., et al., "Important Aspects Concerning the Quantification of Biomolecules by Time-of-Flight Secondaryion Mass Spectrometry," Applied Spectrometry, 1996, vol. 50 (2), pp. 161-166.
Muddiman D.C., et al., "Length and Base Composition of PCR-Amplified Nucleic Acids Using Mass Measurements from Electrospray Ionization Mass Spectrometry," Analytical Chemistry, 1997, vol. 69 (8), pp. 1543-1549.
Muddiman D.C., et al., "Precise Mass Measurement of a Double-Stranded 500 Base-Pair (309 kDa) Polymerase Chain Reaction Product by Negative Ion Electrospray Ionization Fourier Transform Ion Cyclotron Resonance Mass Spectrometry," Rapid Communications in Mass Spectrometry, 1999, vol. 13 (2), pp. 1201-1204.
Muhammed W.T., et al., "Electrospray Ionization Quadrupole Time-of-Flight Mass Spectrometry and Guadrupole Mass Spectrometry for Genotyping Single Nucleotide Substitutions in Intact Polymerase Chain Reaction Products in K-Ras and p53," Rapid Communications in Mass Spectrometry, 2002, vol. 16 (24), pp. 2278-2285.
Murakami K., et al., "Identification of Methicillin-Resistant Strains of *Staphylococci* by Polymerase Chain Reaction," Journal of Clinical Microbiology, 1991, vol. 29 (10), pp. 2240-2244.
Mushegian A.R., et al., "A Minimal Gene Set for Cellular Life Derived by Comparison of Complete Bacterial Genomes," Proceedings of the National Academy of Science, 1996, vol. 93 (19), pp. 10268-10273.
Na B.K., et al., "Detection and Typing of Respiratory Adenoviruses in a Single-Tube Multiplex Polymerase Chain Reaction," Journal of Medical Virology, 2002, vol. 66 (4), pp. 512-517.
Nagpal M.L., et al., "Utility of 16S-23S rRNA Spacer Region Methodology: How Similar are Interspace Regions within a Genome and Between Strains for Closely Related Organisms", Journal of Microbiological Methods, 1998, vol. 33, pp. 211-219.
Nagy M., et al., "Sequence Analysis of Porcine Adenovirus Serotype 5 Fibre Gene: Evidence for Recombination," Virus Genes, 2002, vol. 24 (2), pp. 181-185.
Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.
Nakagawa S., et al., "Gene Sequences and Specific Detection for Panton-Valentine Leukocidin," Biochemical and Biophysical Research Communications, 2005, vol. 328 (4), pp. 995-1002.
Nakao H., et al., "Development of a Direct PCR Assay for Detection of the Diphtheria Toxin Gene," Journal of Clinical Microbiology, 1997, vol. 35 (7), pp. 1651-1655.
Narita S., et al., "Phage Conversion of Panton-Valentine Leukocidin in *Staphylococcus aureus*: Molecular Analysis of a PVL-Converting Phage, cpSLT," Gene, 2001, vol. 268 (1-2), pp. 195-206.
Naumov G.I., et al., "Discrimination Between the Soil Yeast Species *Williopsis saturnus* and *Williopsis suaveolens* by the Polymerase Chain Reaction with the Universal Primer N21," Microbiology, 2000, vol. 69 (2), pp. 229-233.
NEB Catalog, 1998/1999, pp. 1, 79, 121 and 284.
Neumann G., et al., "Host Range Restriction and Pathogenicity in the Context of Influenza Pandemic," Emerging Infectious Diseases, 2006, vol. 12 (6), pp. 881-886.
Newcombe J., et al., "PCR of Peripheral Blood for Diagnosis of Meningococcal Disease," Journal of Clinical Microbiology, 1996, vol. 34 (7), pp. 1637-1640.
Ng E.K., et al., "Serial Analysis of the Plasma Concentration of SARS Coronavirus RNA in Pediatric Patients with Severe Acute Respiratory Syndrome," Clinical Chemistry, 2003, vol. 49 (12), pp. 2085-2088.

Ng E.K., et al., "Quantitative Analysis an Prognostic Implication of SARS Coronavirus RNA in the Plasma and Serum of Patients with Severe Acute Respiratory Syndrome," Clinical Chemistry, 2003, vol. 49 (12), pp. 1976-1980.
Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.
Nilsson M., et al., "Evaluation of Mitochondrial DNA Coding Region Assays for Increased Discrimination in Forensic Analysis," Forensic Science International: Genetics, 2008, vol. 2 (1), pp. 1-8.
Nishikawa T., et al., "Reconstitution of Active Recombinant Ship Toxin (Stc)1 from Recombinant Stxl-A and Sbtl-B Subunits Independently Produced by *E. coli* Clones," FEMS Microbiol Letters, 1999, vol. 178 (1), pp. 13-18.
Non-Final Office Action mailed Feb. 2, 2007 for U.S. Appl. No. 10/844,938, filed May 12, 2004.
Non-Final Office Action mailed Oct. 2, 2009 for U.S. Appl. No. 11/929,707, filed Oct. 30, 2007.
Non-Final Office Action mailed Aug. 4, 2010 for U.S. Appl. No. 12/049,949, filed Mar. 17, 2008.
Non-Final Office Action mailed Apr. 6, 2009 for U.S. Appl. No. 11/331,987, filed Jan. 13, 2006.
Non-Final Office Action mailed Apr. 7, 2006 for U.S. Appl. No. 10/964,571, filed Oct. 12, 2004.
Non-Final Office Action mailed Aug. 7, 2007 for U.S. Appl. No. 10/844,938, filed May 12, 2004.
Non-Final Office Action mailed Jun. 10, 2009 for U.S. Appl. No. 10/844,938, filed May 12, 2004.
Non-Final Office Action mailed Jan. 12, 2010 for U.S. Appl. No. 11/491,376, filed Jul. 21, 2006.
Non-Final Office Action mailed Oct. 13, 2010 for U.S. Appl. No. 10/754,415, filed Jan. 9, 2004.
Non-Final Office Action mailed Sep. 16, 2009 for U.S. Appl. No. 11/233,630, filed Sep. 21, 2005.
Non-Final Office Action mailed Apr. 17, 2009 for U.S. Appl. No. 12/211,641, filed Sep. 16, 2008.
Non-Final Office Action mailed Nov. 19, 2003 for U.S. Appl. No. 09/798,007, filed Mar. 2, 2001.
Non-Final Office Action mailed Aug. 20, 2007 for U.S. Appl. No. 11/582,863, filed Oct. 17, 2006.
Non-Final Office Action mailed Jun. 20, 2007 for U.S. Appl. No. 11/136,134, filed May 24, 2005.
Non-Final Office Action mailed May 20, 2008 for U.S. Appl. No. 10/844,938, filed May 12, 2004.
Non-Final Office Action mailed Oct. 20, 2004 for U.S. Appl. No. 09/891,793, filed Jun. 26, 2001.
Non-Final Office Action mailed Feb. 23, 2009 for U.S. Appl. No. 10/660,122, filed Sep. 11, 2003.
Non-Final Office Action mailed Jul. 26, 2013 for U.S. Appl. No. 13/447,678, filed Apr. 16, 2012.
Non-Final Office Action mailed Mar. 26, 2008 for U.S. Appl. No. 11/136,134, filed May 24, 2005.
Non-Final Office Action mailed May 26, 2010 for U.S. Appl. No. 11/869,449, filed Oct. 9, 2007.
Non-Final Office Action mailed Jul. 27, 2006 for U.S. Appl. No. 11/209,439, filed Aug. 8, 2005.
Non-Final Office Action mailed Oct. 27, 2011 for U.S. Appl. No. 12/684,742, filed Jan. 8, 2010.
Non-Final Office Action mailed Jun. 28, 2010 for U.S. Appl. No. 11/930,002, filed Oct. 30, 2007.
Non-Final Office Action mailed Sep. 28, 2009 for U.S. Appl. No. 11/930,017, filed Oct. 30, 2007.
Non-Final Office Action mailed Dec. 29, 2010 for U.S. Appl. No. 12/616,422, filed Nov. 11, 2009.
Non-Final Office Action mailed Apr. 30, 2010 for U.S. Appl. No. 11/930,108, filed Oct. 31, 2007.
Norder H., et al., "Typing of Hepatitis B Virus Genomes by a Simplified Polymerase Chain Reaction," Journal of Medical Virology, 1990, vol. 31 (3), pp. 215-221.
Nordhoff E., et al., "Matrix Assisted Laser Desorption/Ionization Mass Spectrometry of Nucleic Acids with Wavelengths in the

(56) References Cited

OTHER PUBLICATIONS

Ultraviolet and Infrared," Rapid Communications in Mass Spectrometry, 1992, vol. 6 (12), pp. 771-776.
Notice of Allowance mailed Apr. 1, 2011 for U.S. Appl. No. 11/233,630, filed Sep. 21, 2005.
Notice of Allowance mailed Jun. 3, 2009 for U.S. Appl. No. 11/331,978, filed Jan. 13, 2006.
Notice of Allowance mailed Aug. 5, 2010 for U.S. Appl. No. 11/233,630, filed Sep. 21, 2005.
Notice of Allowance mailed Aug. 6, 2009 for U.S. Appl. No. 10/728,486, filed Dec. 5, 2003.
Notice of Allowance mailed Jun. 9, 2011 for U.S. Appl. No. 11/331,987, filed Jan. 13, 2006.
Notice of Allowance mailed Jun. 9, 2011 for U.S. Appl. No. 11/491,376, filed Jul. 21, 2006.
Notice of Allowance mailed Dec. 10, 2010 for U.S. Appl. No. 11/233,630, filed Sep. 21, 2005.
Notice of Allowance mailed Dec. 10, 2010 for U.S. Appl. No. 11/491,376, filed Jul. 21, 2006.
Notice of Allowance mailed Feb. 12, 2009 for U.S. Appl. No. 11/136,134, filed May 24, 2005.
Notice of Allowance mailed Nov. 12, 2009 for U.S. Appl. No. 10/728,486, filed Dec. 5, 2003.
Notice of Allowance mailed Dec. 15, 2008 for U.S. Appl. No. 11/331,978, filed Jan. 13, 2006.
Notice of Allowance mailed Mar. 15, 2012 for U.S. Appl. No. 12/684,742, filed Jan. 8, 2010.
Notice of Allowance mailed Sep. 18, 2009 for U.S. Appl. No. 10/660,998, filed Sep. 12, 2003.
Notice of Allowance mailed May 21, 2009 for U.S. Appl. No. 11/136,134, filed May 24, 2005.
Notice of Allowance mailed Nov. 24, 2009 for U.S. Appl. No. 11/331,978, filed Jan. 13, 2006.
Notice of Allowance mailed May 25, 2011 for U.S. Appl. No. 11/929,707, filed Oct. 30, 2007.
Notice of Allowance mailed Oct. 29, 2009 for U.S. Appl. No. 10/660,122, filed Sep. 11, 2003.
Notice of Allowance mailed Oct. 31, 2008 for U.S. Appl. No. 11/136,134, filed May 24, 2005.
Nubel U., et al., "PCR Primers to Amplify 16S rRNA Genes from Cyanobacteria," Applied and Environmental Microbiology, 1997, vol. 63 (8), pp. 3327-3332.
Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.
Null A.P., et al., "Determination of a Correction to Improve Mass Measurement Accuracy of Isotopically Unresolved Polymerase Chain Reaction Amplicons by Electrospray Ionization Fourier Transform Ion Cyclotron Resonance Mass Spectrometry," Rapid Communications in Mass Spectrometry, 2003, vol. 17 (15), pp. 1714-1722.
Null A.P., et al., "Evaluation of Sample Preparation Techniques for Mass Measurements of PCR Products Using ESIFT—ICR Mass Spectrometry," The American Society for Mass Spectrometry, 2002, vol. 13 (4), pp. 338-344.
Null A.P., et al., "Genotyping of Simple and Compound Short Tandem Repeat Loci Using Electrospray Ionization Fourier Transform Ion Cyclotron Resonance Mass Spectrometry," Analytical Chemistry, 2001, vol. 73 (18), pp. 4514-4521.
Null A.P., et al., "Implications of Hydrophobicity and Free Energy of Solvation for Characterization of Nucleic Acids by Electrospray Ionization Mass Spectrometry," Analytical Chemistry, 2003, vol. 75 (6), pp. 1331-1339.
Null A.P., et al., "Perspectives on the Use of Electrospray Ionization Fourier Transform Ion Cyclotron Resonance Mass Spectrometry for Short Tandem Repeat Genotyping in the Post Genome Era," Journal of Mass Spectrometry, 2001, vol. 36 (6), pp. 589-606.
Null A.P., et al., "Preparation of Single-Stranded PCR Products for Electrospray Ionization Mass Spectrometry Using the DNA Repair Enzyme Lambda Exonuclease," Analyst, 2000, vol. 125 (4), pp. 619-626.
Nunes E.L., et al., "Detection of IleS-2 Gene Encoding Mupirocin Resistance in Methicillin-Resistant *Staphylococcus aureus* by Multiplex PCR," Diagnostic Microbiology and Infectious Disease, 1999, vol. 34 (2), pp. 77-81.
Nygren M., et al., "Quantification of HIV-1 Using Multiple Quantitative Polymerase Chain Reaction Standards and Bioluminometric Detection," Analytical Biochemistry, 2001, vol. 288 (1), pp. 28-38.
Oberacher H., et al., "Analysis of Polymerase Chain Reaction Products by On-Line Liquid Chromatography Mass Spectrometry for Genotyping of Polymeric Short tandem Repeat Loci," Analytical Chemistry, 2001, vol. 73 (21), pp. 5109-5115.
Oberacher H., et al., "Increased Foresnic Efficiency of DNA Fingerprints Through Simultaneous Resolution of Length and Nucleotide Variability by High-Performance Mass Spectrometry," Human Mutation, 2008, vol. 29 (3), pp. 427-432.
Oberste M.S., et al., "Improved Molecular Identification of Enteroviruses by RT-PCR and Amplicon Sequencing," Journal of Clinical Virology, 2003, vol. 26 (3), pp. 375-377.
Oberste M.S., et al., "Molecular Epidemiology and Type-Specific Detection of Echovirus 11 Isolates from the Americas, Europe, Africa, Australia, Southern Asia and the Middle East," Virus Research, 2003, vol. 91 (2), pp. 241-248.
Oberste M.S., et al., "Molecular Phylogeny and Proposed Classification of the Simian Picornaviruses," Journal of Virology, 2002, vol. 76 (3), pp. 1244-1251.
Office Action mailed Apr. 1, 2004 for U.S. Appl. No. 10/156,608, filed May 24, 2002.
Office Action mailed Jul. 1, 2008 for U.S. Appl. No. 10/418,514, filed Apr. 18, 2003.
Office Action mailed May 1, 2006 for U.S. Appl. No. 10/660,998, filed Sep. 12, 2003.
Office Action mailed Feb. 2, 2011 for U.S. Appl. No. 11/869,449, filed Oct. 9, 2007.
Office Action mailed Jan. 2, 2009 for U.S. Appl. No. 11/060,135, filed Feb. 17, 2005.
Office Action mailed Jul. 2, 2009 for U.S. Appl. No. 11/582,930, filed Oct. 17, 2006.
Office Action mailed Jun. 2, 2006 for U.S. Appl. No. 10/933,928, filed Sep. 3, 2004.
Office Action mailed Jun. 2, 2008 for U.S. Appl. No. 11/331,978, filed Jan. 13, 2006.
Office Action mailed May 2, 2008 for U.S. Appl. No. 11/582,930, filed Oct. 17, 2006.
Office Action mailed Oct. 2, 2008 for U.S. Appl. No. 11/233,630, filed Sep. 21, 2005.
Office Action mailed Oct. 2, 2009 for Japanese Application No. 2005508560 filed Dec. 5, 2003.
Office Action mailed Aug. 3, 2006 for U.S. Appl. No. 10/660,998, filed Sep. 12, 2003.
Office Action mailed Aug. 3, 2009 for U.S. Appl. No. 11/754,174, filed May 25, 2007.
Office Action mailed Dec. 3, 2003 for U.S. Appl. No. 10/325,527, filed Dec. 18, 2002.
Office Action mailed Feb. 3, 2011 for U.S. Appl. No. 12/326,800, filed Dec. 2, 2008.
Office Action mailed Nov. 3, 2008 for U.S. Appl. No. 10/728,486, filed Dec. 5, 2003.
Office Action mailed Apr. 4, 2008 for U.S. Appl. No. 10/829,826, filed Apr. 22, 2004.
Office Action mailed Dec. 4, 2006 for Indian Application No. 1136KOLNP2003 filed Mar. 4, 2002.
Office Action mailed Feb. 4, 2009 for U.S. Appl. No. 11/404,561, filed Apr. 12, 2006.
Office Action mailed Jun. 4, 2009 for U.S. Appl. No. 10/754,415, filed Jan. 9, 2004.
Office Action mailed May 4, 2010 for U.S. Appl. No. 90/010,447, filed Apr. 9, 2009.
Office Action mailed May 4, 2010 for U.S. Appl. No. 90/010,448, filed Apr. 9, 2009.

(56) References Cited

OTHER PUBLICATIONS

Office Action mailed Nov. 4, 2009 for European Application No. 02709785.6 filed Mar. 4, 2002.
Office Action mailed Sep. 4, 2008 for Australian Application No. 2003297687 filed Dec. 5, 2003.
Office Action mailed Aug. 5, 2010 for European Application No. 02709785.6 filed Mar. 4, 2002.
Office Action mailed Feb. 5, 2009 for Canadian Application No. 2567839 filed May 24, 2005.
Office Action mailed Sep. 5, 2006 for U.S. Appl. No. 10/660,996, filed Sep. 12, 2003.
Office Action mailed Dec. 6, 2007 for U.S. Appl. No. 10/418,514, filed Apr. 18, 2003.
Office Action mailed Jan. 6, 2011 for Israel Application No. 157661 filed Mar. 4, 2002.
Office Action mailed Jul. 6, 2006 for U.S. Appl. No. 10/660,122, filed Sep. 11, 2003.
Office Action mailed Jul. 6, 2007 for U.S. Appl. No. 10/829,826, filed Apr. 22, 2004.
Office Action mailed Mar. 6, 2009 for U.S. Appl. No. 11/233,630, filed Sep. 21, 2005.
Office Action mailed Nov. 6, 2002 for U.S. Appl. No. 09/798,007, filed Mar. 2, 2001.
Office Action mailed Apr. 7, 2009 for Canadian Application No. 2525498 filed May 13, 2004.
Office Action mailed Apr. 7, 2009 for European Application No. 07760292.8 filed Apr. 6, 2007.
Office Action mailed Apr. 7, 2009 for U.S. Appl. No. 10/660,998, filed Sep. 12, 2003.
Office Action mailed Aug. 7, 2007 for U.S. Appl. No. 10/660,998, filed Sep. 12, 2003.
Office Action mailed Feb. 7, 2008 for European Application No. 03796752.8 filed Dec. 5, 2003.
Office Action mailed Jun. 7, 2010 for European Application No. 06800205.4 filed Jul. 21, 2006.
Office Action mailed Jan. 8, 2003 for U.S. Appl. No. 09/798,007, filed Mar. 2, 2001.
Office Action mailed Jan. 8, 2007 for U.S. Appl. No. 09/891,793, filed Jun. 26, 2001.
Office Action mailed Mar. 8, 2005 for U.S. Appl. No. 09/891,793, filed Jun. 26, 2001.
Office Action mailed Mar. 8, 2007 for U.S. Appl. No. 11/060,135, filed Feb. 17, 2005.
Office Action mailed Sep. 8, 2006 for Chinese Application No. 02809122.1 filed Mar. 4, 2002.
Office Action mailed Dec. 9, 2004 for U.S. Appl. No. 10/156,608, filed May 24, 2002.
Office Action mailed Dec. 9, 2009 for U.S. Appl. No. 90/010,210, filed Jun. 27, 2008.
Office Action mailed Dec. 9, 2009 for U.S. Appl. No. 90/010,447, filed Apr. 9, 2009.
Office Action mailed Dec. 9, 2009 for U.S. Appl. No. 90/010,448, filed Apr. 9, 2009.
Office Action mailed Feb. 9, 2007 for Chinese Application No. 02809122.1 filed Mar. 4, 2002.
Office Action mailed Jan. 9, 2008 for Japanese Application No. 2002570692 filed Mar. 4, 2002.
Office Action mailed Jul. 9, 2008 for U.S. Appl. No. 10/660,122, filed Sep. 11, 2003.
Office Action mailed Jul. 9, 2008 for U.S. Appl. No. 11/331,987, filed Jan. 13, 2006.
Office Action mailed Mar. 9, 2004 for U.S. Appl. No. 09/891,793, filed Jun. 26, 2001.
Office Action mailed Nov. 9, 2010 for U.S. Appl. No. 11/331,987, filed Jan. 13, 2006.
Office Action mailed Dec. 10, 2008 for U.S. Appl. No. 10/829,826, filed Apr. 22, 2004.
Office Action mailed Dec. 10, 2009 for U.S. Appl. No. 11/929,910, filed Oct. 30, 2007.
Office Action mailed Feb. 10, 2005 for U.S. Appl. No. 09/798,007, filed Mar. 2, 2001.
Office Action mailed Feb. 10, 2006 for Australian Application No. 2002244250 filed Mar. 4, 2002.
Office Action mailed Jun. 10, 2009 for U.S. Appl. No. 90/010,210, filed Jun. 27, 2008.
Office Action mailed Jun. 10, 2010 for U.S. Appl. No. 90/010,447, filed Apr. 9, 2009.
Office Action mailed Jun. 10, 2010 for U.S. Appl. No. 90/010,448, filed Apr. 9, 2009.
Office Action mailed Oct. 10, 2007 for U.S. Appl. No. 10/754,415, filed Jan. 9, 2004.
Office Action mailed Sep. 10, 2008 for Australian Application No. 2003302236 filed Dec. 5, 2003.
Office Action mailed Aug. 11, 2005 for U.S. Appl. No. 09/891,793, filed Jun. 26, 2001.
Office Action mailed Aug. 11, 2010 for U.S. Appl. No. 90/010,447, filed Apr. 9, 2009.
Office Action mailed Aug. 11, 2010 for U.S. Appl. No. 90/010,448, filed Apr. 9, 2009.
Office Action mailed Dec. 11, 2007 for U.S. Appl. No. 10/660,998, filed Sep. 12, 2003.
Office Action mailed Jul. 11, 2003 for U.S. Appl. No. 09/798,007, filed Mar. 2, 2001.
Office Action mailed Jun. 11, 2010 for U.S. Appl. No. 90/010,210, filed Jun. 27, 2008.
Office Action mailed Mar. 11, 2005 for U.S. Appl. No. 10/325,527, filed Dec. 18, 2002.
Office Action mailed May 11, 2007 for U.S. Appl. No. 10/728,486, filed Dec. 5, 2003.
Office Action mailed Jul. 12, 2006 for U.S. Appl. No. 09/891,793, filed Jun. 26, 2001.
Office Action mailed Jul. 12, 2006 for U.S. Appl. No. 10/660,996, filed Sep. 12, 2003.
Office Action mailed Jun. 12, 2008 for U.S. Appl. No. 10/754,415, filed Jan. 9, 2004.
Office Action mailed Mar. 12, 2008 for European Application No. 06849755.1 filed Apr. 12, 2006.
Office Action mailed May 12, 2002 for U.S. Appl. No. 09/798,007, filed Mar. 2, 2001.
Office Action mailed Aug. 13, 2009 for U.S. Appl. No. 11/674,538, filed Feb. 13, 2007.
Office Action mailed Jul. 13, 2004 for U.S Appl. No. 09/891,793, filed Jun. 26, 2001.
Office Action mailed Jul. 13, 2007 for U.S. Appl. No. 11/233,630, filed Sep. 21, 2005.
Office Action mailed Jul. 13, 2010 for U.S. Appl. No. 11/929,930, filed Oct. 30, 2007.
Office Action mailed Mar. 13, 2006 for U.S. Appl. No. 10/754,415, filed Jan. 9, 2004.
Office Action mailed Nov. 13, 2003 for U.S. Appl. No. 09/891,793, filed Jun. 26, 2001.
Office Action mailed Sep. 13, 2006 for U.S. Appl. No. 09/891,793, filed Jun. 26, 2001.
Office Action mailed Jul. 14, 2004 for U.S. Appl. No. 10/326,642, filed Dec. 18, 2002.
Office Action mailed Jun. 14, 2004 for U.S. Appl. No. 09/891,793, filed Jun. 26, 2001.
Office Action mailed Mar. 14, 2011 for U.S. Appl. No. 11/930,002, filed Oct. 30, 2007.
Office Action mailed Apr. 15, 2008 for U.S. Appl. No. 10/418,514, filed Apr. 18, 2003.
Office Action mailed Aug. 15, 2008 for U.S. Appl. No. 11/331,978, filed Jan. 13, 2006.
Office Action mailed Dec. 15, 2008 for Israel Application No. 157661 filed Mar. 4, 2002.
Office action mailed Dec. 15, 2010 for Canadian Application No. 2508726 filed Dec. 5, 2003.
Office Action mailed Jan. 15, 2008 for Israel Application No. 157661 filed Mar. 4, 2002.
Office Action mailed Jul. 15, 2009 for U.S. Appl. No. 11/060,135, filed Feb. 17, 2005.

(56) References Cited

OTHER PUBLICATIONS

Office Action mailed Mar. 15, 2010 for European Application No. 08730682.5 filed Feb. 25, 2008.
Office Action mailed Nov. 15, 2007 for U.S. Appl. No. 11/331,978, filed Jan. 13, 2006.
Office Action mailed Sep. 15, 2005 for U.S. Appl. No. 10/156,608, filed May 24, 2002.
Office Action mailed Apr. 16, 2002 for U.S. Appl. No. 09/798,007, filed Mar. 2, 2001.
Office Action mailed Apr. 16, 2008 for U.S. Appl. No. 11/233,630, filed Sep. 21, 2005.
Office Action mailed Apr. 16, 2008 for U.S. Appl. No. 11/409,535, filed Apr. 21, 2006.
Office Action mailed Apr. 16, 2009 for U.S. Appl. No. 90/010,210, filed Jun. 27, 2008.
Office Action mailed Aug. 16, 2004 for U.S. Appl. No. 10/325,527, filed Dec. 18, 2002.
Office Action mailed Aug. 16, 2010 for U.S. Appl. No. 11/929,707, filed Oct. 30, 2007.
Office Action mailed Feb. 16, 2011 for U.S. Appl. No. 11/929,910, filed Oct. 30, 2007.
Office Action mailed Jan. 16, 2009 for U.S. Appl. No. 11/582,930, filed Oct. 17, 2006.
Office Action mailed Jul. 16, 2007 for U.S. Appl. No. 11/331,987, filed Jan. 13, 2006.
Office Action mailed Mar. 16, 2006 for U.S. Appl. No. 09/891,793, filed Jun. 26, 2001.
Office Action mailed Mar. 16, 2010 for Canadian Application No. 2616281 filed Jul. 21, 2006.
Office Action mailed May 16, 2008 for U.S. Appl. No. 11/404,561, filed Apr. 12, 2006.
Office Action mailed Nov. 16, 2009 for Japanese Application No. 2005508488 filed Dec. 5, 2003.
Office Action mailed Jun. 17, 2008 for U.S. Appl. No. 11/582,863, filed Oct. 17, 2006.
Office Action mailed Mar. 17, 2006 for U.S. Appl. No. 10/660,122, filed Sep. 11, 2003.
Office Action mailed Nov. 17, 2006 for U.S. Appl. No. 10/754,415, filed Jan. 9, 2004.
Office Action mailed Oct. 17, 2007 for U.S. Appl. No. 10/728,486, filed Dec. 5, 2003.
Office Action mailed Oct. 17, 2008 for U.S. Appl. No. 11/331,978, filed Jan. 13, 2006.
Office Action mailed Sep. 17, 2008 for European Application No. 03796752.8 filed Dec. 5, 2003.
Office Action mailed Sep. 17, 2008 for U.S. Appl. No. 10/660,122, filed Sep. 11, 2003.
Office Action mailed Feb. 18, 2010 for European Application No. 03814656.9 filed Dec. 5, 2003.
Office Action mailed Jan. 18, 2011 for U.S. Appl. No. 11/930,108, filed Oct. 31, 2007.
Office Action mailed May 18, 2005 for New Zealand Application No. 527857 filed Mar. 4, 2002.
Office Action mailed Sep. 18, 2006 for U.S. Appl. No. 10/660,997, filed Sep. 12, 2003.
Office Action mailed Sep. 18, 2008 for Australian Application No. 2003298030 filed Dec. 5, 2003.
Office Action mailed Sep. 18, 2008 for U.S. Appl. No. 10/660,998, filed Sep. 12, 2003.
Office Action mailed Jan. 19, 2007 for U.S. Appl. No. 11/059,776, filed Feb. 17, 2005.
Office Action mailed May 19, 2005 for U.S. Appl. No. 09/891,793, filed Jun. 26, 2001.
Office Action mailed Nov. 19, 2004 for U.S. Appl. No. 10/156,608, filed May 24, 2002.
Office Action mailed Oct. 19, 2007 for U.S. Appl. No. 11/210,516, filed Aug. 24, 2005.
Office Action mailed Sep. 19, 2006 for U.S. Appl. No. 10/660,122, filed Sep. 11, 2003.
Office Action mailed Sep. 19, 2007 for U.S. Appl. No. 10/660,122, filed Sep. 11, 2003.
Office Action mailed Apr. 20, 2007 for U.S. Appl. No. 10/660,122, filed Sep. 11, 2003.
Office Action mailed Apr. 20, 2009 for U.S. Appl. No. 10/891,337, filed Jul. 14, 2004.
Office Action mailed Dec. 20, 2006 for U.S. Appl. No. 10/728,486, filed Dec. 5, 2003.
Office Action mailed Jul. 20, 2005 for U.S. Appl. No. 10/156,608, filed May 24, 2002.
Office Action mailed Jun. 20, 2002 for U.S. Appl. No. 09/798,007, filed Mar. 2, 2001.
Office Action mailed Nov. 20, 2003 for U.S. Appl. No. 10/323,438, filed Dec. 18, 2002.
Office Action mailed Nov. 20, 2006 for U.S. Appl. No. 09/891,793, filed Jun. 26, 2001.
Office Action mailed Nov. 20, 2006 for European Application No. 02709785.6 filed Mar. 4, 2002.
Office Action mailed Sep. 20, 2010 for U.S. Appl. No. 90/010,447, filed Apr. 9, 2009.
Office Action mailed Sep. 20, 2010 for U.S. Appl. No. 90/010,448, filed Apr. 9, 2009.
Office Action mailed Apr. 21, 2009 for U.S. Appl. No. 90/010,209, filed Jun. 27, 2008.
Office Action mailed Mar. 21, 2008 for U.S. Appl. No. 10/660,122, filed Sep. 11, 2003.
Office Action mailed May 21, 2008 for U.S. Appl. No. 10/943,344, filed Sep. 17, 2004.
Office Action mailed Nov. 21, 2003 for U.S. Appl. No. 10/326,642, filed Dec. 18, 2002.
Office Action mailed Nov. 21, 2006 for U.S. Appl. No. 10/660,997, filed Sep. 12, 2003.
Office Action mailed Oct. 21, 2005 for U.S. Appl. No. 10/326,641, filed Dec. 18, 2002.
Office Action mailed Oct. 21, 2009 for U.S. Appl. No. 12/326,800, filed Dec. 2, 2008.
Office Action mailed Apr. 22, 2009 for U.S. Appl. No. 11/491,376, filed Jul. 21, 2006.
Office Action mailed Jul. 22, 2008 for U.S. Appl. No. 90/010,209, filed Jun. 27, 2008.
Office Action mailed Jul. 22, 2008 for U.S. Appl. No. 90/010,210, filed Jun. 27, 2008.
Office Action mailed Nov. 22, 2006 for U.S. Appl. No. 10/660,996, filed Sep. 12, 2003.
Office Action mailed Oct. 22, 2007 for U.S. Appl. No. 11/331,987, filed Jan. 13, 2006.
Office Action mailed Sep. 22, 2003 for U.S. Appl. No. 09/798,007, filed Mar. 2, 2001.
Office Action mailed Sep. 22, 2010 for Canadian Application No. 2510007 filed Dec. 5, 2003.
Office Action mailed Apr. 23, 2010 for U.S. Appl. No. 90/010,210, filed Jun. 27, 2008.
Office Action mailed Feb. 23, 2009 for U.S. Appl. No. 10/943,344, filed Sep. 17, 2004.
Office Action mailed Jan. 23, 2008 for U.S. Appl. No. 10/728,486, filed Dec. 5, 2003.
Office Action mailed Jan. 23, 2008 for U.S. Appl. No. 11/059,776, filed Feb. 17, 2005.
Office Action mailed Jul. 23, 2009 for U.S. Appl. No. 11/070,632, filed Mar. 2, 2005.
Office Action mailed May 23, 2003 for U.S. Appl. No. 09/891,793, filed Jun. 26, 2001.
Office Action mailed May 23, 2005 for U.S. Appl. No. 10/156,608, filed May 24, 2002.
Office Action mailed Oct. 23, 2003 for New Zealand Application No. 527857 filed Mar. 4, 2002.
Office Action mailed Apr. 24, 2009 for U.S. Appl. No. 90/010,447, filed Apr. 9, 2009.
Office Action mailed Apr. 24, 2009 for U.S. Appl. No. 90/010,448, filed Apr. 9, 2009.
Office Action mailed Aug. 24, 2010 for U.S. Appl. No. 90/010,210, filed Jun. 27, 2008.

(56) References Cited

OTHER PUBLICATIONS

Office Action mailed Dec. 24, 2004 for New Zealand Application No. 527857 filed Mar. 4, 2002.
Office Action mailed Feb. 24, 2004 for U.S. Appl. No. 10/326,642, filed Dec. 18, 2002.
Office Action mailed Jan. 24, 2005 for U.S. Appl. No. 10/326,642, filed Dec. 18, 2002.
Office Action mailed Jan. 24, 2007 for U.S. Appl. No. 10/660,998, filed Sep. 12, 2003.
Office Action mailed Jul. 24, 2007 for Mexican Application No. PAA2003007927 filed Sep. 2, 2003.
Office Action mailed Jul. 24, 2007 for U.S. Appl. No. 11/060,135, filed Feb. 17, 2005.
Office Action mailed Jul. 24, 2009 for U.S. Appl. No. 11/754,182, filed May 25, 2007.
Office Action mailed Jun. 24, 2008 for European Application No. 06800205.4 filed Jul. 21, 2006.
Office Action mailed Mar. 24, 2011 for U.S. Appl. No. 11/929,930, filed Oct. 30, 2007.
Office Action mailed Nov. 24, 2009 for U.S. Appl. No. 90/010,210, filed Jun. 27, 2008.
Office Action mailed Sep. 24, 2009 for U.S. Appl. No. 90/010,210, filed Jun. 27, 2008.
Office Action mailed Aug. 25, 2009 for U.S. Appl. No. 11/754,169, filed May 25, 2007.
Office Action mailed Jun. 25, 2009 for U.S. Appl. No. 11/869,449, filed Oct. 9, 2007.
Office Action mailed Jun. 25, 2009 for U.S. Appl. No. 90/010,210, filed Jun. 27, 2008.
Office Action mailed Mar. 25, 2008 for U.S. Appl. No. 11/060,135, filed Feb. 17, 2005.
Office Action mailed Aug. 26, 2003 for U.S. Appl. No. 09/891,793, filed Jun. 26, 2001.
Office Action mailed Aug. 26, 2010 for Canadian Application No. 2508584 filed Dec. 5, 2003.
Office Action mailed Jul. 26, 2004 for U.S. Appl. No. 10/323,438, filed Dec. 18, 2002.
Office Action mailed May 26, 2005 for U.S. Appl. No. 10/156,608, filed May 24, 2002.
Office Action mailed May 26, 2006 for U.S. Appl. No. 10/660,997, filed Sep. 12, 2003.
Office Action mailed Feb. 27, 2003 for U.S. Appl. No. 09/798,007, filed Mar. 2, 2001.
Office Action mailed Feb. 27, 2006 for U.S. Appl. No. 10/418,514, filed Apr. 18, 2003.
Office Action mailed Feb. 27, 2007 for U.S. Appl. No. 10/754,415, filed Jan. 9, 2004.
Office Action mailed Feb. 27, 2007 for U.S. Appl. No. 10/943,344, filed Sep. 17, 2004.
Office Action mailed Jul. 27, 2006 for U.S. Appl. No. 10/728,486, filed Dec. 5, 2003.
Office Action mailed Jul. 27, 2009 for Canadian Application No. 2439655 filed Mar. 4, 2002.
Office Action mailed Mar. 27, 2007 for U.S. Appl. No. 10/418,514, filed Apr. 18, 2003.
Office Action mailed Aug. 28, 2006 for U.S. Appl. No. 10/754,415, filed Jan. 9, 2004.
Office Action mailed Feb. 28, 2006 for U.S. Appl. No. 10/660,996, filed Sep. 12, 2003.
Office Action mailed Jul. 28, 2009 for U.S. Appl. No. 11/754,163, filed May 25, 2007.
Office Action mailed Jul. 28, 2010 for U.S. Appl. No. 90/010,210, filed Jun. 27, 2008.
Office Action mailed May 28, 2003 for U.S. Appl. No. 09/798,007, filed Mar. 2, 2001.
Office Action mailed Mar. 29, 2010 for Australian Application No. 2006272776 filed Jul. 21, 2006.
Office Action mailed May 29, 2007 for U.S. Appl. No. 11/059,776, filed Feb. 17, 2005.
Office Action mailed Oct. 29, 2009 for U.S. Appl. No. 90/010,447, filed Apr. 9, 2009.
Office Action mailed Oct. 29, 2009 for U.S. Appl. No. 90/010,448, filed Apr. 9, 2009.
Office Action mailed Sep. 29, 2005 for U.S. Appl. No. 10/418,514, filed Apr. 18, 2003.
Office Action mailed Aug. 30, 2007 for U.S. Appl. No. 10/754,415, filed Jan. 9, 2004.
Office Action mailed Jul. 30, 2008 for Australian Application No. 2004248107 filed Apr. 23, 2004.
Office Action mailed Jul. 30, 2009 for Japanese Application No. 2002570692 filed Mar. 4, 2002.
Office Action mailed Jun. 30, 2004 for U.S. Appl. No. 09/798,007, filed Mar. 2, 2001.
Office Action mailed Jun. 30, 2010 for U.S. Appl. No. 90/010,210, filed Jun. 27, 2008.
Office Action mailed Jun. 30, 2010 for U.S. Appl. No. 90/010,447, filed Apr. 9, 2009.
Office Action mailed Jun. 30, 2010 for U.S. Appl. No. 90/010,448, filed Apr. 9, 2009.
Office Action mailed May 30, 2006 for U.S. Appl. No. 10/660,996, filed Sep. 12, 2003.
Office Action mailed Nov. 30, 2009 for U.S. Appl. No. 10/660,122, filed Sep. 11, 2003.
Office Action mailed Sep. 30, 2005 for Chinese Application No. 02809122.1 filed Mar. 4, 2002.
Office Action mailed Jan. 31, 2003 for U.S. Appl. No. 09/798,007, filed Mar. 2, 2001.
Office Action mailed Jan. 31, 2007 for Philippines Application No. PH12003500824 filed Mar. 4, 2002.
O"Guinn M.L., et al., "Field Detection of Eastern Equine Encephalitis Virus in the Amazon Basin Region of Peru Using Reverse Transcription-Polymerase Chain Reaction Adapted for FieldIdentification of Arthropod-Borne Pathogens," American Journal of Tropical Medicine and Hygiene, 2004, vol. 70 (2), pp. 164-171.
Oizumi N., et al., "Relationship Between Mutations in the DNA Gyrase and Topoisomerase IV Genes and Nadifloxacin Resistance in Clinically Isolated Quinolone-Resistant *Staphylococcus aureus*," Journal of Infection and Chemotherapy, 2001, vol. 7 (3), pp. 191-194.
Okada M., et al., "Detection and Sequence-Based Typing of Human Adenoviruses Using Sensitiveuniversal Primer Sets for the Hexon Gene," Archives of Virology, 2007, vol. 152 (1), pp. 1-9.
Okuma K., et al., "Dissemination of New Methicillin-Resistant *Staphylococcus aureus* Clones in the Community," Journal of Clinical Microbiology, 2002, vol. 40 (11), pp. 4289-4294.
Oliveira D.C., et al., "Genetic Organization of the Downstream Region of the mecA Element inMethicillin-Resistant *Staphylococcus aureus* Isolates Carrying Different Polymorphisms of This Region," Antimicrobial Agents and Chemotherapy, 2000, vol. 44 (7), pp. 1906-1910.
Oliveira D.C., et al., "Multiplex PCR Strategy for Rapid Identification of Structural Types and Variants of the mec Element in Methicillin-Resistant *Staphylococcus aureus*," Antimicrobial Agents and Chemotherapy, 2002, vol. 46 (7), pp. 2155-2161.
Olsen B., et al., "Transhemispheric Exchange of Lyme Disease Spyrochetes by Seabirds," Journal of Clinical Microbiology, 1995, vol. 33 (12), pp. 3270-3274.
Osiowy C., et al., "Direct Detection of Respiratory Syncytial Virus, Parainfluenza Virus, and Adenovirus in Clinical Respiratory Specimens by a Multiplex Reverse Transcription-PCR Assay," Journal of Clinical Microbiology, 1998, vol. 36 (11), pp. 3149-3154.
Ostrander E.A., et al., "Identification and Characterization of Dinucleotide Repeat (CA)n Markers for Genetic Mapping in Dog," Genomics, 1993, vol. 16 (1), pp. 207-213.
Ounissi H., et al., "Gene Homogeneity for Aminoglycoside-Modifying Enzymes in Gram-PositiveCocci," Antimicrobial Agents and Chemotherapy, 1990, 34 (11), 2164-2168.
Palys T., et al., "Discovery and Classification of Ecological Diversity in the Bacterial World: the Role of DNA Sequence Data," International Journal of Systematic Bacteriology, 1997, vol. 47 (4), pp. 1145-1156.

(56) References Cited

OTHER PUBLICATIONS

Pan Z.Q., et al., "Oligonucleotide-Targeted Degradation of U1 and U2 snRNAs Reveals Differential Interactions of Simian Virus 40 pre-mRNAs with snRNPs," Nucleic Acids Research, 1989, vol. 17 (16), pp. 6553-6568.

Pannetier C., et al., "Quantitative Titration of Nucleic Acids by Enzymatic Amplification Reactions Run to Saturation," Nucleic Acids Research, 1993, vol. 21 (3), pp. 577-583.

Parson W., et al., "Population Data for 101 Austrian Caucasian Mitochondrial DNA d-Loop Sequences: Application of mtDNA Sequence Analysis to a Forensic Case," International Journal of Legal Medicine, 1998, vol. 111 (3), pp. 124-132.

Partial European Search Report for Application No. EP01106974, mailed on Dec. 16, 2002, 2 pages.

Pastorino B., et al., "Development of a TaqMan PCR Assay Without RNA Extraction Step for the Detection and Quantification of African Chikungunya Viruses," Journal of Virological Methods, 2005, vol. 124 (1-2), pp. 65-71.

Paterson A.H., et al., "Fine Mapping of Quantitative Trait Loci Using Selected Overlapping Recombinant Chromosomes, in an Interspecies Cross of Tomato," Genetics, 1990, vol. 124 (3), pp. 735-742.

Pawa A., et al., "Co-Transfer of Plasmids in Association with Conjugative Transfer of Mupirocin or Mupirocin and Penicillin Resistance in Methicillin-Resistant *Staphylococcus aureus*," Journal of Medicinal Microbiology, 2000, vol. 49 (12), pp. 1103-1107.

Payne D., et al., "Antimicrobials: The Challenge of Antibiotic Resistant Bacterial Pathogens: The Medical Need, The Market and Prospects for New Antimicrobial Agents," Current Opinion in Microbiology, 2004, vol. 7, pp. 435-438.

Peng X., et al., "Rapid Detection of *Shigella* Species in Environmental Sewage by an Immunocapture PCR with Universal Primers," Applied and Environmental Microbiology, 2002, vol. 68 (5), pp. 2580-2583.

Perez-Roth E., et al., "Multiplex PCR for Simultaneous Identification of *Staphylococcus aureus* and Detection of Methicillin and Mupirocin Resistance," Journal of Clinical Microbiology, 2001, vol. 39 (11), pp. 4037-4041.

Peters S.E., et al., "Quantification of the Detection of Pneumocystis Carinii by DNA Amplification," Molecular and Cellur Probes, 1992, vol. 6 (2), pp. 115-117.

Pfeffer M., et al., "Genus-Specific Detection of Alphaviruses by a Semi-Nested ReverseTranscription-Polymerase Chain Reaction," American Journal of Tropical Medicine and Hygiene, 1997, vol. 57 (6), pp. 709-718.

Pfeffer M., et al., "Specific Detection of Chikungunya Virus Using a RT-PCR/Nested PCR Combination," Journal of Veterinary Medicine B, 2002, vol. 49 (1), pp. 49-54.

Pieles U., et al., "Matrix-Assisted Laser Desorption Ionization Time-of-Flight Spectrometry: APowerful Tool for the Mass and Sequence Analysis of Natural and Modified Oligonucleotides," Nucleic Acids Research, 1993, vol. 21 (14), pp. 3191-3196.

Pillai S.D., et al., "Rapid Molecular Detection of Microbial Pathogens: Breakthroughs and Challenges," Archives of Virology, 1997, vol. 13, pp. 67-82.

Piper J., et al., "Commercially Available Technique for Rapid Laboratory Detection of MethicillinResistance Among *Staphylococcus aureus*," Diagnostic Microbiology and Infectious Disease, 1988, vol. 11 (3), pp. 177-180.

Poddar S.K., et al., "Detection of Adenovirus using PCR and Molecular Beacon," Journal of Virological Methods, 1999, vol. 82 (1), pp. 19-26.

Pomerantz S.C., et al., "Determination of Oligonucleotide Composition from Mass Spectrometrically Measured Molecular Weight," Journal of the American Society for Mass Spectrometry, 1993, vol. 4 (3), pp. 204-209.

Pring-Akerblom P., et al., "Multiplex Polymerase Chain Reaction for Subgenus-Specific Detection of Human Adenoviruses in Clinical Samples," Journal of Medical Virology, 1999, vol. 58 (1), pp. 87-92.

Pring-Akerblom P., et al., "PCR-Based Detection and Typing of Human Adenoviruses in Clinical Samples," Research in Virology, 1997, vol. 148 (3), pp. 225-231.

Promega. T4 Polynucleotide Kinase, Technical Bulletin No. 519, 2002.

Puthavathana P., et al., "Molecular Characterization of the Complete Genome of Human Influenza H5N1 Virus Isolates from Thailand," Journal of General Virology, 2005, vol. 86 (2), pp. 423-433.

Qadri S.M., et al., "Rapid Detection of Methicillin-Resistant *Staphylococcus aureus* by CrystalMRSA ID System," Journal of Clinical Microbiology, 1994, vol. 32 (7), pp. 1830-1832.

Raaum R.L., et al., "Catarrhine Primate Divergence Dates Estimated from Complete Mitochondria Genomes: Concordance with Fossil and Nuclear DNA Evidence," Journal of Human Evolution, 2005, vol. 48 (3), pp. 237-257.

Ramisse V., et al., "Identification and Characterization of Bacillus anthracis by Multiplex PCR Analysis of Sequences on Plasmids pX01 and pX02 and Chromosomal DNA," FEMS Microbiology Letters, 1996, vol. 145 (1), pp. 9-16.

Reid S.M., et al., "Primary Diagnosis of Foot-and-Mouth Disease by Reverse Transcription Polymerase Chain Reaction," Journal of Virological Methods, 2000, vol. 89 (1-2), pp. 167-176.

Reilly K., et al., "Design and Use of 16s Ribosomal DNA-Directed Primers in Competitive PCRs to Enumerate Proteolytic Bacteria in the Rumen," Microbial Ecology, 2002, vol. 43 (2), pp. 259-270.

Reischl U., "Application of Molecular Biology-Based Methods to theDiagnosis of Infectious Diseases 1, e72-e77.," Frontiers in Bioscience, 1996, vol. 1 (1), pp. e72-e77.

Reischl U., et al., "Rapid Identification of Methicillin-Resistant *Staphylococcus aureus* and Simultaneous Species Confirmation Using Real-Time Fluorescence PCR," Journal of Clinical Microbiology, 2000, vol. 38 (6), pp. 2429-2433.

Roberts M.M., et al., "Three-Dimensional Structure of the Adenovirus Major Coat Protein Hexon," Science, 1986, vol. 232 (4754), pp. 1148-1151.

Roberts M.S., et al., "Recombination and Migration Rates in Natural Populations of Bacillus subtilis and Bacillus mojavensis," Evolution, 1995, vol. 49 (6), pp. 1081-1094.

Robinson D.A., et al., "Multilocus Sequence Typing and the Evolution of Methicillin-Resistant *Staphylococcus aureus*," Clinical Microbiology and Infection, 2004, vol. 10, pp. 92-97.

Rong S., et al., "Design and Application of 60mer Oligonucleotide Microarray in SARS Coronavirus Detection," Chinese Science Bulletin, 2003, vol. 48 (12), pp. 1165-1169.

Ross P., et al., "High Level Multiplex Genotyping by MALDI-TOF Mass Spectrometry," Nature Biotechnology, 1998, vol. 16 (13), pp. 1347-1351.

Ross P.L., et al., "Analysis of DNA Fragments from Conventional and Microfabricated PCR Devices Using Delayed Extraction MALDI-TOF Mass Spectrometry," Analytical Chemistry, 1998, vol. 70 (10), pp. 2067-2073.

Ross P.L., et al., "Discrimination of Single-Nucleotide Polymorphisms in Human DNA Using Peptide Nucleic Acid Probes Detected by MALDI-TOF Mass Spectrometry," Analytical Chemistry, 1997, vol. 69 (20), pp. 4197-4202.

Rota P.A., et al., "Sequencing of a cDNA Clone of the Nucleoprotein Gene of Influenza B/Ann Arbor/1/86," Nucleic Acids Research, 1989, vol. 17 (9), pp. 3595.

Ruan Y., et al., "Comparative Full-Length Genome Sequence Analysis of 14 SARS Coronavirus Isolates and Common Mutations Associated with the Putative Origins of Infection," The Lancet, 2003, vol. 361, pp. 1779-1785, 1832.

Ruest A., et al., "Comparison of the Directigen Flu A+B test, the QuickVue Influenza Test, and Clinical Case Definition to Viral Culture and Reverse Transcription-PCR for Rapid Diagnosis of Influenza Virus Infection," Journal of Clinical Microbiology, 2003, vol. 41 (8), pp. 3487-3493.

Rupf S., et al., "Quantitative Determination of *Streptococcus mutans* by using Competitive Polymerasechain Reaction," European Journal of Oral Sciences, 1999, vol. 107 (2), pp. 75-81.

(56) References Cited

OTHER PUBLICATIONS

Russell K.L., et al., "Transmission Dynamics and Prospective Environmental Sampling of Adenovirus in a Military Recruit Setting," Journal of Infectious Diseases, 2006, vol. 194 (7), pp. 877-885.

Sabat A., et al., "Comparison of PCR-Based Methods for Typing *Staphylococcus aureus* Isolates," Journal of Clinical Microbiology, 2006, vol. 44 (10), pp. 3804-3807.

Sackesen C., et al., "Use of Polymerase Chain Reaction for Detection of Adenovirus in Children Withor Without Wheezing," Turkish Journal of Pediatrics, 2005, vol. 47 (3), pp. 227-231.

Sakai H., et al., "Simultaneous Detection of *Staphylococcus aureus* and Coagulase-Negative *Staphylococci* in Positive Blood Cultures by Real-Time PCR with Two Fluorescence Resonance Energy Transfer Probe Sets," Journal of Clinical Microbiology, 2004, vol. 42 (12), pp. 5739-5744.

Sala M., et al., "Ambiguous Base Pairing of the Purine Analogue 1-(2-Deoxy-B-D-Ribofuranosyl)-Imidazole-4-Carboxamide During PCR," Nucleic Acids Research, 1996, vol. 24 (17), pp. 3302-3306.

Sambrook J., et al., "Molecular Cloning—A Laboratory Manual," 1989, Cold Spring Harbor Laboratory Press, Table of Contents.

Sampath R., et al., "Global Surveillance of Emerging Influenza Virus Genotypes by Mass Spectrometry," Plos ONE, 2007, vol. 2 (5), pp. e489.

Sampath R., et al., "Rapid Identification of Emerging Infectious Agents using PCR and Electrospray Ionization Mass Spectrometry," Annals of the New York Academy of Science, 2007, vol. 1102, pp. 109-120.

Sampath R., et al., "Rapid Identification of Emerging Pathogens: Coronavirus," Emerging Infectious Diseases, 2005, vol. 11 (3), pp. 373-379.

Sanchez A., et al., "Detection and Molecular Characterization of Ebola Viruses Causing Disease in Human and Nonhuman Primates," Journal of Infectious Diseases, 1999, vol. 179 (1), pp. S164-S169.

Sanchez J.L., et al., "Epidemic of Adenovirus-Induced Respiratory Illness Among US Military Recruits: Epidemiologic and Immunologic Risk Factors in Healthy, Young adults," Journal of Medical Virology, 2001, vol. 65 (4), pp. 710-718.

Sanchez-Seco M.P., et al., "A Generic Nested-RT-PCR followed by Sequencing for Detection and Identification of Members of the Alphavirus Genus," Journal of Virological Methods, 2001, vol. 95 (1-2), pp. 153-161.

Santos S.R., et al., "Identification and Phylogenetic Sorting of Bacterial Lineages with Universally Conserved Genes and Proteins," Environmental Microbiology, 2004, vol. 6 (7), pp. 754-759.

Sarantis H., et al., "Comprehensive Detection and Serotyping of Human Adenoviruses by PCR and Sequencing," Journal of Clinical Microbiology, 2004, vol. 42 (9), pp. 3963-3969.

Sauer S., et al., "A Novel Procedure for Efficient Genotyping of Single Nucleotide Polymorphisms," Nucleic Acids Research, 2000, vol. 28 (5), pp. E13.1-E13.8.

Scaramozzino N., et al., "Comparison of Flavivirus Universal Primer Pairs and Development of a Rapid, Highly Sensitive Heminested Reverse Transcription-PCR Assay for Detection of Flaviviruses Targeted to a Conserved Region of the NS5 Gene Sequences," Journal of Clinical Microbiology, 2001, vol. 39 (5), pp. 1922-1927.

Schabereiter-Gurtner C., et al., "Application of Broad-Range 16s rRNA PCR Amplification and DGGE Fingerprinting for Detection of Tick-Infecting Bacteria," The Journal of Microbiological Methods, 2003, vol. 52 (2), pp. 251-260.

Scheffner M., et al., "The E6 Oncoprotein Encoded by Human Papillomavirus Types 16 and 18 Promotes the Degradation of p53," Cell, 1990, vol. 63 (6), pp. 1129-1136.

Schena M., et al., "Genome Analysis with Gene Expression Microarrays," Bioessays, 1996, vol. 18 (5), pp. 427-431.

Scheuermann R.H., et al., "Polymerase Chain-Reaction-Based mRNA Quantification Using an Internal Standard: Analysis of Oncogene Expression," Methods in Enzymology, 1993, vol. 218, pp. 446-473.

Schlecht N.F., et al., "Viral Load as a Predictor of the Risk of Cervical Intraepithelial Neoplasia," British Journal of Cancer, 2003, vol. 103 (4), pp. 519-524.

Schmidt T.M., et al., "Analysis of a Marine Pikoplankton Community by 16s rRNA Gene Cloning and Sequencing," Journal of Bacteriology, 1991, vol. 173 (14), pp. 4371-4378.

Schmitz F.J., et al., "Development of a Multiplex-PCR for Direct Detection of the Genes for Enterotoxin B and C, and Toxic Shock Syndrome Toxin-1 in *Staphylococcus aureus* Isolates," Journal of Medical Microbiology, 1998, vol. 47 (4), pp. 335-340.

Schmitz F.J., et al., "Development of Resistance to Ciprofloxacin, Rifampin, and Mupirocin in Methicillin-Susceptible and -Resistant *Staphylococcus aureus* Isolates," Antimicrobial Agents and Chemotherapy, 2000, vol. 44 (11), pp. 3229-3231.

Schmitz F.J., et al., "Specific Information Concerning Taxonomy, Pathogenicity and Methicillin Esistance of *Staphylococci* Obtained by a Multiplex PCR," Journal of Medical Microbiology, 1997, vol. 46 (9), pp. 773-778.

Schram K.H., et al., "Mass Spectrometry of Nucleic Acid Components," Methods of Biochemical Analysis, 1990, vol. 34, pp. 203-280.

Schultz J.C., et al., "Polymerise Chain Reaction Products Analyzed by Charge Detection Mass Spectrometry," Rapid Communications in Mass Spectrometry, 1999, vol. 13 (1), pp. 15-20.

Schwartz M., et al., "Prenatal Diagnosis of Alpha-1-Antitrypsin Deficiency Using Polymerase Chainreaction (PCR). Comparison of Conventional RFLP Methods with PCR used in Combination with Allelespecific Oligonucleotides or RFLP Analysis," Clinical Genetics, 1989, vol. 36 (6), pp. 419-426.

Schweiger B., et al., "Application of a Fluorogenic PCR Assay for Typing and Subtyping of Influenza Viruses in Respiratory Samples," Journal of Clinical Microbiology, 2000, vol. 38 (4), pp. 1552-1558.

Sciacchitano C.J., "Analysis of Polymerase Chain Reaction-Amplified DNA Fragments of Clostridium Botulinum Type E Neurotoxin Gene by High Performance Capillary Electrophoresis," Journal of Liquid Chromatography & Related Technologies, 1996, vol. 19 (13), pp. 2165-2178.

Scott-Taylor T.H., et al., "Conserved Sequences of the Adenovirus Genome for Detection of all Human Adenovirus Types by Hybridization," Journal of Clinical Microbiology, 1992, vol. 30 (7), pp. 1703-1710.
Seifarth W., et al., "Rapid Identification of All Known Retroviral Reverse Transcriptase Sequences with a Novel Versatile Detection Assay," AIDS Research and Human Retroviruses, 2000, vol. 16 (8), pp. 721-729.
Sellner L., et al., "A Single-Tube Nested RT-PCR for the Detection of Ross River Virus," Methods in Molecular Biology, 1998, vol. 92, pp. 145-152.
Sellner L.N., et al., "Sensitive Detection of Ross River Virus—A One-Tube Nested RT-PCR," Journal of Virological Methods, 1994, vol. 49 (1), pp. 47-58.
Senko M.W., et al., "Determination of Monoisotopic Masses and Ion Populations for Large Biomoleculesfrom Resolved Isotopic Distributions," Journal of the American Society for Mass Spectrometry, 1995, vol. 6, pp. 229-233.
Seshadri R., et al., "Differential Expression of Translational Elements by Life Cycle Variants of Coxiella Burnetii," Infection and Immunity, 1999, vol. 67 (11), pp. 6026-6033.
Shadan F.F., et al., "N-Butyrate, A Cell Cycle Blocker, Inhibits the Replication of Polyomaviruses and Papillomaviruses but Not That of Adenoviruses and Herpesviruses," Journal of Virology, 1994, vol. 68 (8), pp. 4785-4796.
Shaver Y.J., et al., "Restriction Fragment Length Polymorphism of rRNA Operons for Discrimination and Intergenic Spacer Sequences for Cataloging of Bacilus Subtilis Sub-Groups," Journal of Microbiological Methods, 2002, vol. 50 (2), pp. 215-223.

(56) References Cited

OTHER PUBLICATIONS

Shaver Y.J., et al., "Variation in 16s-23s rRNA Intergenic Spacer Regions Among Bacilus Subtilis 168 Isolates," Molecular Microbiology, 2001, vol. 42 (1), pp. 101-109.

Shimaoka M., et al., "Detection of the Gene for Toxic Shock Syndrome Toxin 1 in Siaphylococcusaureus by Enzyme-Labelled Oligonucleotideprobes," Journal of Medical Microbiology, 1996, vol. 44 (3), pp. 215-218.

Shimaoka M., et al., "Development of Enzyme-Labeled Oligonucleotide Probe for Detection of MecA Gene in Methicillin-Resistant Staphylococcus aureus," Journal of Clinical Microbiology, 1994, vol. 32 (8), pp. 1866-1869.

Shrestha N.K., et al., "Rapid Identification of Staphylococcus aureus and the MecA Gene from BacT/ALERT Blood Culture Bottles by Using the Lightcycler System," Journal of Clinical Microbiology, 2002, vol. 40 (7), pp. 2659-2661.

Simonsen L., et al., "The Impact of Influenza Epidemics on Hospitalizations," Journal of Infectious Diseases, 2000, vol. 181 (3), pp. 831-837.

Skov R.L., et al., "Evaluation of a New 3-h Hybridization Method for Detecting the MecA Gene in Staphylococcus aureus and Comparison with Existing Genotypic and Phenotypic Susceptibility Testing Methods," Journal of Antimicrobial Chemotherapy, 1999, vol. 43 (4), pp. 467-475.

Smirnov I.P., et al., "Application of DNA-Binding Polymers for Preparation of DNA for Analysis by Matrix-Assisted Laser Desorption/Ionization Mass Spectrometry," Rapid Communications in Mass Spectrometry, 2001, vol. 15 (16), pp. 1427-1432.

Smith T.F., et al., "Comparison of Biosequences," Advances in Applied Mathematics, 1981, vol. 2, pp. 482-489.

Song F., et al., "Identification of cry11-type Genes from Bacilus Thuringiensis Strains and Characterization of a Novel Cry11-Type Gene," Applied and Environmental Microbiology, 2003, vol. 69, pp. 5207-5211.

Spackman E., et al., "Development of a Real-Time Reverse Transcriptase PCR Assay for Type A Influenzavirus and The Avian H5 and H7 Hemagglutinin Subtypes," Journal of Clinical Microbiology, 2002, vol. 40 (9), pp. 3256-3260.

Spiess L., et al., "Trehalose is a Potent PCR Enhancer: Lowering of DNA Melting Temperature and Thermal Stabilization of Taq Polymerase by the Disaccharide Trehalose," Clinical Chemistry, 2004, vol. 50 (7), pp. 1256-1259.

Srinivasan J.R., et al., "Matrix-Assisted Laser Desorption/Ionization Time-of-Flight Mass Spectrometry as a Rapid Screening Method to Detect Mutations Causing Tay-Sachs Disease," Rapid Communications in Mass Spectrometry, 1997, vol. 11 (10), pp. 1144-1150.

Steffens D.L., et al., "Sequence Analysis of Mitochondrial DNA Hypervariable Regions Using Infrared Fluorescence Detection," BioTechniques, 1998, vol. 24 (6), pp. 1044-1046.

Stephensen C.B., et al., "Phylogenetic Analysis of a Highly Conserved Region of the Poymerase Gene from 11 Coronaviruses and Development of a Consensus Poymerase Chain Reaction Assay," Virus Research, 1999, vol. 60 (2), pp. 181-189.

Stone B., et al., "Rapid Detection and Simultaneous Subtype Differentiation of Influenza A Viruses by Real Time PCR," Journal of Virological Methods, 2004, vol. 117 (2), pp. 103-112.

Stoneking M., et al., "Population Variation of Human mtDNA Control Region Sequences Detected by Enzymatic Amplification and Sequence-Specific Oligonucleotide Probes," American Journal of Human Genetics, 1991, vol. 48 (2), pp. 370-382.

Stratagene Catalog, Gene Characterization Kits, 1988, pp. 39.

Strommenger B., et al., "Multiplex PCR Assay for Simultaneous Detection of Nine Clinically Relevant Antibiotic Resistance Genes in Staphylococcus aureus," Journal of Clinical Microbiology, 2003, vol. 41 (9), pp. 4089-4094.

Studdert M.J., et al., "Polymerase Chain Reaction Tests for the Identification of Ross River, Kunjinand Murray Valley Encephalitis Virus Infections in Horses," Australian Veterinary Journal, 2003, vol. 81 (1-2), pp. 76-80.

Stuhlmeier R., et al., "Fast, Simultaneous, and Sensitive Detection of Staphylococci," Journal of Clinical Pathology, 2003, vol. 56 (10), pp. 782-785.

Sumner J.W., et al., "PCR Amplification and Comparison of Nucleotide Sequences from the groESL Heat Shock Operon of Ehrlichia Species," Journal of Critical Microbiology, 1997, vol. 35 (8), pp. 2087-2092.

Sundsfjord A., et al., "Genetic Methods for Detection of Antimicrobial Resistance," APMIS : Acta Pathologica, Microbiologica, et Immunologica Scandinavica, 2004, vol. 112 (11-12), pp. 815-837.

Supplementary European Search Report for Application No. 04775904.8, mailed on Jul. 7, 2008, 8 pages.

Supplementary European Search Report for Application No. EP03796752.8, mailed on Aug. 7, 2007, 3 pages.

Supplementary European Search Report for Application No. EP03810055.8, mailed on Jun. 8, 2007, 4 pages.

Supplementary European Search Report for Application No. EP03814656, mailed on Oct. 16, 2007, 2 pages.

Supplementary European Search Report for Application No. EP04752257.8, mailed on Feb. 15, 2006, 2 pages.

Supplementary European Search Report for Application No. EP05753037, mailed on Aug. 21, 2009, 2 pages.

Supplementary Partial European Search Report for Application No. EP02709785.6, mailed Sep. 1, 2005, 5 pages.

Supplementary Partial European Search Report for Application No. EP05751872.2, mailed on Jan. 28, 2008, 8 pages.

Supplementary Partial European Search Report for Application No. EP05856582.1, mailed on Oct. 27, 2008, 10 pages.

Swaminathan B., et al., "PulseNet: The Molecular Subtyping Network for Foodborne Bacterial Disease Surveillance, United States," Emerging Infectious Diseases, 2001, vol. 7 (3), pp. 382-389.

Swanborg R.H., et al., "Human Herpesvirus 6 and Chlamydia Pneumoniae as Etiologic Agents in Multiplesclerosis—a Critical Review," Microbes and Infection / Institut Pasteur, 2002, vol. 4 (13), pp. 1327-1333.

Swenson J.M., et al., "Performance of Eight Methods, Including Two New Rapid Methods, for Detection of Oxacillin Resistance in a Challenge Set of Staphylococcus aureus Organisms," Journal of Clinical Microbiology, 2001, vol. 39 (10), pp. 3785-3788.

Takagaki Y., et al., "Four Factors are Required for 3"-End Cleavage of Pre-mRNAs," Genes and Development, 1989, vol. 3 (11), pp. 1711-1724.

Takahashi H., et al., "Characterization of gryA, gryB, grIA and grIB Mutations in Fluoroquinolone-Resistant Clinical Isolates of Staphylococcus aureus," The Journal of Antimicrobial Chemotherapy, 1998, vol. 41 (1), pp. 49-57.

Takahata M., et al., "Mutations in the GyrA and Gr1A Genes of Quinolone-Resistant Clinical Isolates of Methicillin-Resistant Staphylococcus aureus," The Journal of Antimicrobial Chemotherapy, 1996, vol. 38 (3), pp. 543-546.

Takayama R., et al., "Quantification of Adenovirus Species B and C Viremia by Real-Time PCR in Adults and Children Undergoing Stem Cell Transplantation," Journal of Medical Virology, 2007, vol. 79 (3), pp. 278-284.

Takeuchi S., et al., "Serotyping of Adenoviruses on Conjunctival Scrapings by PCR and Sequence Analysis," Journal of Clinical Microbiology, 1999, vol. 37 (6), pp. 1839-1845.

Talaat A.M., et al., "Genome-Directed Primers for Selective Labeling of Bacterial Transcripts for DNA Microarray Analysis," Nature Biotechnology, 2000, vol. 18 (6), pp. 679-682.

Tan T.Y., "Use of Molecular Techniques for the Detection of Antibiotic Resistance in Bacteria," Expert Review of Molecular Diagnostics, 2003, vol. 3 (1), pp. 93-103.

Tanabe F., et al., "The Properties and Mec A Gene of the Methicillin-Resistant Staphylococcus aureus Isolated in Fukushima Medical College Hospital," Fukushima Journal of Medical Science, 1993, vol. 39 (1), pp. 35-42.

Tang K., et al., "Detection of 500-Nucleotide DNA by Laser Desorption Mass Spectrometry," Rapid Communications in Mass Spectrometry, 1994, vol. 8 (9), pp. 727-730.

Tang K., et al., Double-Stranded DNA Analysis by Matrix Assisted Laser Desorption/Ionization, 42nd ASMS Conference on Mass Spectrometry, 1994.

(56) References Cited

OTHER PUBLICATIONS

Tang K., et al., "Matrix-Assisted Laser Desorption/Ionization of Restriction Enzyme-Digested DNA," Rapid Communications in Mass Spectrometry, 1994, vol. 8 (2), pp. 183-186.

Tang K., et al., Matrix-Assisted Laser Desorption/Ionization Mass Spectrometry of Oligonucleotides, Dissertation submitted to the Faculty of Vanderbilt University, 1994.

Tarassishin L., et al., "Adenovirus Core Protein VII Displays a Linear Epitope Conserved in a Range of Human Adenoviruses," Journal of General Virology, 1999, vol. 80 (Pt 1), pp. 47-50.

Tarassishin L., et al., "An Epitope on the Adenovirus Fibre Tail is Common to all Human Subgroups," Archives of Virology, 2000, vol. 145 (4), pp. 805-811.

Tatuch Y., et al., "Heteroplasmic mtDNA Mutation (T-G) at 8993 Can Cause Leigh Disease When the Percentage of Abnormal mtDNA is High," The American Journal of Human Genetics, 1992, vol. 50 (4), pp. 852-858.

Taubenberger J.K., et al., "Characterization of the 1918 Influenza Virus Polymerase Genes," Nature, 2005, vol. 437 (7060), pp. 889-893.

Taylor L.H., et al., "Risk Factors for Human Disease Emergence," Philosophical Transactions of the Royal Society of London Series B, Biological Sciences, 2001, vol. 356 (1411), pp. 983-989.

Tenover F.C., et al., "Characterization of a Strain of Community-Associated Methicillin-Resistant*Slaphylococcus aureus* Widely Disseminated in the United States," Journal of Clinical Microbiology, 2006, vol. 44 (1), pp. 108-118.

Teramura T., et al., "Quantitative Detection of Serum Adenovirus in a Transplant Recipient," Lancet, 2002, vol. 359 (9321), pp. 1945.

Thiel V., et al., "Infectious RNA Transcribed in Vitro from a cDNA Copy of the Human Coronavirus Genome Cloned in Vaccinia Virus," The Journal of General Virology, 2001, vol. 82 (Pt 6), pp. 1273-1281.

Thompson J.D., et al., "Clustal W: Improving the Sensitivity of Progressive Multiple Sequence Alignmen Through Sequence Weighting, Position-Specific Gap Penalties and Weight Matrix Choice," Nucleic Acids Research, 1994, vol. 22 (22), pp. 4673-4680.

Thompson W.W., et al., "Influenza-Associated Hospitalizations in the United States," The Journal of the American Medical Association, 2004, vol. 292 (11), pp. 1333-1340.

Tokue Y., et al., "Comparison of a Polymerase Chain Reaction Assay and a Conventional Microbiologic Method for Detection of Methicillin-Resistant *Slaphylococcus aureus*," Antimicrobial Agents and Chemotherapy, 1992, vol. 36 (1), pp. 6-9.

Tong J., et al., "Ligation Reaction Specificities of an NAD+-Dependent DNA Ligase from the Hyperthermophile Aquifex Aeolicus," Nucleic Acids Research, 2000, vol. 28 (6), pp. 1447-1454.

Top F.H Jr., "Control of Adenovirus Acute Respiratory Disease in U.S. Army Trainees," The Yale Journal of Biology and Medicine, 1975, vol. 48 (3), pp. 185-195.

Torroni A., et al., "Classification of European mtDNAs from an Analysis of Three European Populations," Genetics, 1996, vol. 144 (4), pp. 1835-1850.

Towner K.J., et al., "Development and Evaluation of a PCR-Based Immunoassay for the Rapid Detection of Methicillin-Resistant *Staphylococcus aureus*," Journal of Medical Microbiology, 1998, vol. 47 (7), pp. 607-613.

Tsuneyoshi T., et al., "Mass Spectrometric Gene Diagnosis of One-Base Substitution from Polymerase Chain Reaction Amplified Human DNA," Rapid Communications in Mass Spectometry, 1997, vol. 11 (7), pp. 719-722.

Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.

Udo E.E., et al., "A Chromosomal Location of the MupA Gene in *Staphylococcus aureus* Expressing High-Level Mupirocin Resistance," The Journal of Antimicrobial Chemotherapy, 2003, vol. 51 (5), pp. 1283-1286.

Udo E.E., et al., "Genetic Analysis of Methicillin-Resistant *Staphylococcus aureus* Expressing High-and Low-Level Mupirocin Resistance," Journal of Medical Microbiology, 2001, vol. 50 (10), pp. 909-915.

Udo E.E., et al., "Rapid Detection of Methicillin Resistance in *Staphylococci* Using a Slide Latex Agglutination Kit," International Journal of Antimicrobial Agents, 2000, vol. 15 (1), pp. 19-24.

Unal S., et al., "Detection of Methicillin-Resistant *Staphylococci* by Using the Polymerase Chain Reaction," Journal of Clinical Microbiology, 1992, vol. 30 (7), pp. 1685-1691.

Upton A., et al., "Mupirocin and *Staphylococcus aureus*: A Recent Paradigm of Emerging Antibiotic Resistance," The Journal of Antimicrobial Chemotherapy, 2003, vol. 51 (3), pp. 613-617.

Vabret A., et al., "Development of a PCR-and Hybridization-Based Assay (PCR Adenovirus Consensus) for the Detection and the Species Identification of Adenoviruses in Respiratory Specimens," Journal of Clinical Virology, 2004, vol. 31 (2), pp. 116-122.

Van Aerschot A., et al., "In Search of Acyclic Analogues as Universal Nucleosides in Degenerate Probes," Nucleosides and Nucleotides, 1995, vol. 14 (3-5), pp. 1053-1056.

Van Baar B.L., "Characterisation of Bacteria by Matrix-Assisted Laser Desorption/Ionisation and Electrospray Mass Spectrometry," FEMS Microbiology Reviews, 2000, vol. 24 (2), pp. 193-219.

Van Camp G., et al., "Amplification and Sequencing of Variable Regions in Bacterial 23s Ribosomal RNA Genes with Conserved Primer Sequences," Current Microbiology, 1993, vol. 27 (3), pp. 147-151.

Van Der Vossen J.M., et al., "DNA Based Typing Identification and Detection Systems for Food Spoilage Microorganisms: Development and Implementation," International Journal of Food Microbiology, 1996, vol. 33 (1), pp. 35-49.

Van Der Zee H., et al., "Rapid and Alternative Screening Methods for Microbiological Analysis," Journal of AOAC International, 1997, vol. 80 (4), pp. 934-940.

Van Dinten L.C., et al., "Proteolytic Processing of the Open Reading Frame lb-EncodedPart of Arterivirus Replicase is Mediated by nsp4 Serine Protease and is Essential for Virus Replication," Journal of Virology, 1999, vol. 73 (3), pp. 2027-2037.

Van Elden L.J., et al., "Clinical Diagnosis of Influenza Virus Infection: Evaluation of Diagnostic Tools in General Practice," The British Journal of General Practice, 2001, vol. 51 (469), pp. 630-634.

Van Elden L.J., et al., "Simultaneous Detection of Influenza Viruses A and B Using Real-Time Quantitative PCR," Journal of Clinical Microbiology, 2001, vol. 39 (1), pp. 196-200.

Van Ert M.N., et al., "Mass Spectrometry Provides Accurate Characterization of Two Genetic Marker Types in Bacillus Anthracis," Bio Techniques, 2004, vol. 37 (4), pp. 642-651.

Van Leeuwen W.B., et al., "Multilocus Sequence Typing of *Staphylococcus aureus* with DNA Array Technology," Journal of Clinical Microbiology, 2003, vol. 41 (7), pp. 3323-3326.

Van Leeuwen W.B., et al., "Rapid Detection of Methicillin-Resistance in *Staphylococcus aureus* Isolates by the MRSA-Screen Latex Agglutination Test," Journal of Clinical Microbiology, 1999, vol. 37 (9), pp. 3029-3030.

Vanchiere J.A., et al., "Detection of BK Virus and Simian Virus 40 in the Urine of Healthy Children," Journal of Medical Virology, 2005, vol. 75 (3), pp. 447-454.

Vanderhallen H., et al., "Identification of Encephalomyocarditis Virus in Clinical Samples by ReverseTranscription-PCR Followed by Genetic Typing Using Sequence Analysis," Journal of Clinical Microbiology, 1998, vol. 36 (12), pp. 3463-3467.

Vannuffel P., et al., "Specific Detection of Methicillin-Resistant *Staphylococcus* Species by Multiplex PCR," Journal of Clinical Microbiology, 1995, vol. 33 (11), pp. 2864-2867.

Vannuffel P., et al., "Rapid and Specific Molecular Identification of Methicillin-Resistant *Staphylococcus aureus* in Endotracheal Aspirates from Mechanically Ventilated Patients," Journal of Clinical Microbiology, 1998, vol. 36 (8), pp. 2366-2368.

(56) References Cited

OTHER PUBLICATIONS

Verma S., et al., "Modified Oligonucleotides: Synthesis and Strategy for Users," Annual Review of Biochemistry, 1998, vol. 67, pp. 99-134.

Videla C., et al., "Genomic Analysis of Adenovirus Isolated from Argentinian Children with Acute Lower Respiratory Infections," Journal of Clinical Virology, 1999, vol. 14 (1), pp. 67-71.

Vilchez R.A. et al., "Detection of Polyomavirus Simian Virus 40 Tumor Antigen DNA in AIDS-Related Systemic Non-Hodgkin Lymphoma," Journal of Acquired Immune Deficiency Syndromes, 2002, vol. 29 (2), pp. 109-116.

Voelter C., et al., "Screening Human Tumor Samples with a Broad-Spectrum Polymerase Chain Reaction Method for the Detection of Polyomaviruses," Virology, 1997, vol. 237 (2), pp. 389-396.

Volokhov D., et al., "Microarray Analysis of Erythromycin Resistance Determinants," Journal of Applied Microbiology, 2003, vol. 95 (4), pp. 787-798.

Von Eiff C., et al., "Pathogenesis of Infections Due to Coagulase-Negative *Staphylococci*," The Lancet Infectious Diseases, 2002, vol. 2 (11), pp. 677-685.

Von Wintzingerode F., et al., "Base-Specific Fragmentation of Amplified 16S rRNA Genes Analyzed by Mass Spectrometry: A Tool for Rapid Bacterial Identification," Proceedings of the National Academy of Sciences, 2002, vol. 99 (10), pp. 7039-7044.

Walker E.S., et al., "A Decline in Mupirocin Resistance in Methicillin-Resistant *Staphylococcus aureus* Accompanied Administrative Control of Prescriptions," Journal of Clinical Microbiology, 2004, vol. 42 (6), pp. 2792-2795.

Wallace S.S., et al., "The Enigma of Endonuclease VIII," DNA Repair, 2003, vol. 2 (5), pp. 441-453.

Wallet F., et al., "Choice of a Routine Method for Detecting Methicillin-Resistance in *Staphylococci*," The Journal of Antimicrobial Chemotherapy, 1996, vol. 37 (5), pp. 901-909.

Walters J.J., et al., "Genotyping Single Nucleotide Polymorphisms Using Intact Polymerase Chain Reaction Products by Electrospray Quadrupole Mass Spectrometry," Rapid Communications in Mass Spectrometry, 2001, vol. 15 (18), pp. 1752-1759.

Wang G., et al., "Targeted Mutagenesis in Mammalian Cells Mediated by Intracellular Triple Helix Formation," Molecular and Cellular Biology, 1995, vol. 15 (3), pp. 1759-1768.

Ward C.L., et al., "Design and Performance Testing of Quantitative Real Time PCR Assays for Influenza A and B Viral Load Measurement," Journal of Clinical Virology, 2004, vol. 29 (3), pp. 179-188.

Watanabe K., et al., "ICB Database: The gyrB Database for Identification and Classification of Bacteria," Nucleic Acids Research, 2001, vol. 29 (1), pp. 344-345.

Weissenbacher M., et al., "Etiologic and Clinical Evaluation of Acute Lower Respiratory TractInfections in Young Argentinean Children: An Overview," Reviews of Infectious Diseases, 1990, vol. 12 (Suppl 8), pp. S889-S898.

Welham K.J., et al., "The Characterization of Micro-Organisms by Matrix-Assisted Laser Desorption/Lonization Time-of-Flight Mass Spectrometry," Rapid Communications in Mass Spectrometry, 1998, vol. 12 (4), pp. 176-180.

Wertheim H.F., et al., "Effect of Mupirocin Treatment on Nasal, Pharyngeal, and Perineal Carriage of *Staphylococcus aureus* in Healthy Adults," Antimicrobial Agents and Chemotherapy, 2005, vol. 49 (4), pp. 1465-1467.

Westermann P., et al., "Inhibition of Expression of SV40 Virus Large T-Antigen by Antisense Oligodeoxyribonucleotides," Biomedica Biochimica Acta, 1989, vol. 1, pp. 85-93.

Whiley D.M., et al., "Simultaneous Detection and Differentiation of Human Polyomaviruses JC and BK by a Rapid and Sensitive PCR-ELAHA Assay and a Survey of the JCV Subtypes within an Australian Population," Journal of Medical Virology, 2004, vol. 72 (3), pp. 467-472.

Wichelhaus T.A., et al., "Rapid Detection of Epidemic Strains of Methicillin-Resistant*Staphylococcus aureus*," Journal of Clinical Microbiology, 1999, vol. 37 (3), pp. 690-693.

Wickham T.J., "Targeting Adenovirus," Gene Therapy, 2000, vol. 7 (2), pp. 110-114.

Widjojoatmodjo M.N., et al., "Rapid Identification of Bacterial by PCR-Single-Strand Conformation Polymorphism," Journal of Clinical Microbiology, 1994, vol. 32 (12), pp. 3002-3007.

Widjojoatmodjo M.N., et al., "The Magnetic Immuno Polymerase Chain Reaction Assay for Direct Detection of Salmonellae in Fecal Samples," Journal of Clinical Microbiology, 1992, vol. 30 (12), pp. 3195-3199.

Winger B.E., et al., "High Resolution Accurate Mass Measurements of Biomolecules using a new Electrospray Ionization Ion Cyclotron Resonance Mass Spectrometer," Journal American Society for Mass Spectrometry, 1993, vol. 4 (7), pp. 566-577.

Wolter A., et al., "Negative Ion FAB Mass Spectrometric Analysis of Non-Charged Key Intermediates in Oligonucleotide Synthesis: Rapid Identification of Partially Protected Dinucleoside Monophosphates," Biomedical and Environmental Mass Spectrometry, 1987, vol. 14, pp. 111-116.

Woo T.H., et al., "Identification of Leptospira Inadai by Continuous Monitoring of Fluorescence during Rapid Cycle PCR," Systematic and Applied Microbiology, 1998, vol. 21 (1), pp. 89-96.

Wood S.R., et al., "Rapid Detection and Serotyping of Adenovirus by Direct Immunofluorescence," Journal of Medical Virology, 1997, vol. 51 (3), pp. 198-201.

Wright K.E., et al., "Typing and Subtyping of Influenza Viruses in Clinical Samples by PCR," Journal of Clinical Microbiology, 1995, vol. 33 (5), pp. 1180-1184.

Written Opinion for Application No. PCT/US2004/33742, mailed on May 15, 2006, 5 pages.

Wu S., et al., "Genetic Organization of the mecA Region in Methicillin-Susceptible and Methicillin-Resistant Strains of *Staphylococcus sciuri*," The Journal of Bacteriology, 1998, vol. 180 (2), pp. 236-242.

Wu X., et al., "Establishment of a Fluorescent Polymerase Chain Reaction Method for the Detection of SARS-Associated Coronavhus and its Clinical Application," Chinese Medical Journal, 2003, vol. 116 (7), pp. 988-990.

Wunschel D., et al., "Discrimination Among the B. Cereus Group, in Comparison to B. Subtilis, by Structural Carbohydrate Profiles and Ribosomal RNA Spacer Region PCR," Systematic and Applied Microbiology, 1994, vol. 17, pp. 625-635.

Wunschel D.S., et al., "Analysis of Double-Stranded Polymerase Chain Reaction Products from the Bacilus Cereus Group by Electrospray Lonization Fourier Transform Lon Cyclotron Resonance Mass Spectrometry," Rapid Communications in Mass Spectrometry, 1996, vol. 10 (1), pp. 29-35.

Wunschel D.S., et al., "Heterogeneity in Bacillus Cereus PCR Products Detected by ESI-FTICR Mass Spectrometry," Analytical Chemistry, 1998, vol. 70 (6), pp. 1203-1207.

Wunschel D.S., et al., "Mass spectrometric characterization of DNA for molecular biological applications: advances using MALDI and ESI," Advances in Mass Spectrometry, 1998, vol. 14, Elsevier, pp. 377-406.

Xu L., et al., "Electrophore Mass Tag Dideoxy DNA Sequencing," Analytical Chemistry, 1997, vol. 69 (17), pp. 3595-3602.

Xu W., et al., "Species-Specific Identification of Human Adenoviruses by a Multiplex PCR Assay," Journal of Clinical Microbiology, 2000, vol. 38 (11), pp. 4114-4120.

Xu W., et al., "Type-Specific Identification of Human Adenovirus, 3, 7, and 21 by a Multiplex PCR Assay," Journal of Medical Virology, 2001, vol. 64 (4), pp. 537-542.

Xu X., et al., "Intercontinental Circulation of Human Influenza A(H1N2) Reassortant Viruses During the 2001-2002 Influenza Season," The Journal of Infectious Diseases, 2002, vol. 186 (10), pp. 1490-1493.

Yao Z.P., et al., "Mass Spectrometry Based Proteolytic Mapping for Rapid Virus Identification," Analytical Chemistry, 2002, vol. 74 (11), pp. 2529-2534.

(56) References Cited

OTHER PUBLICATIONS

Yasui T., et al., "A Specific Oligonucleotide Primer for the Rapid Detection of Lactobacillus Lindneri by Polymerase Chain Reaction," Canadian Journal of Microbiology, 1997, vol. 43 (2), pp. 157-163.

Ye K., et al., "Three Distinct Promoters Direct Transcription of Different 5" Untranslated Regions of the Human Interleukin 1 Type 1 Receptor. A Possible Mechanism for Control of Translation," Cytokine, 1996, vol. 8 (6), pp. 421-429.

Yun H.J., et al., "Increased Antibacterial Activity of OW286, A Novel Fluoronaphthyridone Antibiotic, Against *Staphylococcus aureus* Strains with Defined Mutations in DNA Gyrase and Toposiomerase IV," International Journal of Antimicrobial Agents, 2005, vol. 25 (4), pp. 334-337.

Zeng Z.B., "Precision Mapping of Quantitative Trait Loci," Genetics, 1994, vol. 136 (4), pp. 1457-1468.

Zhang J., et al., "PowerBLAST: A New Network BLAST Application for Interactive or Automated Sequence Analysis and Annotation," Genome Research, 1997, vol. 7 (6), pp. 649-656.

Zhang K., et al., "New Quadriplex PCR Assay for Detection of Methicillin and Mupirocin Resistance and Simultaneous Discrimination of *Staphylococcus aureus* from Coagulase-Negative *Staphylococci*," Journal of Clinical Microbiology, 2004, vol. 42 (11), pp. 4947-4955.

Zhang W.D., et al., "Detection and Identification of Human Influenza Viruses by the Polymerase Chain Reaction," Journal of Virological Methods, 1991, vol. 33 (1-2), pp. 165-189.

Zhang Y.Q., et al., "Genome-Based Analysis of Virulence Genes in a Non-Biofilm-Forming *Staphlococcus epidemidis* Strain (ATCC 12228)," Molecular Microbiology, 2003, vol. 49 (6), pp. 1577-1593.

\* cited by examiner

Figure 2

SEQUENCE LISTING

```
<160> NUMBER OF SEQ ID NOS: 77

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
taagttttat ggcggctgg                                                   19

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
tttaggatag tcccaaccca t                                                21
```

-continued

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
tgtttgtttt ggaattgtaa tgttga                                          26

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
tggaatgcat gcttattaac ataca                                           25

<210> SEQ ID NO 5
<211> LENGTH: 83
<212> TYPE: DNA
<213> ORGANISM: Artificial Sequence
<220> FEATURE:
<223> OTHER INFORMATION: Oligonucleotide

<400> SEQUENCE: 5
caagttttac ggtggctggc ataatatgtt aaatttacag tgatgtagaa actccacacc     60
ttatgggttg ggattatcca aaa                                             83

<210> SEQ ID NO 6
<211> LENGTH: 132
<212> TYPE: DNA
<213> ORGANISM: Artificial Sequence
<220> FEATURE:
<223> OTHER INFORMATION: Oligonucleotide

<400> SEQUENCE: 6
tgtttgtttt ggaattgtaa cgttgatcgt tacccagcca atgcaattgt gtgtaggttc     60
aagagtcttg tcaaacttga acttaccagg ctgtgatggt ggtagtttgt atgtgaataa    120
gcatgcattc ca                                                        132

<210> SEQ ID NO 7
<211> LENGTH: 265
<212> TYPE: DNA
<213> ORGANISM: Artificial Sequence
<220> FEATURE:
<223> OTHER INFORMATION: Oligonucleotide

<400> SEQUENCE: 7
tggaacaagc aagttttacg gtggctggca taatatgtta aatttacagt gatgtagaaa     60
ctccacacct tatgggttgg gattatccaa aatgtgacag aggataaatt cactgatggt    120
gtttgtttgt tttggaattg taacgttgat cgttacccag ccaatgcaat tgtgtgtagg    180
ttcaagagtc ttgtcaaact tgaacttacc aggctgtgat ggtggtagtt tgtatgtgaa    240
taagcatgca ttccacactc cagct                                          265

<210> SEQ ID NO 8
<211> LENGTH: 1542
<212> TYPE: DNA

<213> ORGANISM: Artificial Sequence
<220> FEATURE:
<223> OTHER INFORMATION: Oligonucleotide

<400> SEQUENCE: 8

```
aaattgaaga gtttgatcat ggctcagatt gaacgctggc ggcaggccta acacatgcaa      60
gtcgaacggt aacaggaaga agcttgcttc tttgctgacg agtggcggac gggtgagtaa     120
tgtctgggaa actgcctgat ggaggggat aactactgga aacggtagct aataccgcat      180
aacgtcgcaa gaccaaagag ggggaccttc gggcctcttg ccatcggatg tgcccagatg     240
ggattagcta gtaggtgggg taacggctca cctaggcgac gatccctagc tggtctgaga     300
ggatgaccag ccacactgga actgagacac ggtccagact cctacgggag gcagcagtgg     360
ggaatattgc acaatgggcg caagcctgat gcagccatgc cgcgtgtatg aagaaggcct     420
tcgggttgta aagtactttc agcggggagg aagggagtaa agttaatacc tttgctcatt     480
gacgttaccc gcagaagaag caccggctaa ctccgtgcca gcagccgcgg taatacggag     540
ggtgcaagcg ttaatcggaa ttactgggcg taaagcgcac gcaggcggtt tgttaagtca     600
gatgtgaaat ccccgggctc aacctggaa ctgcatctga tactggcaag cttgagtctc      660
gtagaggggg gtagaattcc aggtgtagcg gtgaaatgcg tagagatctg gaggaatacc     720
ggtggcgaag gcggccccct ggacgaagac tgacgctcag gtgcgaaagc gtggggagca     780
aacaggatta gataccctgg tagtccacgc cgtaaacgat gtcgacttgg aggttgtgcc     840
cttgaggcgt ggcttccgga gctaacgcgt taagtcgacc gcctggggag tacggccgca     900
aggttaaaac tcaaatgaat tgacggggc cgcacaagc ggtggagcat gtggtttaat       960
tcgatgcaac gcgaagaacc ttacctggtc ttgacatcca cggaagtttt cagagatgag    1020
aatgtgcctt cgggaaccgt gagacaggtg ctgcatggct gtcgtcagct cgtgttgtga    1080
aatgttgggt taagtcccgc aacgagcgca acccttatcc tttgttgcca gcggtccggc    1140
cgggaactca aaggagactg ccagtgataa actggaggaa ggtggggatg acgtcaagtc    1200
atcatggccc ttacgaccag ggctacacac gtgctacaat ggcgcataca agagaagcg     1260
acctcgcgag agcaagcgga cctcataaag tgcgtcgtag tccggattgg agtctgcaac    1320
tcgactccat gaagtcggaa tcgctagtaa tcgtggatca gaatgccacg gtgaatacgt    1380
tcccgggcct tgtacacacc gcccgtcaca ccatgggagt gggttgcaaa agaagtaggt    1440
agcttaacct tcgggagggc gcttaccact ttgtgattca tgactggggt gaagtcgtaa    1500
caaggtaacc gtaggggaac ctgcggttgg atcacctcct ta                       1542
```

<210> SEQ ID NO 9
<211> LENGTH: 2628
<212> TYPE: DNA
<213> ORGANISM: Artificial Sequence
<220> FEATURE:
<223> OTHER INFORMATION: Oligonucleotide

<400> SEQUENCE: 9

```
gaagtagaga tatggaggaa caccagtggc gaaggcgact ttctggtctg taactgacac      60
tgagaaagcg tggggagcaa acaggattag ataccctggt agtccacgcc gtaaacgatg     120
agtgctaagt gttagaggcc tttagtgctg aagttaacgc attaagcact ccgcctgggg     180
agtacggccg caaggctgaa actcaaagga attgacgggg cacaagcggt ggagcatgtg     240
gtttaattcg aagcaacgcg aagaacctta ccaggtcttg acatcctctg acaacctag     300
cttctccttc gggagcagag tgacaggtgg tgcatggttg tcgtcagctc gtgtcgtgag    360
```

```
atgttgggtt aagtcccgca acgagcgcaa cccttgatct tagttgttta gttgggcact    420
ctaaggtgac tgccggtgac aaaccggagg aaggtgggga tgacgtcaaa tcatcatgcc    480
ccagtaccgt gagggaaagg tgaaaagcac cccggaaggg gagtgaaaga gatcctgaaa    540
ccgtgtgcca tagtcagagc ccgttaacgg gtgatggcgt gccttttgta gaatgaaccg    600
gcgagttata agatccgtag tcaaaaggga aacagcccag accgccagct aaggtcccaa    660
agtgtgtatt gaaaaggatg tggagttgct tagacaacta ggatgttggc ttagaagcag    720
ccaccattta aagagtatag ggggtgacac ctgcccggtg ctggaaggtt aaggagaggg    780
gttagcgtaa ctctgaactg aagccccagt aaacggcggc cgtaactata acggtcctaa    840
ggtagcgaaa gaaatttgag aggagctgtc cttagtacga gggaccggga tggacgcac     900
cggtaccagt tgttctgcca agggcatagc tgggtagcta tgtgcggaag gataagtgc     960
tgaaagcatc taagcatgaa gccccctca agatgagagc agtaaaacaa gcaaacgcac    1020
aatcagaagc taagaaagcg caagcttctg gaaagcacaa atgctagtta tggtacagaa   1080
tttgcaactg aaacagacgt gcatgctgtg aaatttgcga agcttttgc atattatatc    1140
gagccacagc atcgtgatgt tttacagctt tatgcaccgg aagcttttaa tggataaatt   1200
taacgaacaa gaaataaatc tatccttgga agaacttaaa gatcaacgga tgctggcaag   1260
atatgaaaaa taagataaaa cagcactatc aacactggag cgattcttta tctgaagaag   1320
gaagagcgat gaaaacaacg aagtacaata caagacaaaa gaaggtaaaa ttactgtttt   1380
aggggaaaaa ttcaagaaat atagaagtga tggctaaaaa tgtagaaggg gtcttgaagc   1440
cgttaacagc tgttatggcg accgtggcgg cgtggttatc gaacccatgc tgaccgatca   1500
atggtacgtg cacaccgccc cccaaagtcg cgattgaagc cgtagagaac ggcgagatcc   1560
agttcgtccc taaacagtac ggcaacttcg ttatcgctca ggcgaactcc aacctggatg   1620
atgaaggccg cttttttagaa ggtgacttgt cgtagcaaag gcgaatcaag cctgtttagc   1680
cacaactatg cgtgctcgtg gtgcacaagt aacggatatt acaatcattg ttgttgcagc   1740
tgatgacggc gtaataaaca gttgaagcga ttaaccatgc gaaagcagca ggagtaccaa   1800
ctttactcag cttgctggta tgcgtggtct gatggccaat ccatctggtc gtatcatcga   1860
acttccaatc aagtttccgt gaaggtttaa cagtacttga gtacttcatc tctacgcatg   1920
gtgcgcgtaa aggtcatggg agtaagacct acagtaagag gttctgtaat gaaccctaat   1980
gaccatccac acggtggtgg tgaaggtaga tctcctatcg gaaagtccac gtactccatg   2040
gggtaaacca gcacttggat acaaaacaag cgcagttcgg cggccagcgc ttcggtgaaa   2100
tggaagtggc tcgaagcgta tggcgcttcg tacgtgctgc aggaaatgct gacggtgaag   2160
tcggacgacg tgaccggacg cgccaggaat cgttcaactc gatctacatg atggccgacc   2220
gcccggggtt cggcggtgca gattcgtcag ctggccggca tgcgcggcct gatggcgaag   2280
ccggacgcgc cgttcaacgc cgacttcgac ggtgaccagc gttcacgtgc cgctgtcgct   2340
cgaagcgcag atggaagcgc gcacgctgat gctcgcgtcg aacaacgacg aaggcggccg   2400
ccacacgccg ttcttcaaca actaccgtgt tctacttccg tacgacggac gtgacgggct   2460
cgatcgagct gccgaaggac aaggaaatgg tgatgccggg cgacaacact tttatttgat   2520
tattgttatc ctgttatgcc atttgagatt tttgagtggt attggagtta tgttccagg    2580
attaattgca aatacaattc aaagacaagg gttaccatta acaatcat                2628
```

<210> SEQ ID NO 10

```
<211> LENGTH: 21
<212> TYPE: DNA
<213> ORGANISM: Artificial Sequence
<220> FEATURE:
<223> OTHER INFORMATION: Primer

<400> SEQUENCE: 10
tagaacaccg atggcgaagg c                                            21

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
tcgtggacta ccagggtatc ta                                           22

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
tggattagag accctggtag tcc                                          23

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
tggccgtact ccccaggcg                                               19

<210> SEQ ID NO 14
<211> LENGTH: 108
<212> TYPE: DNA
<213> ORGANISM: Artificial Sequence
<220> FEATURE:
<223> OTHER INFORMATION: Oligonucleotide

<400> SEQUENCE: 14
tggattagag accctggtag tccacgccgt aaacgatgag tgctaagtgt tagaggcctt   60
tagtgctgaa gttaacgcat taagcactcc gcctggggag tacggcca              108

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
tttcgatgca acgcgaagaa cct                                          23

<210> SEQ ID NO 16
<211> LENGTH: 21
<212> TYPE: DNA
<213> ORGANISM: Artificial Sequence
<220> FEATURE:
<223> OTHER INFORMATION: Primer
```

<400> SEQUENCE: 16
tacgagctga cgacagccat g                                          21

<210> SEQ ID NO 17
<211> LENGTH: 108
<212> TYPE: DNA
<213> ORGANISM: Artificial Sequence
<220> FEATURE:
<223> OTHER INFORMATION: Oligonucleotide

<400> SEQUENCE: 17
tttcgatgca acgcgaagaa ccttaccagg tcttgacatc ctctgacaac cctagcttct    60
ccttcgggag cagagtgaca ggtggtgcat ggctgtcgtc agctcgta              108

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
tctgacacct gcccggtgc                                             19

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tgaccgttat agttacggcc                                            20

<210> SEQ ID NO 20
<211> LENGTH: 95
<212> TYPE: DNA
<213> ORGANISM: Artificial Sequence
<220> FEATURE:
<223> OTHER INFORMATION: Oligonucleotide

<400> SEQUENCE: 20
tctgacacct gcccggtgct ggaaggttaa ggagaggggt tagcgtaact ctgaactgaa    60
gccccagtaa acggcggccg taactataac ggtca                            95

<210> SEQ ID NO 21
<211> LENGTH: 31
<212> TYPE: DNA
<213> ORGANISM: Artificial Sequence
<220> FEATURE:
<223> OTHER INFORMATION: Primer

<400> SEQUENCE: 21
tgattattgt tatcctgtta tgccatttga g                               31

<210> SEQ ID NO 22
<211> LENGTH: 29
<212> TYPE: DNA
<213> ORGANISM: Artificial Sequence
<220> FEATURE:
<223> OTHER INFORMATION: Primer

<400> SEQUENCE: 22

```
tgtaaccctt gtctttgaat tgtatttgc                                        29
```

<210> SEQ ID NO 23
<211> LENGTH: 100
<212> TYPE: DNA
<213> ORGANISM: Artificial Sequence
<220> FEATURE:
<223> OTHER INFORMATION: Oligonucleotide

<400> SEQUENCE: 23

```
tgattattgt tatcctgtta tgccatttga gatttttgag tggtattgga gttattgttc      60
caggattaat tgcaaataca attcaaagac aagggttaca                            100
```

<210> SEQ ID NO 24
<211> LENGTH: 28
<212> TYPE: DNA
<213> ORGANISM: Artificial Sequence
<220> FEATURE:
<223> OTHER INFORMATION: Primer

<400> SEQUENCE: 24

```
tcgaagtaca atacaagaca aaagaagg                                         28
```

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25

```
ttgttaacgg cttcaagacc c                                                21
```

<210> SEQ ID NO 26
<211> LENGTH: 112
<212> TYPE: DNA
<213> ORGANISM: Artificial Sequence
<220> FEATURE:
<223> OTHER INFORMATION: Oligonucleotide

<400> SEQUENCE: 26

```
tcgaagtaca atacaagaca aaagaaggta aaattactgt tttaggggaa aaattcaaga      60
aatatagaag tgatggctaa aaatgtagaa ggggtcttga agccgttaac aa              112
```

<210> SEQ ID NO 27
<211> LENGTH: 30
<212> TYPE: DNA
<213> ORGANISM: Artificial Sequence
<220> FEATURE:
<223> OTHER INFORMATION: Primer

<400> SEQUENCE: 27

```
ttgctcgtgg tgcacaagta acggatatta                                       30
```

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28

```
ttgctgcttt cgcatggtta attgcttcaa                                       30
```

<210> SEQ ID NO 29
<211> LENGTH: 100
<212> TYPE: DNA
<213> ORGANISM: Artificial Sequence
<220> FEATURE:
<223> OTHER INFORMATION: Oligonucleotide

<400> SEQUENCE: 29
ttgctcgtgg tgcacaagta acggatatta caatcattgt tgttgcagct gatgacggcg    60
taataaacag ttgaagcaat taaccatgcg aaagcagcaa                          100

<210> SEQ ID NO 30
<211> LENGTH: 27
<212> TYPE: DNA
<213> ORGANISM: Artificial Sequence
<220> FEATURE:
<223> OTHER INFORMATION: Primer

<400> SEQUENCE: 30
tagcttttgc atattatatc gagccac                                        27

<210> SEQ ID NO 31
<211> LENGTH: 31
<212> TYPE: DNA
<213> ORGANISM: Artificial Sequence
<220> FEATURE:
<223> OTHER INFORMATION: Primer

<400> SEQUENCE: 31
ttcttccaag gatagattta tttcttgttc g                                   31

<210> SEQ ID NO 32
<211> LENGTH: 114
<212> TYPE: DNA
<213> ORGANISM: Artificial Sequence
<220> FEATURE:
<223> OTHER INFORMATION: Oligonucleotide

<400> SEQUENCE: 32
tagcttttgc atattatatc gagccacagc atcgtgatgt tttacagctt tatgcaccgg    60
aagcttttaa tggataaatt taacgaacaa gaaataaatc tatccttgga agaa          114

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
tctggcaggt atgcgtggtc tgatg                                          25

<210> SEQ ID NO 34
<211> LENGTH: 26
<212> TYPE: DNA
<213> ORGANISM: Artificial Sequence
<220> FEATURE:
<223> OTHER INFORMATION: Primer

<400> SEQUENCE: 34
tcgcaccgtg ggttgagatg aagtac                                         26

<210> SEQ ID NO 35
<211> LENGTH: 117
<212> TYPE: DNA

<213> ORGANISM: Artificial Sequence
<220> FEATURE:
<223> OTHER INFORMATION: Oligonucleotide

<400> SEQUENCE: 35
tctggcaggt atgcgtggtc tgatggccaa tccatctggt cgtatcatcg aacttccaat    60
caagtttccg tgaaggttta acagtacttg agtacttcat ctcaacccac ggtgcga      117

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
tcaagcaaac gcacaatcag aagc                                           24

<210> SEQ ID NO 37
<211> LENGTH: 27
<212> TYPE: DNA
<213> ORGANISM: Artificial Sequence
<220> FEATURE:
<223> OTHER INFORMATION: Primer

<400> SEQUENCE: 37
ttgcacgtct gtttcagttg caaattc                                        27

<210> SEQ ID NO 38
<211> LENGTH: 98
<212> TYPE: DNA
<213> ORGANISM: Artificial Sequence
<220> FEATURE:
<223> OTHER INFORMATION: Oligonucleotide

<400> SEQUENCE: 38
tcaagcaaac gcacaatcag aagctaagaa agcgcaagct tctggaaagc acaaatgcta    60
gttatggtac agaatttgca actgaaacag acgtgcaa                            98

<210> SEQ ID NO 39
<211> LENGTH: 31
<212> TYPE: DNA
<213> ORGANISM: Artificial Sequence
<220> FEATURE:
<223> OTHER INFORMATION: Primer

<400> SEQUENCE: 39
tgacctacag taagaggttc tgtaatgaac c                                   31

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
ttccaagtgc tggtttaccc catgg                                          25

<210> SEQ ID NO 41
<211> LENGTH: 116
<212> TYPE: DNA
<213> ORGANISM: Artificial Sequence
<220> FEATURE:
<223> OTHER INFORMATION: Oligonucleotide -continued

<400> SEQUENCE: 41
tgacctacag taagaggttc tgtaatgaac cctaatgacc atccacacgg tggtggtgaa    60
ggtagatctc ctatcggaaa gtccacgtac tccatggggt aaaccagcac ttggaa       116

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
tcgtggcggc gtggttatcg a                                              21

<210> SEQ ID NO 43
<211> LENGTH: 25
<212> TYPE: DNA
<213> ORGANISM: Artificial Sequence
<220> FEATURE:
<223> OTHER INFORMATION: Primer

<400> SEQUENCE: 43
tcggtacgaa ctggatgtcg ccgtt                                          25

<210> SEQ ID NO 44
<211> LENGTH: 111
<212> TYPE: DNA
<213> ORGANISM: Artificial Sequence
<220> FEATURE:
<223> OTHER INFORMATION: Oligonucleotide

<400> SEQUENCE: 44
tcgtggcggc gtggttatcg aacccatgct gaccgatcaa tggtacgtgc acaccgcccc    60
ccaaagtcgc gattgaagcc gtagagaacg gcgacatcca gttcgtaccg a            111

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
ttatcgctca ggcgaactcc aac                                            23

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
tgctggattc gcctttgcta cg                                             22

<210> SEQ ID NO 47
<211> LENGTH: 82
<212> TYPE: DNA
<213> ORGANISM: Artificial Sequence
<220> FEATURE:
<223> OTHER INFORMATION: Oligonucleotide

<400> SEQUENCE: 47

```
ttatcgctca ggcgaactcc aacctggatg atgaaggccg cttttttagaa ggtgacttgt    60 cgtagcaaag gcgaatccag ca                                             82
```

<210> SEQ ID NO 48
<211> LENGTH: 23
<212> TYPE: DNA
<213> ORGANISM: Artificial Sequence
<220> FEATURE:
<223> OTHER INFORMATION: Primer

<400> SEQUENCE: 48

```
tctgttctta gtacgagagg acc                                            23
```

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49

```
tttcgtgctt agatgctttc ag                                             22
```

<210> SEQ ID NO 50
<211> LENGTH: 117
<212> TYPE: DNA
<213> ORGANISM: Artificial Sequence
<220> FEATURE:
<223> OTHER INFORMATION: Oligonucleotide

<400> SEQUENCE: 50

```
tctgttctta gtacgagagg accgggatgg acgcaccggt accagttgtt ctgccaaggg    60
catagctggg tagctatgtg cggaagggat aagtgctgaa agcatctaag cacgaaa      117
```

<210> SEQ ID NO 51
<211> LENGTH: 23
<212> TYPE: DNA
<213> ORGANISM: Artificial Sequence
<220> FEATURE:
<223> OTHER INFORMATION: Primer

<400> SEQUENCE: 51

```
tttaagtccc gcaacgagcg caa                                            23
```

<210> SEQ ID NO 52
<211> LENGTH: 23
<212> TYPE: DNA
<213> ORGANISM: Artificial Sequence
<220> FEATURE:
<223> OTHER INFORMATION: Primer

<400> SEQUENCE: 52

```
ttgacgtcat ccccaccttc ctc                                            23
```

<210> SEQ ID NO 53
<211> LENGTH: 102
<212> TYPE: DNA
<213> ORGANISM: Artificial Sequence
<220> FEATURE:
<223> OTHER INFORMATION: Oligonucleotide

<400> SEQUENCE: 53

```
tttaagtccc gcaacgagcg caacccttga tcttagttgt ttagttgggc actctaaggt    60
gactgccggt gacaaaccgg aggaaggtgg ggatgacgtc aa                      102
```

<210> SEQ ID NO 54
<211> LENGTH: 24
<212> TYPE: DNA
<213> ORGANISM: Artificial Sequence
<220> FEATURE:
<223> OTHER INFORMATION: Primer

<400> SEQUENCE: 54
tgggcagcgt tcggcgaaa tgga                                           24

<210> SEQ ID NO 55
<211> LENGTH: 28
<212> TYPE: DNA
<213> ORGANISM: Artificial Sequence
<220> FEATURE:
<223> OTHER INFORMATION: Primer

<400> SEQUENCE: 55
tgtccgactt gacggtcaac atttcctg                                      28

<210> SEQ ID NO 56
<211> LENGTH: 87
<212> TYPE: DNA
<213> ORGANISM: Artificial Sequence
<220> FEATURE:
<223> OTHER INFORMATION: Oligonucleotide

<400> SEQUENCE: 56
tgggcagcgt tcggcgaaa tggaagtggc tcgaagcgta tggcgcttcg tacgtgctgc    60
aggaaatgtt gaccgtcaag tcggaca                                       87

<210> SEQ ID NO 57
<211> LENGTH: 30
<212> TYPE: DNA
<213> ORGANISM: Artificial Sequence
<220> FEATURE:
<223> OTHER INFORMATION: Primer

<400> SEQUENCE: 57
tcaggagtcg ttcaactcga tctacatgat                                    30

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
tacgccatca ggccacgcat                                               20

<210> SEQ ID NO 59
<211> LENGTH: 97
<212> TYPE: DNA
<213> ORGANISM: Artificial Sequence
<220> FEATURE:
<223> OTHER INFORMATION: Oligonucleotide

<400> SEQUENCE: 59
tcaggagtcg ttcaactcga tctacatgat ggccgaccgc ccggggttcg gcggtgcaga   60
ttcgtcagct ggccggcatg cgtggcctga tggcgta                            97

<210> SEQ ID NO 60

-continued

```
<211> LENGTH: 24
<212> TYPE: DNA
<213> ORGANISM: Artificial Sequence
<220> FEATURE:
<223> OTHER INFORMATION: Primer

<400> SEQUENCE: 60
tccacacgcc gttcttcaac aact                                          24

<210> SEQ ID NO 61
<211> LENGTH: 26
<212> TYPE: DNA
<213> ORGANISM: Artificial Sequence
<220> FEATURE:
<223> OTHER INFORMATION: Primer

<400> SEQUENCE: 61
tggcatcacc atttccttgt ccttcg                                        26

<210> SEQ ID NO 62
<211> LENGTH: 99
<212> TYPE: DNA
<213> ORGANISM: Artificial Sequence
<220> FEATURE:
<223> OTHER INFORMATION: Oligonucleotide

<400> SEQUENCE: 62
tccacacgcc gttcttcaac aactaccgtg ttctacttcc gtacgacgga cgtgacgggc   60
tcgatcgagc tgccgaagga caaggaaatg gtgatgcca                          99

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
tccacacggt ggtggtgaag g                                             21

<210> SEQ ID NO 64
<211> LENGTH: 22
<212> TYPE: DNA
<213> ORGANISM: Artificial Sequence
<220> FEATURE:
<223> OTHER INFORMATION: Primer

<400> SEQUENCE: 64
tgtgctggtt taccccatgg ag                                            22

<210> SEQ ID NO 65
<211> LENGTH: 70
<212> TYPE: DNA
<213> ORGANISM: Artificial Sequence
<220> FEATURE:
<223> OTHER INFORMATION: Oligonucleotide

<400> SEQUENCE: 65
tccacacggt ggtggtgaag gtagatctcc tatcggaaag tccacgtact ccatggggta   60
aaccagcaca                                                          70

<210> SEQ ID NO 66
<211> LENGTH: 1542
<212> TYPE: DNA
<213> ORGANISM: E. coli
```

<400> SEQUENCE: 66

```
aaattgaaga gtttgatcat ggctcagatt gaacgctggc ggcaggccta acacatgcaa      60
gtcgaacggt aacaggaaga agcttgcttc tttgctgacg agtggcggac gggtgagtaa     120
tgtctgggaa actgcctgat ggaggggggat aactactgga aacggtagct aataccgcat    180
aacgtcgcaa gaccaaagag ggggaccttc gggcctcttg ccatcggatg tgcccagatg    240
ggattagcta gtaggtgggg taacggctca cctaggcgac gatccctagc tggtctgaga    300
ggatgaccag ccacactgga actgagacac ggtccagact cctacgggag gcagcagtgg    360
ggaatattgc acaatgggcg caagcctgat gcagccatgc cgcgtgtatg aagaaggcct    420
tcgggttgta aagtactttc agcggggagg aagggagtaa agttaatacc tttgctcatt    480
gacgttaccc gcagaagaag caccggctaa ctccgtgcca gcagccgcgg taatacggag    540
ggtgcaagcg ttaatcggaa ttactgggcg taaagcgcac gcaggcggtt tgttaagtca    600
gatgtgaaat ccccgggctc aacctggaa ctgcatctga tactggcaag cttgagtctc     660
gtagaggggg gtagaattcc aggtgtagcg gtgaaatgcg tagagatctg gaggaatacc    720
ggtggcgaag gcggccccct ggacgaagac tgacgctcag gtgcgaaagc gtggggagca    780
aacaggatta gataccctgg tagtccacgc cgtaaacgat gtcgacttgg aggttgtgcc    840
cttgaggcgt ggcttccgga gctaacgcgt taagtcgacc gcctggggag tacggccgca    900
aggttaaaac tcaaatgaat tgacggggggc ccgcacaagc ggtggagcat gtggtttaat    960
tcgatgcaac gcgaagaacc ttacctggtc ttgacatcca cggaagtttt cagagatgag   1020
aatgtgcctt cgggaaccgt gagacaggtg ctgcatggct gtcgtcagct cgtgttgtga   1080
aatgttgggt taagtcccgc aacgagcgca acccttatcc tttgttgcca gcggtccggc   1140
cgggaactca aaggagactg ccagtgataa actggaggaa ggtgggggatg acgtcaagtc   1200
atcatggccc ttacgaccag ggctacacac gtgctacaat ggcgcataca agagaaagcg   1260
acctcgcgag agcaagcgga cctcataaag tgcgtcgtag tccggattgg agtctgcaac   1320
tcgactccat gaagtcggaa tcgctagtaa tcgtggatca gaatgccacg gtgaatacgt   1380
tcccgggcct tgtacacacc gcccgtcaca ccatgggagt gggttgcaaa agaagtaggt   1440
agcttaacct tcgggagggc gcttaccact ttgtgattca tgactggggt gaagtcgtaa   1500
caaggtaacc gtaggggaac ctgcggttgg atcacctcct ta                       1542
```

<210> SEQ ID NO 67
<211> LENGTH: 2904
<212> TYPE: DNA
<213> ORGANISM: E. coli

<400> SEQUENCE: 67

```
ggttaagcga ctaagcgtac acggtggatg ccctggcagt cagaggcgat gaaggacgtg     60
ctaatctgcg ataagcgtcg gtaaggtgat atgaaccgtt ataaccggcg atttccgaat    120
ggggaaaccc agtgtgtttc gacacactat cattaactga atccataggt taatgaggcg    180
aaccggggga actgaaacat ctaagtaccc cgaggaaaag aaatcaaccg agattccccc    240
agtagcggcg agcgaacggg gagcagccca gagcctgaat cagtgtgtgt gttagtggaa    300
gcgtctggaa aggcgcgcga tacagggtga cagccccgta cacaaaaatg cacatgctgt    360
gagctcgatg agtagggcgg gacacgtggt atcctgtctg aatatggggg gaccatcctc    420
caaggctaaa tactcctgac tgaccgatag tgaaccagta ccgtgaggga aaggcgaaaa    480
```

```
gaaccccggc gagggagtg aaaaagaacc tgaaaccgtg tacgtacaag cagtgggagc    540
acgcttaggc gtgtgactgc gtaccttttg tataatgggt cagcgactta tattctgtag    600
caaggttaac cgatagggg agccgaaggg aaaccgagtc ttaactgggc gttaagttgc    660
agggtataga cccgaaaccc ggtgatctag ccatgggcag gttgaaggtt gggtaacact    720
aactggagga ccgaaccgac taatgttgaa aaattagcgg atgacttgtg gctggggtg     780 aaaggccaat caaaccggga gatagctggt tctccccgaa agctatttag gtagcgcctc    840
gtgaattcat ctccgggggt agagcactgt ttcggcaagg gggtcatccc gacttaccaa    900
cccgatgcaa actgcgaata ccggagaatg ttatcacggg agacacacgg cgggtgctaa    960
cgtccgtcgt gaagagggaa acaacccaga ccgccagcta aggtcccaaa gtcatggtta   1020
agtgggaaac gatgtgggaa ggcccagaca gccaggatgt tggcttagaa gcagccatca   1080 tttaagaaa gcgtaatagc tcactggtcg agtcggcctg cgcggaagat gtaacggggc    1140
taaaccatgc accgaagctg cggcagcgac gcttatgcgt tgttgggtag gggagcgttc   1200
tgtaagcctg cgaaggtgtg ctgtgaggca tgctggaggt atcagaagtg cgaatgctga   1260
cataagtaac gataaagcgg gtgaaaagcc cgctcgccgg aagaccaagg gttcctgtcc   1320
aacgttaatc ggggcagggt gagtcgaccc ctaaggcgag gccgaaaggc gtagtcgatg   1380
ggaaacaggt taatattcct gtacttggtg ttactgcgaa gggggacgg agaaggctat     1440 gttggccggc gacgttgt cccggtttaa gcgtgtaggc tggttttcca ggcaaatccg      1500
gaaaatcaag gctgaggcgt gatgacgagg cactacggtg ctgaagcaac aaatgccctg   1560
cttccaggaa aagcctctaa gcatcaggta acatcaaatc gtaccccaaa ccgacacagg   1620
tggtcaggta gagaatacca aggcgcttga gagaactcgg gtgaaggaac taggcaaaat   1680
ggtgccgtaa cttcgggaga aggcacgctg atatgtaggt gaggtccctc gcggatggag   1740
ctgaaatcag tcgaagatac cagctggctg caactgttta ttaaaaacac agcactgtgc   1800
aaacacgaaa gtggacgtat acggtgtgac gcctgcccgg tgccggaagg ttaattgatg   1860
gggttagcgc aagcgaagct cttgatcgaa gccccggtaa acggcggccg taactataac   1920
ggtcctaagg tagcgaaatt ccttgtcggg taagttccga cctgcacgaa tggcgtaatg   1980
atggccaggc tgtctccacc cgagactcag tgaaattgaa ctcgctgtga agatgcagtg   2040
tacccgcggc aagacggaaa gaccccgtga acctttacta tagcttgaca ctgaacattg   2100
agccttgatg tgtaggatag gtgggaggct ttgaagtgtg gacgccagtc tgcatggagc   2160
cgaccttgaa ataccaccct ttaatgtttg atgttctaac gttgacccgt aatccgggtt   2220
gcggacagtg tctggtgggt agtttgactg gggcggtctc ctcctaaaga gtaacggagg   2280
agcacgaagg ttggctaatc ctggtcggac atcaggaggt tagtgcaatg gcataagcca   2340
gcttgactgc gagcgtgacg gcgcgagcag gtgcgaaagc aggtcatagt gatccggtgg   2400
ttctgaatgg aagggccatc gctcaacgga taaaaggtac tccggggata acaggctgat   2460
accgcccaag agttcatatc gacggcggtg tttggcacct cgatgtcggc tcatcacatc   2520
ctggggctga agtaggtccc aagggtatgg ctgttcgcca tttaaagtgg tacgcgagct   2580
gggtttagaa cgtcgtgaga cagttcggtc cctatctgcc gtgggcgctg gagaactgag   2640
gggggctgct cctagtacga gggaccgga gtggacgcat cactggtgtt cgggttgtca   2700
tgccaatggc actgcccggt agctaaatgc ggaagagata agtgctgaaa gcatctaagc   2760
acgaaacttg ccccgagatg agttctccct gacccttaa gggtcctgaa ggaacgttga   2820
agacgacgac gttgataggc cgggtgtgta agcgcagcga tgcgttgagc taaccggtac   2880
```
taatgaaccg tgaggcttaa cctt                                              2904

<210> SEQ ID NO 68
<211> LENGTH: 4029
<212> TYPE: DNA
<213> ORGANISM: E. coli

<400> SEQUENCE: 68

| | | | | | |
|---|---|---|---|---|---|
| atggtttact | cctataccga | gaaaaaacgt | attcgtaagg | attttggtaa | acgtccacaa | 60 |
| gttctggatg | taccttatct | cctttctatc | cagcttgact | cgtttcagaa | atttatcgag | 120 |
| caagatcctg | aagggcagta | tggtctggaa | gctgctttcc | gttccgtatt | cccgattcag | 180 |
| agctacagcg | gtaattccga | gctgcaatac | gtcagctacc | gccttggcga | accggtgttt | 240 |
| gacgtccagg | aatgtcaaat | ccgtggcgtg | acctattccg | caccgctgcg | cgttaaactg | 300 |
| cgtctggtga | tctatgagcg | cgaagcgccg | gaaggcaccg | taaaagacat | taagaacaa | 360 |
| gaagtctaca | tgggcgaaat | tccgctcatg | acagacaacg | gtacctttgt | tatcaacggt | 420 |
| actgagcgtg | ttatcgtttc | ccagctgcac | cgtagtccgg | gcgtcttctt | tgactccgac | 480 |
| aaaggtaaaa | cccactcttc | gggtaaagtg | ctgtataacg | cgcgtatcat | cccttaccgt | 540 |
| ggttcctggc | tggacttcga | attcgatccg | aaggacaacc | tgttcgtacg | tatcgaccgt | 600 |
| cgccgtaaac | tgcctgcgac | catcattctg | cgcgccctga | actacaccac | agagcagatc | 660 |
| ctcgacctgt | tctttgaaaa | agttatcttt | gaaatccgtg | ataacaagct | gcagatggaa | 720 |
| ctggtgccgg | aacgcctgcg | tggtgaaacc | gcatcttttg | acatcgaagc | taacggtaaa | 780 |
| gtgtacgtag | aaaaaggccg | ccgtatcact | gcgcgccaca | ttcgccagct | ggaaaaagac | 840 |
| gacgtcaaac | tgatcgaagt | cccggttgag | tacatcgcag | gtaaagtggt | tgctaaagac | 900 |
| tatattgatg | agtctaccgg | cgagctgatc | tgcgcagcga | acatggagct | gagcctggat | 960 |
| ctgctggcta | agctgagcca | gtctggtcac | aagcgtatcg | aaacgctgtt | caccaacgat | 1020 |
| ctggatcacg | gcccatatat | ctctgaaacc | ttacgtgtcg | acccaactaa | cgaccgtctg | 1080 |
| agcgcactgg | tagaaatcta | ccgcatgatg | cgccctggcg | agccgccgac | tcgtgaagca | 1140 |
| gctgaaagcc | tgttcgagaa | cctgttcttc | tccgaagacc | gttatgactt | gtctgcggtt | 1200 |
| ggtcgtatga | agttcaaccg | ttctctgctg | cgcgaagaaa | tcgaaggttc | cggtatcctg | 1260 |
| agcaaagacg | acatcattga | tgttatgaaa | aagctcatcg | atatccgtaa | cggtaaaggc | 1320 |
| gaagtcgatg | atatcgacca | cctcggcaac | cgtcgtatcc | gttccgttgg | cgaaatggcg | 1380 |
| gaaaaccagt | tccgcgttgg | cctggtacgt | gtagagcgtg | cggtgaaaga | gcgtctgtct | 1440 |
| ctgggcgatc | tggataccct | gatgccacag | gatatgatca | acgccaagcc | gatttccgca | 1500 |
| gcagtgaaag | agttcttcgg | ttccagccag | ctgtctcagt | ttatggacca | gaacaacccg | 1560 |
| ctgtctgaga | ttacgcacaa | acgtcgtatc | tccgcactcg | gcccaggcgg | tctgacccgt | 1620 |
| gaacgtgcag | gcttcgaagt | tcgagacgta | caccgactc | actacggtcg | cgtatgtcca | 1680 |
| atcgaaaccc | ctgaaggtcc | gaacatcggt | ctgatcaact | ctctgtccgt | gtacgcacag | 1740 |
| actaacgaat | acggcttcct | tgagactccg | tatcgtaaag | tgaccgacgg | tgttgtaact | 1800 |
| gacgaaattc | actacctgtc | tgctatcgaa | gaaggcaact | acgttatcgc | ccaggcgaac | 1860 |
| tccaacttgg | atgaagaagg | ccacttcgta | gaagacctgg | taacttgccg | tagcaaaggc | 1920 |
| gaatccagct | tgttcagccg | cgaccaggtt | gactacatgg | acgtatccac | ccagcaggtg | 1980 |
| gtatccgtcg | gtgcgtccct | gatcccgttc | ctggaacacg | atgacgccaa | ccgtgcattg | 2040 |

| | |
|---|---|
| atgggtgcga acatgcaacg tcaggccgtt ccgactctgc gcgctgataa gccgctggtt | 2100 |
| ggtactggta tggaacgtgc tgttgccgtt gactccggtg taactgcggt agctaaacgt | 2160 |
| ggtggtgtcg ttcagtacgt ggatgcttcc cgtatcgtta tcaaagttaa cgaagacgag | 2220 |
| atgtatccgg gtgaagcagg tatcgacatc tacaacctga ccaaatacac ccgttctaac | 2280 |
| cagaacacct gtatcaacca gatgccgtgt gtgtctctgg gtgaaccggt tgaacgtggc | 2340 |
| gacgtgctgg cagacggtcc gtccaccgac ctcggtgaac tggcgcttgg tcagaacatg | 2400 |
| cgcgtagcgt tcatgccgtg aatggttac aacttcgaag actccatcct cgtatccgag | 2460 |
| cgtgttgttc aggaagaccg tttcaccacc atccacattc aggaactggc gtgtgtgtcc | 2520 |
| cgtgacacca gctgggtcc ggaagagatc accgctgaca tcccgaacgt gggtgaagct | 2580 |
| gcgctctcca aactggatga atccggtatc gtttacattg gtgcggaagt gaccggtggc | 2640 |
| gacattctgg ttggtaaggt aacgccgaaa ggtgaaactc agctgacccc agaagaaaaa | 2700 |
| ctgctgcgtg cgatcttcgg tgagaaagcc tctgacgtta agactcttc tctgcgcgta | 2760 |
| ccaaacggtg tatccggtac ggttatcgac gttcaggtct ttactcgcga tggcgtagaa | 2820 |
| aaagacaaac gtcgctgga atcgaagaa atgcagctca acaggcgaa gaaagacctg | 2880 |
| tctgaagaac tgcagatcct cgaagcgggt ctgttcagcc gtatccgtgc tgtgctggta | 2940 |
| gccggtggcg ttgaagctga aagctcgac aaactgccgc gcgatcgctg gctggagctg | 3000 |
| ggcctgacag acgaagagaa acaaaatcag ctggaacagc tggctgagca gtatgacgaa | 3060 |
| ctgaaacacg agttcgagaa gaaactcgaa gcgaaacgcc gcaaaatcac ccagggcgac | 3120 |
| gatctggcac cgggcgtgct gaagattgtt aaggtatatc tggcggttaa acgccgtatc | 3180 |
| cagcctggtg acaagatggc aggtcgtcac ggtaacaagg gtgtaatttc taagatcaac | 3240 |
| ccgatcgaag atatgccta cgatgaaaac ggtacgccgg tagacatcgt actgaacccg | 3300 |
| ctgggcgtac cgtctcgtat gaacatcggt cagatcctcg aaacccacct gggtatggct | 3360 |
| gcgaaaggta tcggcgacaa gatcaacgcc atgctgaaaac agcagcaaga gtcgcgaaa | 3420 |
| ctgcgcgaat tcatccagcg tgcgtacgat ctgggcgctg acgttcgtca gaaagttgac | 3480 |
| ctgagtacct tcagcgatga agaagttatg cgtctggctg aaaacctgcg caaaggtatg | 3540 |
| ccaatcgcaa cgccggtgtt cgacggtgcg aaagaagcag aaattaaaga gctgctgaaa | 3600 |
| cttggcgacc tgccgacttc cggtcagatc cgcctgtacg atggtcgcac tggtgaacag | 3660 |
| ttcgagcgtc cggtaaccgt tggttacatg tacatgctga aactgaacca cctggtcgac | 3720 |
| gacaagatgc acgcgcgttc caccggttct tacagcctgg ttactcagca gccgctgggt | 3780 |
| ggtaaggcac agttcggtgg tcagcgtttc ggggagatgg aagtgtgggc gctggaagca | 3840 |
| tacgcgcag catacaccct gcaggaaatg ctcaccgtta agtctgatga cgtgaacggt | 3900 |
| cgtaccaaga tgtataaaaa catcgtggac ggcaaccatc agatggagcc gggcatgcca | 3960 |
| gaatccttca acgtattgtt gaaagagatt cgttcgctgg gtatcaacat cgaactggaa | 4020 |
| gacgagtaa | 4029 |

<210> SEQ ID NO 69
<211> LENGTH: 4096
<212> TYPE: DNA
<213> ORGANISM: E. coli
<400> SEQUENCE: 69

| | |
|---|---|
| gtgaaagatt tattaaagtt tctgaaagcg cagactaaaa ccgaagagtt tgatgcgatc | 60 |
| aaaattgctc tggcttcgcc agacatgatc cgttcatggt ctttcggtga agttaaaaag | 120 |

| | |
|---|---|
| ccggaaaacca tcaactaccg tacgttcaaa ccagaacgtg acggccttt ctgcgcccgt | 180 |
| atctttgggc cggtaaaaga ttacgagtgc ctgtgcggta agtacaagcg cctgaaacac | 240 |
| cgtggcgtca tctgtgagaa gtgcggcgtt gaagtgaccc agactaaagt acgccgtgag | 300 |
| cgtatgggcc acatcgaact ggcttccccg actgcgcaca tctggttcct gaaatcgctg | 360 |
| ccgtcccgta tcggtctgct gctcgatatg ccgctgcgcg atatcgaacg cgtactgtac | 420 |
| tttgaatcct atgtggttat cgaaggcggt atgaccaacc tggaacgtca gcagatcctg | 480 |
| actgaagagc agtatctgga cgcgctggaa gagttcggtg acgaattcga cgcgaagatg | 540 |
| ggggcggaag caatccaggc tctgctgaag agcatggatc tggagcaaga gtgcgaacag | 600 |
| ctgcgtgaag agctgaacga aaccaactcc gaaaccaagc gtaaaaagct gaccaagcgt | 660 |
| atcaaactgc tggaagcgtt cgttcagtct ggtaacaaac cagagtggat gatcctgacc | 720 |
| gttctgccgg tactgccgcc agatctgcgt ccgctggttc cgctggatgg tggtcgtttc | 780 |
| gcgacttctg acctgaacga tctgtatcgt cgcgtcatta accgtaacaa ccgtctgaaa | 840 |
| cgtctgctgg atctggctgc gccggacatc atcgtacgta acgaaaaacg tatgctgcag | 900 |
| gaagcggtag acgccctgct ggataacggt cgtcgcggtc gtgcgatcac cggttctaac | 960 |
| aagcgtcctc tgaaatcttt ggccgacatg atcaaaggta acagggtcg tttccgtcag | 1020 |
| aacctgctcg gtaagcgtgt tgactactcc ggtcgttctg taatcaccgt aggtccatac | 1080 |
| ctgcgtctgc atcagtgcgg tctgccgaag aaaatggcac tggagctgtt caaaccgttc | 1140 |
| atctacggca agctggaact gcgtggtctt gctaccacca ttaaagctgc gaagaaaatg | 1200 |
| gttgagcgcg aagaagctgt cgtttgggat atcctggacg aagttatccg cgaacacccg | 1260 |
| gtactgctga accgtgcacc gactctgcac cgtctgggta tccaggcatt gaaccggta | 1320 |
| ctgatcgaag gtaaagctat ccagctgcac ccgctggttt gtgcggcata taacgccgac | 1380 |
| ttcgatggtg accagatggc tgttcacgta ccgctgacgc tggaagccca gctggaagcg | 1440 |
| cgtgcgctga tgatgtctac caacaacatc ctgtccccgg cgaacggcga accaatcatc | 1500 |
| gttccgtctc aggacgttgt actgggtctg tactacatga cccgtgactg tgttaacgcc | 1560 |
| aaaggcgaag catggtgct gactggcccg aaagaagcag aacgtctgta tcgctctggt | 1620 |
| ctggcttctc tgcatgcgcg cgttaaagtg cgtatcaccg agtatgaaaa agatgctaac | 1680 |
| ggtgaattag tagcgaaaac cagcctgaaa gacacgactg ttggccgtgc cattctgtgg | 1740 |
| atgattgtac cgaaaggtct gccttactcc atcgtcaacc aggcgctggg taaaaaagca | 1800 |
| atctccaaaa tgctgaacac ctgctaccgc attctcggtc tgaaaccgac cgttattttt | 1860 |
| gcggaccaga tcatgtacac cggcttcgcc tatgcagcgc gttctggtgc atctgttggt | 1920 |
| atcgatgaca tggtcatccc ggagaagaaa cacgaaatca tctccgaggc agaagcagaa | 1980 |
| gttgctgaaa ttcaggagca gttccagtct ggtctggtaa ctgcgggcga acgctacaac | 2040 |
| aaagttatcg atatctgggc tgcggcgaac gatcgtgtat ccaaagcgat gatggataac | 2100 |
| ctgcaaactg aaaccgtgat taaccgtgac ggtcaggaag agaagcaggt ttccttcaac | 2160 |
| agcatctaca tgatggccga ctccggtgcg cgtggttctg cggcacagat tcgtcagctt | 2220 |
| gctggtatgc gtggtctgat ggcgaagccg gatggctcca tcatcgaaac gccaatcacc | 2280 |
| gcgaacttcc gtgaaggtct gaacgtactc cagtacttca tctccaccca cggtgctcgt | 2340 |
| aaaggtctgg cggataccgc actgaaaact gcgaactccg ttacctgac tcgtcgtctg | 2400 |
| gttgacgtgg cgcaggacct ggtggttacc gaagacgatt gtggtaccca tgaaggtatc | 2460 |

```
atgatgactc cggttatcga gggtggtgac gttaaagagc cgctgcgcga tcgcgtactg    2520
ggtcgtgtaa ctgctgaaga cgttctgaag ccgggtactg ctgatatcct cgttccgcgc    2580
aacacgctgc tgcacgaaca gtggtgtgac ctgctggaag agaactctgt cgacgcggtt    2640
aaagtacgtt ctgttgtatc ttgtgacacc gactttggtg tatgtgcgca ctgctacggt    2700
cgtgacctgg cgcgtggcca catcatcaac aagggtgaag caatcggtgt tatcgcggca    2760
cagtccatcg gtgaaccggg tacacagctg accatgcgta cgttccacat cggtggtgcg    2820
gcatctcgtg cggctgctga atccagcatc caagtgaaaa acaaaggtag catcaagctc    2880
agcaacgtga gtcggttgt gaactccagc ggtaaactgg ttatcacttc ccgtaatact    2940
gaactgaaac tgatcgacga attcggtcgt actaaagaaa gctacaaagt accttacggt    3000
gcggtactgg cgaaaggcga tggcgaacag gttgctggcg cgaaaccgt tgcaaactgg    3060 gacccgcaca ccatgccggt tatcaccgaa gtaagcggtt ttgtacgctt tactgacatg    3120
atcgacggcc agaccattac gcgtcagacc gacgaactga ccggtctgtc ttcgctggtg    3180
gttctggatt ccgcagaacg taccgcaggt ggtaaagatc tgcgtccggc actgaaaatc    3240
gttgatgctc agggtaacga cgttctgatc ccaggtaccg atatgccagc gcagtacttc    3300
ctgccgggta aagcgattgt tcagctggaa gatggcgtac agatcagctc tggtgacacc    3360
ctggcgcgta ttccgcagga atccggcggt accaaggaca tcaccggtgg tctgccgcgc    3420
gttgcggacc tgttcgaagc acgtcgtccg aaagagccgg caatcctggc tgaaatcagc    3480
ggtatcgttt ccttcggtaa agaaaccaaa ggtaaacgtc gtctggttat caccccggta    3540
gacggtagcg atccgtacga agagatgatt ccgaaatggc gtcagctcaa cgtgttcgaa    3600
ggtgaacgtg tagaacgtgg tgacgtaatt tccgacggtc cggaagcgcc gcacgacatt    3660
ctgcgtctgc gtggtgttca tgctgttact cgttacatcg ttaacgaagt acaggacgta    3720
taccgtctgc agggcgttaa gattaacgat aaacacatcg aagttatcgt tcgtcagatg    3780
ctgcgtaaag ctaccatcgt taacgcgggt agctccgact tcctggaagg cgaacaggtt    3840
gaatactctc gcgtcaagat cgcaaaccgc gaactggaag cgaacggcaa agtgggtgca    3900
acttactccc gcgatctgct gggtatcacc aaagcgtctc tggcaaccga gtccttcatc    3960
tccgcggcat cgttccagga gaccactcgc gtgctgaccg aagcagccgt tgcgggcaaa    4020
cgcgacgaac tgcgcggcct gaaagagaac gttatcgtgg gtcgtctgat cccggcaggt    4080
accggttacg cgtacc                                                    4096

<210> SEQ ID NO 70
<211> LENGTH: 128
<212> TYPE: DNA
<213> ORGANISM: E. coli

<400> SEQUENCE: 70
accaggatcg tatgcgtcgc cgtgctgcgg gtgaagctcc ggctgcaccg caggtgactg     60
cagaagacgc atctgccagc ctggcagaac tgctgaacgc aggtctgggc ggttctgata    120
acgagtaa                                                             128

<210> SEQ ID NO 71
<211> LENGTH: 1185
<212> TYPE: DNA
<213> ORGANISM: E. coli

<400> SEQUENCE: 71
atgtctaaag aaaagtttga acgtacaaaa ccgcacgtta acgtcggtac tatcggccac    60
```

```
gttgaccatg gtaaaacaac gctgaccgct gcaatcacta ccgtactggc taaaacctac      120
ggcggtgctg ctcgcgcatt cgaccagatc gataacgcgc cggaagaaaa agctcgtggt      180
atcaccatca acacttctca cgttgaatac gacaccccga cccgtcacta cgcacacgta      240
gactgcccgg ggcacgccga ctatgttaaa aacatgatca ccggtgctgc gcagatggac      300
ggcgcgatcc tggtagttgc tgcgactgac ggcccgatgc cgcagactcg tgagcacatc      360
ctgctgggtc gtcaggtagg cgttccgtac atcatcgtgt cctgaacaa atgcgacatg      420 gttgatgacg aagagctgct ggaactggtt gaaatggaag ttcgtgaact tctgtctcag      480
tacgacttcc cggcgacga cactccgatc gttcgtggtt ctgctctgaa agcgctggaa      540
ggcgacgcag agtgggaagc gaaaatcctg gaactggctg gcttcctgga ttcttacatt      600
ccggaaccag agcgtgcgat tgacaagccg ttcctgctgc cgatcgaaga cgtattctcc      660
atctccggtc gtggtaccgt tgttaccggt cgtgtagaac gcggtatcat caaagttggt      720
gaagaagttg aaatcgttgg tatcaaagag actcagaagt ctacctgtac tggcgttgaa      780
atgttccgca aactgctgga cgaaggccgt gctggtgaga cgtaggtgt tctgctgcgt      840 ggtatcaaac gtgaagaaat cgaacgtggt caggtactgg ctaagccggg caccatcaag      900
ccgcacacca agttcgaatc tgaagtgtac attctgtcca agatgaagg cggccgtcat      960 actccgttct tcaaaggcta ccgtccgcag ttctacttcc gtactactga cgtgactggt      1020
accatcgaac tgccggaagg cgtagagatg gtaatgccgg gcgacaacat caaaatggtt      1080
gttaccctga tccacccgat cgcgatggac gacggtctgc gtttcgcaat ccgtgaaggc      1140
ggccgtaccg ttggcgcggg cgttgtagca aaagttctga gctaa                     1185

<210> SEQ ID NO 72
<211> LENGTH: 822
<212> TYPE: DNA
<213> ORGANISM: E. coli

<400> SEQUENCE: 72
atggcagttg ttaaatgtaa accgacatct ccgggtcgtc gccacgtagt taaagtggtt       60
aaccctgagc tgcacaaggg caaacctttt gctccgttgc tggaaaaaaa cagcaaatcc      120
ggtggtcgta acaacaatgg ccgtatcacc actcgtcata tcggtggtgg ccacaagcag      180
gcttaccgta ttgttgactt caacgcaac aaagacggta tcccggcagt tgttgaacgt      240
cttgagtacg atccgaaccg ttccgcgaac atcgcgctgg ttctgtacaa agacggtgaa      300
cgccgttaca tcctggcccc taaaggcctg aaagctggcg accagattca gtctggcgtt      360
gatgctgcaa tcaaaccagg taacaccctg ccgatgcgca acatcccggt tggttctact      420
gttcataacg tagaaatgaa accaggtaaa ggcggtcagc tggcacgttc cgctggtact      480
tacgttcaga tcgttgctcg tgatggtgct tatgtcaccc tgcgtctgcg ttctggtgaa      540
atgcgtaaag tagaagcaga ctgccgtgca actctgggcg aagttggcaa tgctgagcat      600 atgcgtgcgcg ttctgggtaa agcaggtgct gcacgctggc gtggtgttcg tccgaccgtt      660
cgcggtaccg cgatgaaccc ggtagaccac ccacatggtg gtggtgaagg tcgtaacttt      720
ggtaagcacc cggtaactcc gtggggcgtt cagaccaaag gtaagaagac ccgcagcaac      780
aagcgtactg ataaattcat cgtacgtcgc cgtagcaaat aa                         822

<210> SEQ ID NO 73
<211> LENGTH: 2856
<212> TYPE: DNA
```

<213> ORGANISM: E. coli

<400> SEQUENCE: 73

```
atggaaaaga catataaccc acaagatatc gaacagccgc tttacgagca ctgggaaaag      60
cagggctact ttaagcctaa tggcgatgaa agccaggaaa gtttctgcat catgatcccg     120
ccgccgaacg tcaccggcag tttgcatatg ggtcacgcct ccagcaaac catcatggat      180
accatgatcc gctatcagcg catgcagggc aaaaacaccc tgtggcaggt cggtactgac     240
cacgccggga tcgctaccca gatggtcgtt gagcgcaaga ttgccgcaga agaaggtaaa     300
acccgtcacg actacggccg cgaagctttc atcgacaaaa tctgggaatg aaagcggaa      360
tctggcggca ccattacccg tcagatgcgc cgtctcggca actccgtcga ctgggagcgt     420
gaacgcttca ccatggacga aggcctgtcc aatgcggtga agaagttttt cgttcgtctg     480
tataagaag acctgattta ccgtggcaaa cgcctggtaa actgggatcc gaaactgcgc      540
accgctatct ctgacctgga gtcgaaaac cgcgaatcga aggttcgat gtggcacatc       600
cgctatccgc tggctgacgg tgcgaaaacc gcagacggta agattatct ggtggtcgcg      660
actacccgtc cagaaaccct gctgggcgat actggcgtag ccgttaaccc ggaagatccg     720
cgttacaaag atctgattgg caaatatgtc attctgccgc tggttaaccg tcgtattccg     780
atcgttggcg acgaacacgc cgacatggaa aaaggcaccg gctgcgtgaa aatcactccg     840
gcgcacgact taacgacta tgaagtgggt aaacgtcacg ccctgccgat gatcaacatc      900
ctgacctttg acggcgatat ccgtgaaagc gcccaggtgt cgataccaa aggtaacgaa      960
tctgacgttt attccagcga aatccctgca gagttccaga actggagcg ttttgctgca     1020
cgtaaagcag tcgttgccgc agttgacgcg cttggcctgc tggaagaaat taaaccgcac    1080
gacctgaccg ttccttacgg cgaccgtggc ggcgtagtta tcgaaccaat gctgaccgac    1140
cagtggtacg tgcgtgccga tgtcctggcg aaaccggcgg ttgaagcggt tgagaacggc    1200
gacattcagt tcgtaccgaa gcagtacgaa aacatgtact ctcctggat gcgcgatatt    1260
caggactggt gtatctctcg tcagttgtgg tggggtcacc gtatcccggc atggtatgac    1320
gaagcgggta acgtttatgt tggccgcaac gaagacgaag tgcgtaaaga aaataacctc    1380
ggtgctgatg ttgtcctgcg tcaggacgaa gacgttctcg atacctggtt ctcttctgcg    1440
ctgtggacct tctctaccct tggctggccg gaaaataccg acgccctgcg tcagttccac    1500
ccaaccagcg tgatggtatc tggtttcgac atcattttct tctggattgc ccgcatgatc    1560
atgatgacca tgcacttcat caaagatgaa aatggcaaac cgcaggtgcc gttccacacc    1620
gtttacatga ccggcctgat tcgtgatgac gaaggccaga gatgtccaa atccaagggt     1680
aacgttatcg acccactgga tatggttgac ggtatttcgc tgccagaact gctggaaaaa    1740
cgtaccggca atatgatgca ccgcagctg gcggacaaaa tccgtaagcg caccgagaag    1800
cagttcccga acggtattga gccgcacggt actgacgcgc tgcgcttcac cctggcggcg    1860
ctggcgtcta ccggtcgtga catcaactgg gatatgaagc gtctggaagg ttaccgtaac    1920
ttctgtaaca gctgtggaa cgccagccgc tttgtgctga tgaacacaga aggtcaggat    1980
tgcggcttca acgcggcga aatgacgctg tcgctggcgg accgctggat tctgcggag    2040
ttcaaccaga ccatcaaagc gtaccgcgaa gcgctggaca gcttccgctt cgatatcgcc    2100
gcaggcattc tgtatgagtt cacctggaac cagttctgtg actggtatct cgagctgacc    2160
aagccggtaa tgaacggtgg caccgaagca gaactgcgcg gtactcgcca tacgctggtg    2220
actgtactgg aaggtctgct gcgcctcgcg catccgatca ttccgttcat caccgaaacc    2280
```

```
atctggcagc gtgtgaaagt actttgcggt atcactgccg acaccatcat gctgcagccg      2340
ttcccgcagt acgatgcatc tcaggttgat gaagccgcac tggccgacac cgaatggctg      2400
aaacaggcga tcgttgcggt acgtaacatc cgtgcagaaa tgaacatcgc gccgggcaaa      2460
ccgctggagc tgctgctgcg tggttgcagc gcggatgcag aacgtcgcgt aaatgaaaac      2520
cgtggcttcc tgcaaaccct ggcgcgtctg gaaagtatca ccgtgctgcc tgccgatgac      2580
aaaggtccgg tttccgttac gaagatcatc gacggtgcag agctgctgat cccgatggct      2640
ggcctcatca acaaagaaga tgagctggcg cgtctggcga agaagtggc gaagattgaa       2700 ggtgaaatca gccgtatcga gaacaaactg gcgaacgaag ctttgtcgc ccgcgcaccg       2760 gaagcggtca tcgcgaaaga gcgtgagaag ctggaaggct atgcggaagc gaaagcgaaa      2820
ctgattgaac agcaggctgt tatcgccgcg ctgtaa                                2856

<210> SEQ ID NO 74
<211> LENGTH: 447
<212> TYPE: DNA
<213> ORGANISM: B. anthracis

<400> SEQUENCE: 74
atgtttggat cagatttata tattgcatta gtattaggag ttacactgag ccttattttt       60
acagaaagaa caggtatttt acctgcaggt ttagttgtac ctggttatt agcactcgtt       120 tttaatcagc ccgtatttat gttggttgtt ttatttatca gtattttaac atatgtaatc     180
gttacgtatg gtgtttcaag attcatgatt ttatatggcc gtagaaaatt tgcggcaacg      240
ctaattacag gtatttgttt aaaacttta tttgattatt gttatcctgt tatgccattt      300 gagattttg aattccgtgg tattggagtt attgttccag gattaattgc aaatacaatt       360
caaagacaag ggttaccatt aacaattgga actacaattt tgttaagtgg tgcaacattt      420
gcaatcatga atatttatta cttatttt                                         447

<210> SEQ ID NO 75
<211> LENGTH: 2339
<212> TYPE: DNA
<213> ORGANISM: B. anthracis

<400> SEQUENCE: 75
atgactagaa ataaatttat acctaataag tttagtatta tatccttttc agtattacta       60
tttgctatat cctcctcaca ggctatagaa gtaaatgcta tgaatgaaca ttacactgag      120
agtgatatta aagaaaacca taaaactgaa aaaaataaaa ctgaaaaaga aaatttaaa       180 gacagtatta taacttagt taaaacagaa tttaccaatg aaactttaga taaaatacag       240
cagacacaag acttattaaa aaagatacct aaggatgtac ttgaaattta tagtgaatta      300
ggaggagaaa tctatttac agatatagat ttagtagaac ataaggagtt acaagattta       360
agtgaagaag agaaaaatag tatgaatagt agaggtgaaa aagttccgtt tgcatcccgt      420
tttgtatttg aaaagaaaag ggaaacacct aaattaatta taaatatcaa agattatgca      480
attaatagtg aacaaagtaa agaagtatat tatgaaattg gaaggggat ttctcttgat       540 attataagta aggataaatc tctagatcca gagttttaa atttaattaa gagtttaagc       600
gatgatagtg atagtagcga cctttattt agtcaaaaat ttaaagagaa gctagaattg      660
aataataaaa gtatagatat aaattttata aagaaaatt taactgaatt tcagcatgcg       720
ttttctttag cgttttctta ttattttgca cctgaccata gaacggtatt agagttatat      780
```

| | |
|---|---|
| gcccccgaca tgtttgagta tatgaataag ttagaaaaag ggggatttga gaaataagt | 840 |
| gaaagtttga agaaagaagg tgtggaaaaa gataggattg atgtgctgaa aggagaaaaa | 900 |
| gcacttaaag cttcaggttt agtaccagaa catgcagatg cttttaaaaa aattgctaga | 960 |
| gaattaaata catatattct ttttaggcct gttaataagt tagctacaaa ccttattaaa | 1020 |
| agtggtgtgg ctacaaaggg attgaatgtt catggaaaga gttcggattg gggccctgta | 1080 |
| gctggataca taccatttga tcaagattta tctaagaagc atggtcaaca attagctgtc | 1140 |
| gagaaaggaa atttagaaaa taaaaaatca attacagagc atgaaggtga aataggtaaa | 1200 |
| ataccattaa agttagacca tttaagaata gaagagttaa aggaaaatgg gataattttg | 1260 |
| aagggtaaaa aagaaattga taatggtaaa aaatattatt tgttagaatc gaataatcag | 1320 |
| gtatatgaat ttagaattag cgatgaaaac aacgaagtac aatacaagac aaaagaaggt | 1380 |
| aaaattactg ttttagggga aaaattcaat tggagaaata tagaagtgat ggctaaaaat | 1440 |
| gtagaagggg tcttgaagcc gttaacagct gactatgatt tatttgcact tgccccaagt | 1500 |
| ttaacagaaa taaaaaaaca ataccacaa aaagaatggg ataaagtagt taacacccca | 1560 |
| aattcattag aaaagcaaaa aggtgttact aatttattga ttaaatatgg aattgagagg | 1620 |
| aaaccggatt caactaaggg aacttttatca aattggcaaa acaaatgct tgatcgtttg | 1680 |
| aatgaagcag tcaaatatac aggatataca gggggggatg tggttaacca tggcacagag | 1740 |
| caagataatg aagagtttcc tgaaaaagat aacgaaattt ttataattaa tccagaaggt | 1800 |
| gaatttatat taactaaaaa ttgggagatg acaggtagat ttatagaaaa aaacattacg | 1860 |
| ggaaaagatt atttatatta ttttaaccgt tcttataata aaatagctcc tggtaataaa | 1920 |
| gcttatattg agtggactga tccgattaca aaagccaaaa taaataccat ccctacgtca | 1980 |
| gcagagttta taaaaaactt atccagtatc agaagatctt caaatgtagg agtttataaa | 2040 |
| gatagtggcg acaaagacga atttgcaaaa aagaaagcg tgaaaaaaat tgcaggatat | 2100 |
| ttgtcagact attacaattc agcaaatcat atttttctc aggaaaaaaa gcgtaaaata | 2160 |
| tcaatatttc gtggaatcca agcctataat gaaattgaaa atgttctaaa atctaaacaa | 2220 |
| atagcaccag aatacaaaaa ttattttcaa tatttaaagg aaaggattac caatcaagtt | 2280 |
| caattgcttc taacacatca aaaatctaat attgaattta aattattgta taaacaatt | 2339 |

<210> SEQ ID NO 76
<211> LENGTH: 2480
<212> TYPE: DNA
<213> ORGANISM: B. anthracis

<400> SEQUENCE: 76

| | |
|---|---|
| atgaatataa aaaagaatt tataaaagta attagtatgt catgtttagt aacagcaatt | 60 |
| actttgagtg gtcccgtctt tatccccctt gtacaggggg cgggcggtca tggtgatgta | 120 |
| ggtatgcacg taaagagaa agagaaaaat aaagatgaga ataagagaaa agatgaagaa | 180 |
| cgaaataaaa cacaggaaga gcatttaaag gaaatcatga acacattgt aaaaatagaa | 240 |
| gtaaaagggg aggaagctgt taaaaaagag gcagcagaaa agctacttga gaaagtacca | 300 |
| tctgatgttt tagagatgta taagcaatt ggaggaaaga tatatattgt ggatggtgat | 360 |
| attacaaaac atatatcttt agaagcatta tctgaagata gaaaaaaaat aaaagacatt | 420 |
| tatgggaaag atgctttatt acatgaacat tatgtatatg caaagaagg atatgaaccc | 480 |
| gtacttgtaa tccaatcttc ggaagattat gtagaaaata ctgaaaaggc actgaacgtt | 540 |
| tattatgaaa taggtaagat attatcaagg gatatttaa gtaaaattaa tcaaccatat | 600 |

```
cagaaatttt tagatgtatt aaataccatt aaaaatgcat ctgattcaga tggacaagat      660
cttttattta ctaatcagct taaggaacat cccacagact tttctgtaga attcttggaa      720
caaaatagca atgaggtaca agaagtatttt gcgaaagctt ttgcatatta tatcgagcca     780
cagcatcgtg atgttttaca gctttatgca ccggaagctt ttaattacat ggataaattt      840
aacgaacaag aaataaatct atccttggaa gaacttaaag atcaacggat gctgtcaaga      900
tatgaaaaat gggaaaagat aaaacagcac tatcaacact ggagcgattc tttatctgaa      960
gaaggaagag gacttttaaa aaagctgcag attcctattg agccaaagaa agatgacata     1020
attcattctt tatctcaaga agaaaaagag cttctaaaaa gaatacaaat tgatagtagt     1080 gatttttat ctactgagga aaagagtttt ttaaaaaagc tacaaattga tattcgtgat     1140
tctttatctg aagaagaaaa agagcttta aatagaatac aggtggatag tagtaatcct     1200
ttatctgaaa aagaaaaga gttttaaaa aagctgaaac ttgatattca accatatgat     1260
attaatcaaa ggttgcaaga tacaggaggg ttaattgata gtccgtcaat taatcttgat     1320
gtaagaaagc agtataaaag ggatattcaa aatattgatg ctttattaca tcaatccatt     1380
ggaagtacct tgtacaataa aatttatttg tatgaaaata tgaatatcaa taaccttaca     1440
gcaaccctag gtgcggattt agttgattcc actgataata ctaaaattaa tagaggtatt     1500
ttcaatgaat tcaaaaaaaa tttcaaatat agtatttcta gtaactatat gattgttgat     1560
ataaatgaaa ggcctgcatt agataatgag cgtttgaaat ggagaatcca attatcacca     1620
gatactcgag caggatattt agaaaatgga aagcttatat acaaagaaa catcggtctg     1680 gaaataaagg atgtacaaat aattaagcaa tccgaaaaag aatatataag gattgatgcg     1740
aaagtagtgc caaagagtaa aatagataca aaaattcaag aagcacagtt aaatataaat     1800
caggaatgga ataaagcatt agggttacca aaatatacaa agcttattac attcaacgtg     1860
cataatagat atgcatccaa tattgtagaa agtgcttatt taatattgaa tgaatggaaa     1920
aataatattc aaagtgatct tataaaaaag gtaacaaatt acttagttga tggtaatgga     1980
agatttgttt ttaccgatat tactctccct aatatagctg aacaatatac acatcaagat     2040
gagatatatg agcaagttca ttcaaaaggg ttatatgttc cagaatcccg ttctatatta     2100
ctccatggac cttcaaaagg tgtagaatta aggaatgata gtgagggttt tatacacgaa     2160
tttggacatg ctgtggatga ttatgctgga tatctattag ataagaacca atctgattta     2220
gttacaaatt ctaaaaaatt cattgatatt tttaaggaag aagggagtaa tttaacttcg     2280
tatgggagaa caaatgaagc ggaattttt gcagaagcct ttaggttaat gcattctacg     2340
gaccatgctg aacgtttaaa agttcaaaaa aatgctccga aaactttcca atttattaac     2400
gatcagatta agttcattat taactcataa gtaatgtatt aaaaattttc aaatggattt     2460
aataataata ataataataa                                                 2480
```

<210> SEQ ID NO 77
<211> LENGTH: 288
<212> TYPE: DNA
<213> ORGANISM: B. anthracis

<400> SEQUENCE: 77

-continued

```
atgagtaaaa aacaacaagg ttataacaag gcaacttctg gtgctagcat tcaaagcaca      60
aatgctagtt atggtacaga gtttgcgact gaaacaaatg tacaagcagt aaaacaagca     120
aacgcacaat cagaagctaa gaaagcgcaa gcttctggtg ctagcattca aagcacaaat     180
gctagttatg gtacagaatt tgcaactgaa acagacgtgc atgctgtgaa aaaacaaaat     240
gcacaatcag ctgcaaaaca atcacaatct tctagttcaa atcagtaa                 288
```

METHODS FOR CONCURRENT IDENTIFICATION AND QUANTIFICATION OF AN UNKNOWN BIOAGENT

CROSS-REFERENCE TO RELATED APPLICATIONS

This application is a continuation of U.S. Non-Provisional application Ser. No. 13/447,678 filed Apr. 16, 2012, which is a continuation of U.S. Non-Provisional application Ser. No. 12/684,742 filed Jan. 8, 2010, which claims the benefit of priority to U.S. Non-Provisional application Ser. No. 11/059,776 filed Feb. 17, 2005, now U.S. Pat. No. 7,666,592 issued Feb. 23, 2010, which claims the benefit of U.S. Provisional Application Ser. No. 60/545,425 filed Feb. 18, 2004, and U.S. Provisional Application Ser. No. 60/559,754 filed Apr. 5, 2004, each of which is incorporated herein by reference in its entirety.

STATEMENT OF GOVERNMENT SUPPORT

This invention was made with United States Government support under contract MDA972-00-C-0053 awarded by DARPA/SAIC. The United States Government has certain rights in the invention.

FIELD OF THE INVENTION

The present invention is related generally to nucleic acid amplification technology and microbiology.

BACKGROUND OF THE INVENTION

Information about the identity and total amount of microbes in biological samples is of prime importance in medicine in order to assess the risk of infectious disease, to diagnose infections and predict their clinical course. In a variety of other areas such as food product monitoring, bioremediation, microbial forensics and biowarfare/bioterror investigations, efficient and cost effective methods for quantification of microbial bioagents are needed. In addition, determination of the quantity of a bioagent (microbe, bacterium, virus, fungus, etc.) is a common endeavor in microbiology in the fields of clinical diagnostics, epidemiology, forensics, bioremediation, and quality control.

Methods currently in use for detection and determination of bacteria include bacterial culture and microscopy, detection of bacterial metabolites, and identification of surface molecules by specific antibodies.

The polymerase chain reaction (PCR) is only a qualitative method due to its exponential time course and equally exponential amplification of errors. Efforts have been made to convert PCR to a quantitative method. Among the variety of quantitative PCR methods, are methods depending upon external standardization and on internal standardization. Among the latter, competitive PCR methods are based on co-amplification of a target DNA with a standard competitor DNA which competes with the template DNA for the same set of amplification primers. Since the competitor is added to the PCR reaction mixture in known amounts, it is possible to calculate the amount of target DNA from the experimental determination of the ratio of amplified products of sample and standard competitor DNA.

Methods for rapid and cost effective identification of microbial bioagents through molecular mass measurement of amplification products by molecular mass analysis of bioagent identifying amplicons are disclosed and claimed in U.S. application Ser. Nos. 09/798,007, 09/891,793, 10/660,997, 10/660,122, 10/660,996, 10/418,514 and 10/728,486, each of which is commonly owned and incorporated herein by reference in its entirety. These methods and others would derive great benefit from a means of determination of the quantity of any given microbial bioagent present in a biological sample. Quantification of organisms can be very valuable, particularly in a clinical setting, like Hepatitis C for example, where the greater the number of infectious organisms generally correlates with a less healthy patient and a more difficult clinical course.

The methods described herein satisfy the need for methods for concurrent identification and quantification of bioagents, as well as other needs, by providing internal calibration using a nucleic acid standard calibrant in an amplification reaction.

SUMMARY OF THE INVENTION

The present invention provides methods for determination of the quantity of an unknown bioagent in a sample by contacting the sample with a pair of primers and a known quantity of a calibration polynucleotide that comprises a calibration sequence. Nucleic acid from the bioagent in the sample is concurrently amplified with the pair of primers and amplifying nucleic acid from the calibration polynucleotide in the sample with the pair of primers to obtain a first amplification product comprising a bioagent identifying amplicon and a second amplification product comprising a calibration amplicon. The sample is then subjected to molecular mass analysis resulting in molecular mass and abundance data for the bioagent identifying amplicon and the calibration amplicon. The bioagent identifying amplicon is distinguished from the calibration amplicon based on molecular mass wherein the molecular mass of the bioagent identifying amplicon provides a means for identifying the bioagent. Comparison of bioagent identifying amplicon abundance data and calibration amplicon abundance data indicates the quantity of bioagent in the sample.

BRIEF DESCRIPTION OF THE DRAWINGS

Figure 2:
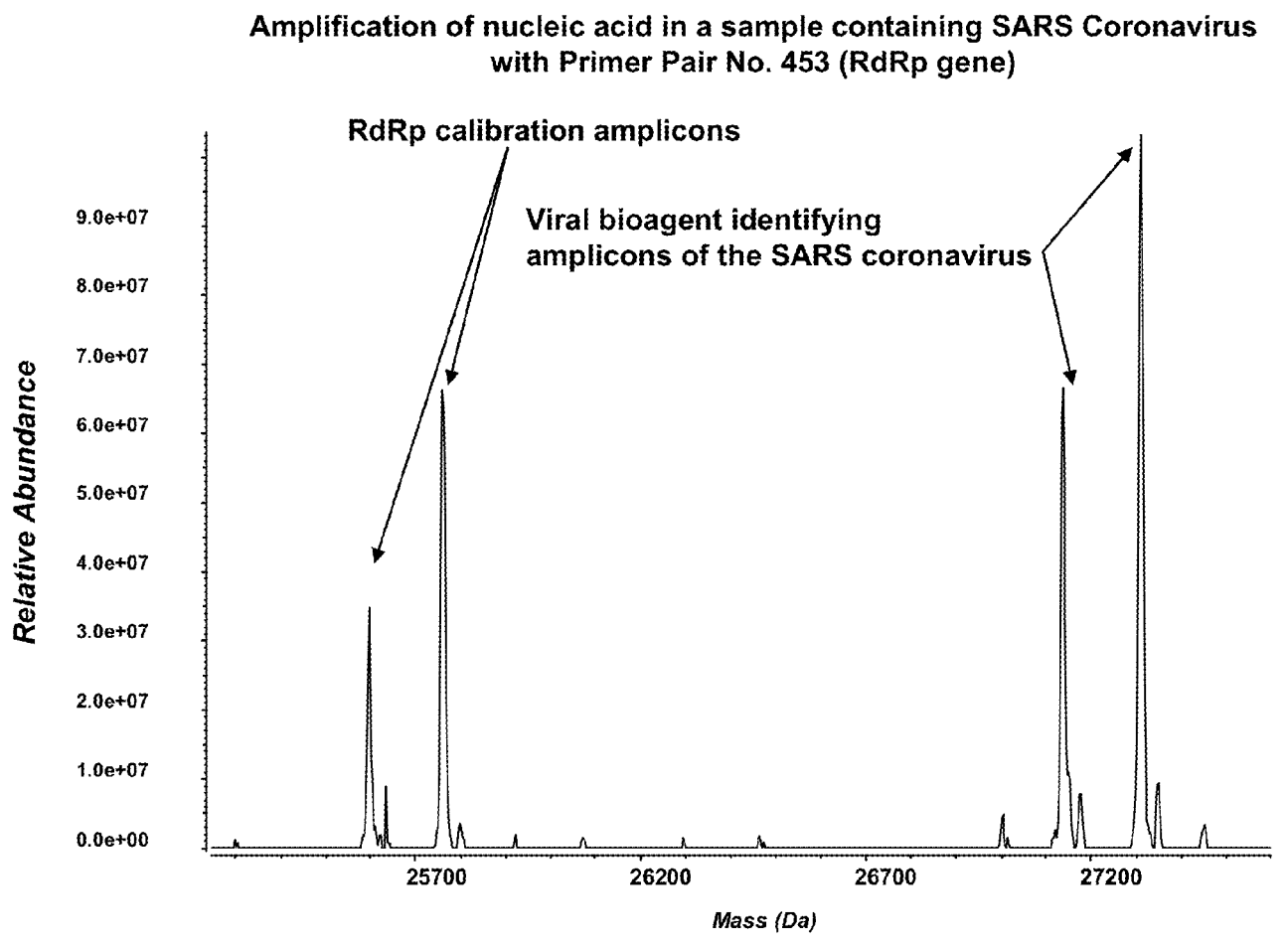

FIG. 2 shows a representative mass spectrum of a viral bioagent identifying amplicon for the RdRp primer set of the SARS coronavirus (SARS) and the corresponding RdRp calibration amplicon.

Figure 1:
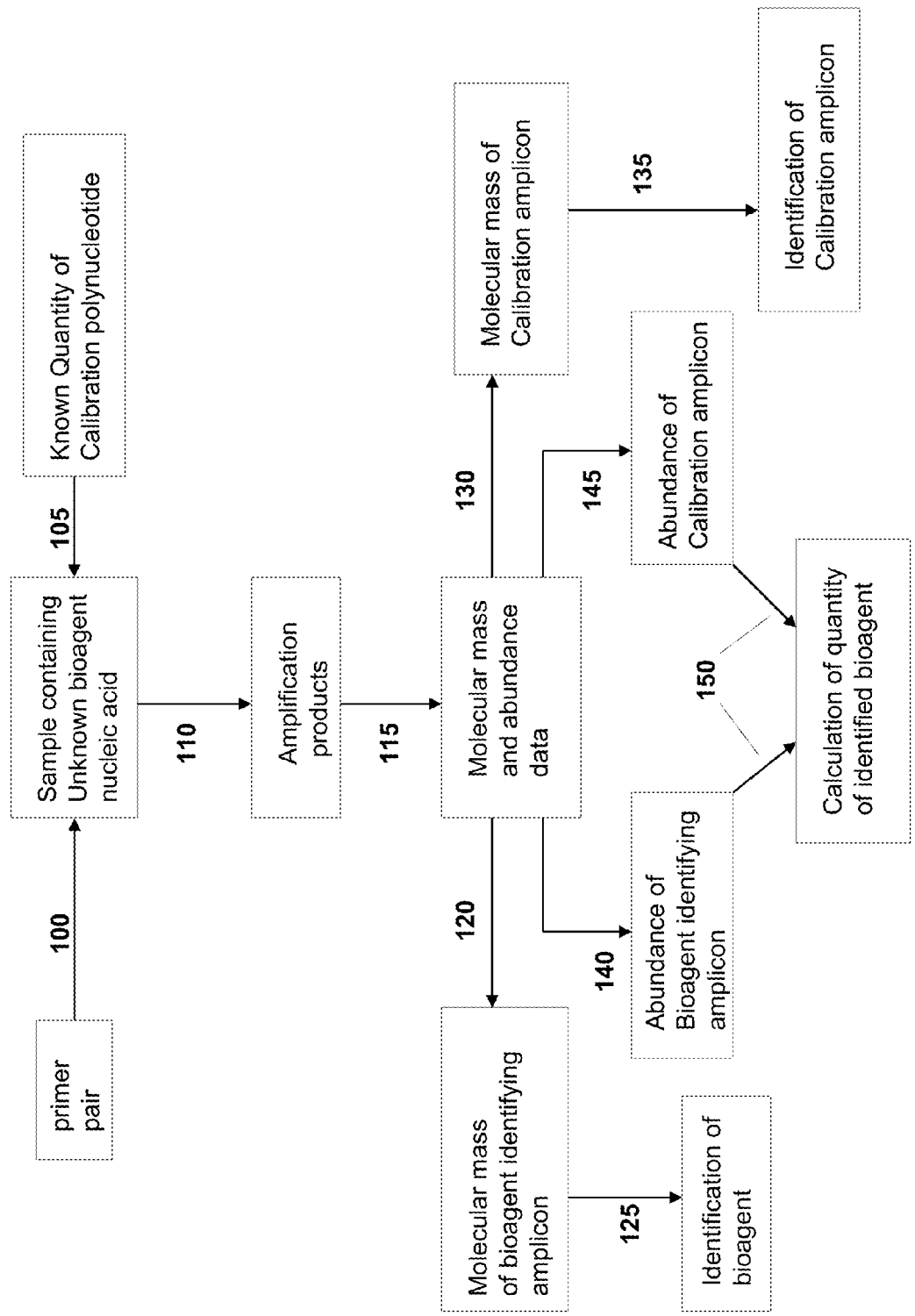
FIG. 1 shows a representative process diagram for identification and determination of the quantity of a bioagent in a sample.

In one embodiment, a sample comprising an unknown bioagent is contacted with a pair of primers which can amplify nucleic acid from the bioagent, and a known quantity of a polynucleotide that comprises a calibration sequence. The nucleic acids of the bioagent and of the calibration sequence are amplified. The rate of amplification is reasonably assumed to be similar for the nucleic acid of the bioagent and of the calibration sequence. The amplification reaction produces two amplification products: a bioagent identifying amplicon and a calibration amplicon. The amplified sample containing the bioagent identifying amplicon and the calibration amplicon is then subjected to molecular mass analysis by mass spectrometry, for example. The resulting molecular mass analysis of the nucleic acid of the bioagent and of the calibration sequence provides molecular mass data and abundance data for the nucleic acid of the bioagent and of the calibration sequence. The molecular mass data obtained for the nucleic acid of the bioagent enables identification of the unknown bioagent and the abundance data enables calculation of the quantity of the bioagent, based on the knowledge of the quantity of calibration polynucleotide contacted with the sample. The calculations are well within the scope of those of the ordinary artisan.

A calibration sequence is a sequence chosen to represent a portion of a genome of a bioagent (bacterium, virus etc.) that can be amplified by a particular primer pair to yield an amplification product (calibration amplicon) that can be distinguished on the basis of its molecular mass from an analogous amplification product (bioagent identifying amplicon) obtained by amplification of native DNA of a bioagent (bacterium, virus, etc) with the same pair of primers. One means of distinguishing an amplification product of a calibration sequence vs. a bioagent identifying amplicon is to design the calibration sequence so that, upon amplification, it gives rise to an amplification product consisting of a calibration amplicon that has a molecular mass distinguishable from the analogous bioagent identifying amplicon. This is desired because, as in any internally calibrated method, the calibration sequence and the bioagent sequence are amplified concurrently in the same amplification reaction vessel.

In some embodiments, construction of a standard curve where the amount of calibration polynucleotide spiked into the sample is varied, provides additional resolution and improved confidence for the determination of the quantity of bioagent in the sample. The use of standard curves for analytical determination of molecular quantities is well known to one with ordinary skill and can be performed without undue experimentation.

In some embodiments, multiplex amplification is performed where multiple bioagent identifying amplicons are amplified with multiple intelligent primer pairs which also amplify the corresponding standard calibration sequences. In this or other embodiments, the standard calibration sequences are optionally included within a single vector such as a plasmid which functions as the calibration polynucleotide. Multiplex amplification methods are well known to those with ordinary skill and can be performed without undue experimentation.

In some embodiments, the calibrant polynucleotide is used as an internal positive control to confirm that amplification conditions and subsequent analysis steps are successful in producing a measurable amplicon. Even in the absence of copies of the genome of a bioagent, the calibration polynucleotide can give rise to a calibration amplicon. Failure to produce a measurable calibration amplicon indicates a failure of amplification or subsequent analysis step such as amplicon purification or molecular mass determination.

In some embodiments, the calibration sequence is inserted into a vector which then itself functions as the calibration polynucleotide. In some embodiments, more than one calibration sequence is inserted into the vector that functions as the calibration polynucleotide. The process of inserting polynucleotides into vectors is routine to those skilled in the art and can be accomplished without undue experimentation. Thus, it should be recognized that the present invention should not be limited to the embodiments described herein. The present invention can be applied for determination of the quantity of any bioagent identifying amplicon when an appropriate standard calibrant polynucleotide sequence is designed and used. The process of choosing an appropriate vector such as a plasmid for insertion of a calibrant is also a routine operation that can be accomplished by one with ordinary skill without undue experimentation.

In some embodiments of the present invention, determination of the molecular masses of the bioagent identifying amplicon and the calibration amplicon is accomplished using mass spectrometry. Exemplary techniques of mass spectrometry include, but are not limited to, electrospray ionization Fourier transform ion cyclotron resonance mass spectrometry (ESI-FTICR-MS) and electrospray ionization time-of-flight mass spectrometry (ESI-TOF-MS).

In some embodiments, bioagent identifying amplicons and calibration amplicons are of a length between about 45-200 base pairs. One will recognize that these embodiments comprise bioagent identifying amplicons and calibration amplicons of lengths of about 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 base pairs, or any range therewithin.

In other embodiments, bioagent identifying amplicons and calibration amplicons are of a length between about 45-140 base pairs. One will recognize that these embodiments comprise bioagent identifying amplicons and calibration amplicons of lengths of about 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, or 140 base pairs, or any range therewithin.

In some embodiments, the primers used to obtain bioagent identifying amplicons and calibration amplicons upon amplification hybridize to conserved regions of nucleic acid of genes encoding proteins or RNAs necessary for life which include, but are not limited to: 16S and 23S rRNAs, RNA polymerase subunits, t-RNA synthetases, elongation factors, ribosomal proteins, protein chain initiation factors, cell division proteins, chaperonin groEL, chaperonin dnaK, phosphoglycerate kinase, NADH dehydrogenase, DNA ligases, and DNA topoisomerases.

Calibration sequences can be routinely designed without undue experimentation by choosing a reference sequence representing any bioagent identifying amplicon that can be amplified by a specific pair of primers of any class e.g: broad range survey, division-wide, clade level, or drill down or any arbitrarily named class of primer and by deleting or inserting about 2-8 consecutive nucleobases into that sequence such that the calibration sequence is distinguishable by molecular mass from the reference sequence upon which the calibration sequence is based. One will recognize that this range comprises insertions or deletions of 2, 3, 4, 5, 6, 7, or 8 nucleobases. In other embodiments, the total insertion or deletion of consecutive nucleobases may also exceed 8 nucleobases. In other embodiments, the total insertion or deletion of consecutive nucleobases results in a calibration sequence having at least 80%, at least 85%, at least 90%, or at least 95% sequence identity with a chosen standard sequence of a bioagent identifying amplicon.

In some embodiments, the primers used for amplification of bioagent identifying amplicons and calibration amplicons hybridize to and amplify genomic DNA, DNA of bacterial plasmids or DNA of DNA viruses.

In some embodiments, the primers used for amplification of bioagent identifying amplicons and corresponding calibration amplicons hybridize directly to ribosomal RNA or messenger RNA (mRNA) and act as reverse transcription primers for obtaining DNA from direct amplification of bacterial rRNA. Methods of amplifying RNA using reverse transcriptase are well known to those with ordinary skill in the art and can be routinely established without undue experimentation.

Synthesis of primers is well known and routine in the art. The primers may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

The primers can be employed as compositions for use in methods for identification of bacterial bioagents as follows: a primer pair composition is contacted with nucleic acid of an unknown bacterial bioagent. The nucleic acid is then amplified by a nucleic acid amplification technique, such as PCR for example, to obtain an amplification product that represents a bioagent identifying amplicon. The molecular mass of a single strand or each strand of the double-stranded amplification product is determined by a molecular mass measurement technique such as mass spectrometry for example, wherein the two strands of the double-stranded amplification product are separated during the ionization process. In some embodiments, the mass spectrometry is electrospray Fourier transform ion cyclotron resonance mass spectrometry (ESI-FTICR-MS) or electrospray time of flight mass spectrometry (ESI-TOF-MS). A list of possible base compositions can be generated for the molecular mass value obtained for each strand and the choice of the correct base composition from the list is facilitated by matching the base composition of one strand with a complementary base composition of the other strand. The molecular mass or base composition thus determined is then compared with a database of molecular masses or base compositions of analogous bioagent identifying amplicons for known bioagents. A match between the molecular mass or base composition of the amplification product and the molecular mass or base composition of an analogous bioagent identifying amplicon for a known bioagent indicates the identity of the unknown bioagent. In some embodiments, the method is repeated using a different primer pair to resolve possible ambiguities in the identification process or to improve the confidence level for the identification assignment.

In some embodiments, a bioagent identifying amplicon or a calibration amplicon may be produced using only a single primer composition (either the forward or reverse primer of any given primer pair), provided an appropriate amplification method is chosen, such as, for example, low stringency single primer PCR (LSSP-PCR).

In some embodiments, the oligonucleotide primers are "broad range survey primers" which hybridize to conserved regions of nucleic acid encoding ribosomal RNA (rRNA) of at least 50%, at least 60%, at least 70%, at least 80%, at least 90%, at least 99%, or all known bacteria and produce bacterial bioagent identifying amplicons. As used herein, the term "broad range survey primers" refers to primers that bind to nucleic acid encoding rRNAs of at least 50%, at least 60%, at least 70%, at least 80%, at least 90%, at least 99%, or all known species of bacteria. In some embodiments, the rRNAs to which the primers hybridize are 16S and 23S rRNAs.

In some cases, the molecular mass or base composition of a bacterial bioagent identifying amplicon defined by a broad range survey primer pair does not provide enough resolution to unambiguously identify a bacterial bioagent at the species level. These cases benefit from further analysis of one or more bacterial bioagent identifying amplicons generated from at least one additional broad range survey primer pair or from at least one additional "division-wide" primer pair (vide infra). The employment of more than one bioagent identifying amplicon for identification of a bioagent is herein referred to as "triangulation identification" (vide infra).

In other embodiments, the oligonucleotide primers are "division-wide" primers which hybridize to nucleic acid encoding genes of broad divisions of bacteria such as members of the *Bacillus/Clostridia* group or members of the α-, β-, γ-, and ε-proteobacteria. In some embodiments, a division of bacteria comprises any grouping of bacterial genera with more than one genus represented. For example, the β-proteobacteria group comprises members of the following genera: *Eikenella, Neisseria, Achromobacter, Bordetella, Burkholderia,* and *Raltsonia*. Species members of these genera can be identified using bacterial bioagent identifying amplicons generated with a primer pair which produces a bacterial bioagent identifying amplicon from the tufB gene of β-proteobacteria. Examples of genes to which division-wide primers may hybridize to include, but are not limited to: RNA polymerase subunits such as rpoB and rpoC, tRNA synthetases such as valyl-tRNA synthetase (valS) and aspartyl-tRNA synthetase (aspS), elongation factors such as elongation factor EF-Tu (tufB), ribosomal proteins such as ribosomal protein L2 (rplB), protein chain initiation factors such as protein chain initiation factor infB, chaperonins such as groL and dnaK, and cell division proteins such as peptidase ftsH (hflB).

In other embodiments, the oligonucleotide primers are designed to enable the identification of bacteria at the clade group level, which is a monophyletic taxon referring to a group of organisms which includes the most recent common ancestor of at least 70%, at least 80%, at least 90%, or all of its members and at least 70%, at least 80%, at least 90%, or all of the descendants of that most recent common ancestor. The *Bacillus cereus* clade is an example of a bacterial clade group.

In other embodiments, the oligonucleotide primers are "drill-down" primers which enable the identification of "sub-species characteristics." These primers can hybridize to conserved regions of nucleic acid of genes encoding structural proteins or proteins implicated in, for example, pathogenicity. Examples of genes indicating sub-species characteristics include, but are not limited to: toxin genes, pathogenicity markers, antibiotic resistance genes and virulence factors. Drill down primers provide the functionality of producing bacterial bioagent identifying amplicons for drill-down analyses such as strain typing when contacted with bacterial nucleic acid under amplification conditions. Identification of such sub-species characteristics is often critical for determining proper clinical treatment of bacterial infections.

It is, thus, readily apparent that one with ordinary skill can design calibration sequences that can be amplified by any of the primer classes disclosed herein in order to produce appropriate calibration amplicons.

One with ordinary skill in the art of design of amplification primers will recognize that a given primer need not hybridize with 100% complementarity in order to effectively prime the synthesis of a complementary nucleic acid strand in an amplification reaction. Moreover, a primer may hybridize over one or more segments such that intervening or adjacent segments are not involved in the hybridization event. (e.g: a loop structure or a hairpin structure). The primers of the present invention may comprise at least 70%, at least 75%, at least 80%, at least 85%, at least 90%, at least 95% or at least 99% sequence identity with any of the primers listed in Table 1. Thus, in some embodiments of the present invention, an extent of variation of 70% to 100% of the sequence identity is possible relative to the specific primer sequences disclosed herein. Determination of sequence identity is described in the following example: a primer 20 nucleobases in length which is identical to another 20 nucleobase primer having two non-identical residues has 18 of 20 identical residues (18/20=0.9 or 90% sequence identity). In another example, a primer 15 nucleobases in length having all residues identical to a 15 nucleobase segment of primer 20 nucleobases in length would have 15/20=0.75 or 75% sequence identity with the 20 nucleobase primer.

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some embodiments, complementarity of primers with respect to the conserved priming regions of bacterial nucleic acid, is between about 70% and about 80%. In other embodiments, homology, sequence identity or complementarity, is between about 80% and about 90%. In yet other embodiments, homology, sequence identity or complementarity, is about 90%, about 92%, about 94%, about 95%, about 96%, about 97%, about 98%, about 99% or about 100%.

One with ordinary skill is able to calculate percent sequence identity or percent sequence homology and able to determine, without undue experimentation, the effects of variation of primer sequence identity on the function of the primer in its role in priming synthesis of a complementary strand of nucleic acid for production of an amplification product of a corresponding bioagent identifying amplicon.

In some embodiments of the present invention, the oligonucleotide primers are between 13 and 35 nucleobases in length (13 to 35 linked nucleotide residues). These embodiments comprise oligonucleotide primers 13, 14, 15, 16, 17, 18, 19, 20, 21, 22, 23, 24, 25, 26, 27, 28, 29, 30, 31, 32, 33, 34 or 35 nucleobases in length, or any range therewithin.

In some embodiments, any given primer comprises a modification comprising the addition of a non-templated T residue to the 5' end of the primer i.e: the added T residue does not necessarily hybridize to the nucleic acid being amplified. The addition of a non-templated T residue has the effect of minimizing the addition of non-templated A residues as a result of the non-specific enzyme activity of Taq polymerase (Magnuson et al., Biotechniques, 1996, 21, 700-709), an occurrence which may lead to ambiguous results arising from molecular mass analysis.

In some embodiments of the present invention, primers may contain one or more universal bases. Because any variation (due to codon wobble in the $3^{rd}$ position) in the conserved regions among species is likely to occur in the third position of a DNA triplet, oligonucleotide primers can be designed such that the nucleotide corresponding to this position is a base which can bind to more than one nucleotide, referred to herein as a "universal nucleobase." For example, under this "wobble" pairing, inosine (I) binds to U, C or A; guanine (G) binds to U or C, and uridine (U) binds to U or C. Other examples of universal nucleobases include nitroindoles such as 5-nitroindole or 3-nitropyrrole (Loakes et al., Nucleosides and Nucleotides, 1995, 14, 1001-1003), the degenerate nucleotides dP or dK (Hill et al.), an acyclic nucleoside analog containing 5-nitroindazole (Van Aerschot et al., Nucleosides and Nucleotides, 1995, 14, 1053-1056) or the purine analog 1-(2-deoxy-(3-D-ribofuranosyl)-imidazole-4-carboxamide (Sala et al., Nucl. Acids Res., 1996, 24, 3302-3306).

In some embodiments, to compensate for the somewhat weaker binding by the "wobble" base, the oligonucleotide primers are designed such that the first and second positions of each triplet are occupied by nucleotide analogs which bind with greater affinity than the unmodified nucleotide. Examples of these analogs include, but are not limited to, 2,6-diaminopurine which binds to thymine, 5-propynyluracil which binds to adenine and 5-propynylcytosine and phenoxazines, including G-clamp, which binds to G. Propynylated pyrimidines are described in U.S. Pat. Nos. 5,645,985, 5,830,653 and 5,484,908, each of which is commonly owned and incorporated herein by reference in its entirety. Propynylated primers are described in U.S. Ser. No. 10/294,203 which is also commonly owned and incorporated herein by reference in entirety. Phenoxazines are described in U.S. Pat. Nos. 5,502,177, 5,763,588, and 6,005,096, each of which is incorporated herein by reference in its entirety.

G-clamps are described in U.S. Pat. Nos. 6,007,992 and 6,028,183, each of which is incorporated herein by reference in its entirety.

In some embodiments, non-template primer tags are used to increase the melting temperature ($T_m$) of a primer-template duplex in order to improve amplification efficiency. A non-template tag is designed to hybridize to at least three consecutive A or T nucleotide residues on a primer which are complementary to the template. In any given non-template tag, A can be replaced by C or G and T can also be replaced by C or G. The extra hydrogen bond in a G-C pair relative to a A-T pair confers increased stability of the primer-template duplex and improves amplification efficiency.

In other embodiments, propynylated tags may be used in a manner similar to that of the non-template tag, wherein two or more 5-propynylcytidine or 5-propynyluridine residues replace template matching residues on a primer. In other embodiments, a primer contains a modified internucleoside linkage such as a phosphorothioate linkage, for example.

In some embodiments, the primers contain mass-modifying tags. Reducing the total number of possible base compositions of a nucleic acid of specific molecular weight provides a means of avoiding a persistent source of ambiguity in determination of base composition of amplification products. Addition of mass-modifying tags to certain nucleobases of a given primer will result in simplification of de novo determination of base composition of a given bioagent identifying amplicon (vide infra) from its molecular mass.

In some embodiments of the present invention, the mass modified nucleobase comprises one of the following: 7-deaza-2'-deoxyadenosine-5-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, O6-methyl-2'-deoxyguanosine-5'-triphosphate, N2-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises $^{15}N$ or $^{13}C$ or both $^{15}N$ and $^{13}C$.

In some embodiments, bioagent identifying amplicons amenable to molecular mass determination which are produced by the primers described herein are either of a length, size or mass compatible with the particular mode of molecular mass determination or compatible with a means of providing a predictable fragmentation pattern in order to obtain predictable fragments of a length compatible with the particular mode of molecular mass determination. Such means of providing a predictable fragmentation pattern of an amplification product include, but are not limited to, cleavage with restriction enzymes or cleavage primers, for example. Methods of using restriction enzymes and cleavage primers are well known to those with ordinary skill in the art.

In some embodiments, amplification products corresponding to bacterial bioagent identifying amplicons are obtained using the polymerase chain reaction (PCR) which is a routine method to those with ordinary skill in the molecular biology arts. Other amplification methods may be used such as ligase chain reaction (LCR), low-stringency single primer PCR, and multiple strand displacement amplification (MDA) which are also well known to those with ordinary skill.

In the context of this invention, a "bioagent" is any organism, cell, or virus, living or dead, or a nucleic acid derived from such an organism, cell or virus. Examples of bioagents include, but are not limited to, cells, (including but not limited to human clinical samples, bacterial cells and other pathogens), viruses, fungi, protists, parasites, and pathogenicity markers (including but not limited to: pathogenicity islands, antibiotic resistance genes, virulence factors, toxin genes and other bioregulating compounds). Samples may be alive or dead or in a vegetative state (for example, vegetative bacteria or spores) and may be encapsulated or bioengineered. In the context of this invention, a "pathogen" is a bioagent which causes a disease or disorder.

In the context of this invention, the term "unknown bioagent" may mean either: (i) a bioagent whose existence is known (such as the well known bacterial species *Staphylococcus aureus* for example) but which is not known to be in a sample to be analyzed, or (ii) a bioagent whose existence is not known (for example, the SARS coronavirus was unknown prior to April 2003). For example, if the method for identification of coronaviruses disclosed in commonly owned U.S. Ser. No. 10/829,826 (incorporated herein by reference in entirety) was to be employed prior to April 2003 to identify the SARS coronavirus in a clinical sample, both meanings of "unknown" bioagent are applicable since the SARS coronavirus was unknown to science prior to April, 2003 and since it was not known what bioagent (in this case a coronavirus) was present in the sample. On the other hand, if the method of U.S. Ser. No. 10/829,826 was to be employed subsequent to April 2003 to identify the SARS coronavirus in a clinical sample, only the first meaning (i) of "unknown" bioagent would apply since the SARS coronavirus became known to science subsequent to April 2003 and since it was not known what bioagent was present in the sample.

In those embodiments wherein the bioagent is an RNA virus, the RNA of the virus is reverse transcribed to obtain corresponding DNA which can be subsequently amplified by procedures referred to above. In one embodiment, one means of reverse transcription is reverse transcriptase, an enzyme well known in the molecular biology arts.

The employment of more than one bioagent identifying amplicon for identification of a bioagent is herein referred to as "triangulation identification." Triangulation identification is pursued by analyzing a plurality of bioagent identifying amplicons selected within multiple core genes. This process can be used to reduce false negative and false positive signals, and enable reconstruction of the origin of hybrid or otherwise engineered bioagents. For example, identification of the three part toxin genes typical of *B. anthracis* (Bowen et al., J. Appl. Microbiol., 1999, 87, 270-278) in the absence of the expected signatures from the *B. anthracis* genome would suggest a genetic engineering event.

In some embodiments, the triangulation identification process can be pursued by characterization of bioagent identifying amplicons in a massively parallel fashion using the polymerase chain reaction (PCR), such as multiplex PCR where multiple primers are employed in the same amplification reaction mixture, or PCR in multi-well plate format wherein a different and unique pair of primers is used in multiple wells containing otherwise identical reaction mixtures. Such multiplex and multi-well PCR methods are well known to those with ordinary skill in the arts of rapid throughput amplification of nucleic acids.

In some embodiments, the molecular mass of a given bioagent identifying amplicon is determined by mass spectrometry. Mass spectrometry has several advantages, not the least of which is high bandwidth characterized by the ability to separate (and isolate) many molecular peaks across a broad range of mass to charge ratio (m/z). Thus mass spectrometry is intrinsically a parallel detection scheme without the need for radioactive or fluorescent labels, since every amplification product is identified by its molecular mass. The current state of the art in mass spectrometry is such that less than femtomole quantities of material can be readily analyzed to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons.

In some embodiments, intact molecular ions are generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). Upon ionization, several peaks are observed from one sample due to the formation of ions with different charges. Averaging the multiple readings of molecular mass obtained from a single mass spectrum affords an estimate of molecular mass of the bioagent identifying amplicon. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used in the methods of the present invention include, but are not limited to, Fourier transform ion cyclotron resonance mass spectrometry (FT-ICR-MS), ion trap, quadrupole, magnetic sector, time of flight (TOF), Q-TOF, and triple quadrupole.

In some embodiments, conversion of molecular mass data to a base composition is useful for certain analyses. As used herein, a "base composition" is the exact number of each nucleobase (A, T, C and G). For example, amplification of nucleic acid of *Neisseria meningitidis* with a primer pair that produces an amplification product from nucleic acid of 23S rRNA that has a molecular mass (sense strand) of 28480.75124, from which a base composition of A25 G27 C22 T18 is assigned from a list of possible base compositions calculated from the molecular mass using standard known molecular masses of each of the four nucleobases.

In some embodiments, assignment of base compositions to experimentally determined molecular masses is accomplished using "base composition probability clouds." Base compositions, like sequences, vary slightly from isolate to isolate within species. It is possible to manage this diversity by building "base composition probability clouds" around the composition constraints for each species. This permits identification of organisms in a fashion similar to sequence analysis. Optimal primer design requires optimal choice of bioagent identifying amplicons and maximizes the separation between the base composition signatures of individual bioagents. Areas where clouds overlap indicate regions that may result in a misclassification, a problem which is overcome by a triangulation identification process using bioagent identifying amplicons not affected by overlap of base composition probability clouds.

In some embodiments, base composition probability clouds provide the means for screening potential primer pairs in order to avoid potential misclassifications of base compositions. In other embodiments, base composition probability clouds provide the means for predicting the identity of a bioagent whose assigned base composition was not previously observed and/or indexed in a bioagent identifying amplicon base composition database due to evolutionary transitions in its nucleic acid sequence. Thus, in contrast to probe-based techniques, mass spectrometry determination of base composition does not require prior knowledge of the composition or sequence in order to make the measurement.

The present invention provides bioagent classifying information similar to DNA sequencing and phylogenetic analysis at a level sufficient to detect and identify a given bioagent. Furthermore, the process of determination of a previously unknown base composition for a given bioagent (for example, in a case where sequence information is unavailable) has downstream utility by providing additional bioagent indexing information with which to populate base composition databases. The process of future bioagent identification is thus greatly improved as more BCS indexes become available in base composition databases.

The present invention also provides kits for carrying out the methods described herein. In some embodiments, the kit may comprise a sufficient quantity of one or more primer pairs to perform an amplification reaction on a target polynucleotide from a bioagent to form a bioagent identifying amplicon. In some embodiments, the kit may comprise from one to fifty primer pairs, from one to twenty primer pairs, from one to ten primer pairs, or from two to five primer pairs. In some embodiments, the kit may comprise one or more primer pairs recited in Table 1.

In some embodiments, the kit may comprise broad range survey primers, division wide primers, clade group primers or drill-down primers, or any combination thereof. A kit may be designed so as to comprise particular primer pairs for identification of a particular bioagent. For example, a broad range survey primer kit may be used initially to identify an unknown bioagent as a member of the *Bacillus/Clostridia* group. Another example of a division-wide kit may be used to distinguish *Bacillus anthracis, Bacillus cereus* and *Bacillus thuringiensis* from each other. A drill-down kit may be used, for example, to identify genetically engineered *Bacillus anthracis*. In some embodiments, any of these kits may be combined to comprise a combination of broad range survey primers and division-wide primers so as to be able to identify the species of an unknown bioagent.

In some embodiments, the kit may contain standardized nucleic acids for use as internal amplification calibrants.

In some embodiments, the kit may also comprise a sufficient quantity of reverse transcriptase (if an RNA virus is to be identified for example), a DNA polymerase, suitable nucleoside triphosphates (including any of those described above), a DNA ligase, and/or reaction buffer, or any combination thereof, for the amplification processes described above. A kit may further include instructions pertinent for the particular embodiment of the kit, such instructions describing the primer pairs and amplification conditions for operation of the method. A kit may also comprise amplification reaction containers such as microcentrifuge tubes and the like. A kit may also comprise reagents or other materials for isolating bioagent nucleic acid or bioagent identifying amplicons from amplification, including, for example, detergents, solvents, or ion exchange resins which may be linked to magnetic beads. A kit may also comprise a table of measured or calculated molecular masses and/or base compositions of bioagents using the primer pairs of the kit.

While the present invention has been described with specificity in accordance with certain of its embodiments, the following examples serve only to illustrate the invention and are not intended to limit the same. Throughout these examples, molecular cloning reactions, and other standard recombinant DNA techniques, may be carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1

Design of Calibrant Polynucleotides Based on Viral Bioagent Identifying Amplicons from the SARS Coronavirus (Viral Bioagent Identifying Amplicons)

This example describes the design of two coronavirus calibrant polynucleotides based on viral bioagent identifying amplicons for identification of coronaviruses (viral bioagent identifying amplicons) in the RNA-dependent RNA polymerase (RdRp) gene and in the nsp11 gene which are described in a method for identification of coronaviruses disclosed in U.S. application Ser. No. 10/829,826. The primers used to define the viral bioagent identifying amplicons hybridize to regions of the RdRp gene (primer pair no. 453: forward—TAAGU$^a$U$^a$TU$^a$ATGGCGGCU$^a$GG (SEQ ID NO: 1) and reverse—TTTAGGATAGTC$^a$C$^a$C$^a$ AAC-CCAT (SEQ ID NO: 2)) and the nsp11 gene (primer pair no. 455: forward—TGTTTG U$^a$U$^a$U$^a$U$^a$GGAATTGTAATGT-TGA (SEQ ID NO: 3) and reverse—TGGAATGCATGCU$^a$U$^a$AU$^a$U$^a$AACATACA (SEQ ID NO: 4)), wherein U$^a$ represents=5-propynyluracil and C$^a$ represents 5-propynylcytosine). The calibration sequence chosen to simulate the RdRp calibration amplicon is SEQ ID NO: 5 which corresponds to positions 15146 to 15233 of NC_004718.3 (SARS coronavirus TOR2 genome) with deletion of positions 15179-15183 to yield a calibration amplicon length of 83 bp. The calibration sequence for the nsp11 calibration amplicon is SEQ ID NO: 6, which corresponds to positions 19113 to 19249 of NC_004718.3 (SARS coronavirus TOR2 genome) with deletion of positions 19172-19176 to yield a calibration amplicon of 132 bp length. Both calibrant standard sequences (SEQ ID NOs: 5 and 6) were included on a single polynucleotide (SEQ ID NO: 7—herein designated a "combination calibration polynucleotide") which was cloned into a pCR®-Blunt vector (Invitrogen, Carlsbad, Calif.). Thus, when the combination calibration polynucleotide is added to an amplification reaction, an RdRp-based calibration amplicon will be produced in an amplification reaction with primer pair 453 (SEQ ID NOs: 1:2) and an nsp11-based calibration amplicon will be produced with primer pair 455 (SEQ ID NOs: 3:4).

The viral bioagent identifying amplicons are used as identifiers of coronaviruses due to the variable regions between the conserved priming regions which can be distinguished by mass spectrometry. The calibration polynucleotides are used to produce calibration amplicons from which the quantity of identified coronavirus is determined.

Example 2

Use of a Calibration Polynucleotide for Determining the Quantity of Coronavirus in a Clinical Sample To determine the quantity of SARS coronavirus in a clinical sample, viable SARS coronavirus was added to human serum and analyzed. The TOR2 isolate of the SARS coronavirus from three passages in Vero cells was titered by plaque assay. Virus was handled in a P3 facility by investigators wearing forced air respirators. Equipment and supplies were decontaminated with 10% hypochlorite bleach solution for a minimum of 30 minutes or by immersion in 10% formalin for a minimum of 12 hours and virus was handled in strict accordance with specific Scripps Research Institute policy. SARS coronavirus was cultured in sub confluent Vero-E6 cells at 37° C., 5% $CO_2$ in complete DMEM with final concentrations of 10% fetal bovine serum (Hyclone, Salt Lake City, Utah), 292 µg/mL L-Glutamine, 100 U/mL penicillin G sodium, 100 µg/mL streptomycin sulfate (Invitrogen, Carlsbad Calif.), and 10 mM HEPES (Invitrogen, Carlsbad Calif.). Virus-containing medium was collected during the peak of viral cytopathic effects, 48 h after inoculation with approximately 10 PFU/cell of SARS coronavirus from the second passage of stock virus. Infectious virus was titered by plaque assay. Monolayers of Vero-E6 cells were prepared at 70-80% confluence in tissue culture plates. Serial tenfold dilutions of virus were prepared in complete DMEM. Medium was aspirated from cells, replaced by 200 µL of inoculum, and cells were incubated at 37° C., 5% $CO_2$ for 1 hour. Cells were overlaid with 2-3 mL/well of 0.7% agarose, 1x DMEM overlay containing 2% fetal bovine serum. Agarose was allowed to solidify at room temperature then cells were incubated at 37° C., 5% $CO_2$ for 72 h. Plates were decontaminated by overnight formalin immersion, agarose plugs were removed, and cells were stained with 0.1% crystal violet to highlight viral plaques.

RNA was isolated from serum containing two different concentrations of the virus ($1.7 \times 10^5$ and 170 PFU/mL) and reverse transcribed to cDNA using random primers and reverse transcriptase. A PFU (plate forming unit) is a quantitative measure of the number of infectious virus particles in a given sample, since each infectious virus particle can give rise to a single clear plaque on infection of a continuous "lawn" of bacteria or a continuous sheet of cultured cells. PCR amplifications were performed using both the RdRp and the nsp11 primer sets on serial ten-fold dilutions of these cDNAs. Amplification products were purified and analyzed by methods commonly owned and disclosed in U.S. application Ser. Nos. 10/829,826 and 10/844,938, each of which is incorporated herein by reference in its entirety. The limit of SARS coronavirus detection was 10-2 PFU per PCR reaction (~1.7 PFU/mL serum). Since PFU reflects the number of infectious viral particles and not the total number of RNA genomes, the number of reverse-transcribed SARS genomes was estimated by competitive, quantitative PCR using a calibration polynucleotide. Analysis of ratios of mass spectral peak heights of titrations of the calibration polynucleotide and the SARS cDNA showed that approximately 300 reverse-transcribed viral genomes were present per PFU, similar to the ratio of viral genome copies per PFU reported for RNA viruses (J. S. Towner et al., J Virol In Press (2004)). Using this estimate, the PCR primers were sensitive to three genomes per PCR reaction, consistent with previously reported detection limits for optimized SARS-specific primers (Drosten et al., *New England Journal of Medicine*, 2003, 348, 1967). When RT-PCR products were measured for varying dilutions of the SARS virus spiked directly into serum, 1 PFU (~300 genomes) per PCR reaction or 170 PFU ($5.1 \times 10^4$ genomes) per mL serum could be reliably detected.

The discrepancy between the detection sensitivities in the two experimental protocols described above suggests that there were losses associated with RNA extraction and reverse transcription when very little virus was present (<300 copies) in the starting sample in serum.

To determine the relationship between PFU and copies of nucleic acid target, the virus stock was analyzed using the methods of the present invention. Synthetic DNA templates with nucleic acid sequence identical in all respects to RdRp-based (SEQ ID NO: 5) and nsp11-based (SEQ ID NO: 6) viral bioagent identifying amplicons for the SARS coronavirus with the exception of 5 base deletions internal to each amplicon were combined into a single combination calibration polynucleotide (SEQ ID NO: 7) and cloned into a pCR®-Blunt vector (Invitrogen, Carlsbad, Calif.) to produce a calibration polynucleotide. The calibrant plasmid stock solutions were quantified using $OD_{260}$ measurements, serially diluted (10-fold dilutions), and mixed with a fixed amount of post-reverse transcriptase cDNA preparation of the virus stock and analyzed by competitive PCR and electrospray mass spectrometry. Each PCR reaction produced two sets of amplicons, one corresponding to the calibrant amplicon and the other to the viral bioagent identifying amplicon. Since the primers hybridize to both the calibration polynucleotide and the coronavirus cDNA, it was reasonably assumed that the calibration polynucleotide and coronavirus cDNA would have similar PCR efficiencies for amplification of the two products. Analysis of the ratios of peak heights (abundance data) of the resultant mass spectra of the calibration amplicons DNA and viral bioagent identifying amplicons used to determine the amounts of nucleic acid copies (as measured by calibrant molecules) present per PFU. Since all of the extracted RNA was used in the reverse transcriptase step to produce the viral cDNA, the approximate amount of nucleic acids associated with infectious virus particles in the original viral preparation could be estimated. Mass spectrometry analysis showed an approximate 1:1 peak abundance between the calibrant peak at the $3\times10^4$ copy number dilution and the viral bioagent identifying amplicon peak for the RdRp primer set (FIG. 2). Thus, the relationship between PFU and copies of nucleic acid was calculated to be 1 PFU=300 copies of nucleic acid.

The calibration sequences described in this example are appropriate for use in production of calibration amplicons which are in turn useful for determining the quantity of all known members of the coronavirus family. Further, it is reasonably expected that these calibration sequences will likewise be appropriate for quantification of any coronaviruses that are yet to be discovered.

Example 3

Design of Calibrant Polynucleotides Based on Bioagent Identifying Amplicons for Identification of Species of Bacteria (Bacterial Bioagent Identifying Amplicons)

This example describes the design of 19 calibrant polynucleotides based on broad range bacterial bioagent identifying amplicons. The bacterial bioagent identifying amplicons are obtained upon amplification of bacterial nucleic acid with primers (Table 1) that have been disclosed in U.S. patent application Ser. Nos. 10/660,122, 10,728,486, and 60/559,754, each of which is commonly owned and incorporated herein by reference in its entirety.

Calibration sequences were designed to simulate bacterial bioagent identifying amplicons produced by the primer pairs shown in Table 1. The calibration sequences were chosen as a representative member of the section of bacterial genome from specific bacterial species which would be amplified by a given primer pair. The model bacterial species upon which the calibration sequences are based are also shown in Table 1. For example, the calibration sequence chosen to correspond to an amplicon produced by primer pair no. 346 is SEQ ID NO: 8. In Table 1, the forward (_F) or reverse (_R) primer name indicates the coordinates of an extraction representing a gene of a standard reference bacterial genome to which the primer hybridizes e.g.: the forward primer name 16S_EC_713_732TMOD_F indicates that the forward primer hybridizes to residues 712-732 of the gene encoding 16S ribosomal RNA in an *E. coli* reference sequence (in this case, the reference sequence (SEQ ID NO: 66 in Table 2) is an extraction consisting of residues 4033120-4034661 of the genomic sequence of *E. coli* K12 (GenBank Accession No. NC_000913)—See Table 2. Additional gene coordinate reference information is shown in Table 2. The designation "TMOD" in the primer names indicates that the 5' end of the primer has been modified with a non-matched template T residue. This modification prevents the PCR polymerase from adding non-templated adenosine residues to the 5' end of the amplification product, an occurrence which may result in miscalculation of base composition from molecular mass data.

The 19 calibration sequences shown in Table 1 were combined into a single calibration polynucleotide sequence (SEQ ID NO: 9—which is herein designated a "combination calibration polynucleotide") which was then cloned into a pCR®-Blunt vector (Invitrogen, Carlsbad, Calif.). This combination calibration polynucleotide can be used in conjunction with the primers of Table 1 as an internal standard to produce calibration amplicons for use in determination of the quantity of any bacterial bioagent. Thus, for example, when the combination calibration polynucleotide vector is present in an amplification reaction mixture, a calibration amplicon based on primer pair 346 (16S rRNA) will be produced in an amplification reaction with primer pair 346 and a calibration amplicon based on primer pair 363 (rpoC) will be produced with primer pair 363.

TABLE 1

Bacterial Primer Pairs for Production of Bacterial Bioagent Identifying Amplicons and Corresponding Representative Calibration Sequences

| Primer Pair No. | Forward Primer Name | Forward Primer (SEQ ID NO:) | Reverse Primer Name | Reverse Primer (SEQ ID NO:) | Calibration Sequence Model Species | Calibration Sequence (SEQ ID NO:) |
|---|---|---|---|---|---|---|
| 346 | 16S_EC_713_732_TMOD_F | 10 | 16S_EC_789_809_TMOD_R | 11 | *Bacillus anthracis* | 8 |
| 347 | 16S_EC_785_806_TMOD_F | 12 | 16S_EC_880_897_TMOD_R | 13 | *Bacillus anthracis* | 14 |

TABLE 1-continued Bacterial Primer Pairs for Production of Bacterial Bioagent Identifying Amplicons and Corresponding Representative Calibration Sequences

| Primer Pair No. | Forward Primer Name | Forward Primer (SEQ ID NO:) | Reverse Primer Name | Reverse Primer (SEQ ID NO:) | Calibration Sequence Model Species | Calibration Sequence (SEQ ID NO:) |
|---|---|---|---|---|---|---|
| 348 | 16S_EC_960_981_TMOD_F | 15 | 16S_EC_1054_1073_TMOD_R | 16 | *Bacillus anthracis* | 17 |
| 349 | 23S_EC_1826_1843_TMOD_F | 18 | 23S_EC_1906_1924_TMOD_R | 19 | *Bacillus anthracis* | 20 |
| 350 | CAPC_BA_274_303_TMOD_F | 21 | CAPC_BA_349_376_TMOD_R | 22 | *Bacillus anthracis* | 23 |
| 351 | CYA_BA_1353_1379_TMOD_F | 24 | CYA_BA_1448_1467_TMOD_R | 25 | *Bacillus anthracis* | 26 |
| 352 | INFB_EC_1365_1393_TMOD_F | 27 | INFB_EC_1439_1467_TMOD_R | 28 | *Bacillus anthracis* | 29 |
| 353 | LEF_BA_756_781_TMOD_F | 30 | LEF_BA_843_872_TMOD_R | 31 | *Bacillus anthracis* | 32 |
| 354 | RPOC_EC_2218_2241_TMOD_F | 33 | RPOC_EC_2313_2337_TMOD_R | 34 | *Bacillus anthracis* | 35 |
| 355 | SSPE_BA_115_137_TMOD_F | 36 | SSPE_BA_197_222_TMOD_R | 37 | *Bacillus anthracis* | 38 |
| 356 | RPLB_EC_650_679_TMOD_F | 39 | RPLB_EC_739_762_TMOD_R | 40 | *Clostridium botulinum* | 41 |
| 358 | VALS_EC_1105_1124_TMOD_F | 42 | VALS_EC_1195_1218_TMOD_R | 43 | *Yersinia Pestis* | 44 |
| 359 | RPOB_EC_1845_1866_TMOD_F | 45 | RPOB_EC_1909_1929_TMOD_R | 46 | *Yersinia Pestis* | 47 |
| 360 | 23S_EC_2646_2667_TMOD_F | 48 | 23S_EC_2745_2765_TMOD_R | 49 | *Bacillus anthracis* | 50 |
| 361 | 16S_EC_1090_1111_2_TMOD_F | 51 | 16S_EC_1175_1196_TMOD_R | 52 | *Bacillus anthracis* | 53 |
| 362 | RPOB_EC_3799_3821_TMOD_F | 54 | RPOB_EC_3862_3888_TMOD_R | 55 | *Burkholderia mallei* | 56 |
| 363 | RPOC_EC_2146_2174_TMOD_F | 57 | RPOC_EC_2227_2245_TMOD_R | 58 | *Burkholderia mallei* | 59 |
| 367 | TUFB_EC_957_979_TMOD_F | 60 | TUFB_EC_1034_1058_TMOD_R | 61 | *Burkholderia mallei* | 62 |
| 449 | RPLB_EC_690_710_F | 63 | RPLB_EC_737_758_R | 64 | *Clostridium botulinum* | 65 |

TABLE 2

Primer Pair Gene Coordinate References and Calibration Polynucleotide Sequence Coordinates within the Combination Calibration Polynucleotide

| Bacterial Gene | Primer Pair No. | Gene Extraction SEQ ID NO: | Gene Extraction Coordinates of Genomic or Plasmid Sequence | GenBank Accession No. of Genomic (G) or Plasmid (P) Sequence | Coordinates of Calibration Sequence in Combination Calibration Polynucleotide (SEQ ID. NO: 9) |
|---|---|---|---|---|---|
| 16S *E. coli* | 346 | 66 | 4033120 . . . 4034661 | NC_000913 (G) | 16 . . . 109 |
| 16S *E. coli* | 347 | 66 | 4033120 . . . 4034661 | NC_000913 (G) | 83 . . . 190 |
| 16S *E. coli* | 348 | 66 | 4033120 . . . 4034661 | NC_000913 (G) | 246 . . . 353 |
| 16S *E. coli* | 361 | 66 | 4033120 . . . 4034661 | NC_000913 (G) | 368 . . . 469 |
| 23S *E. coli* | 349 | 67 | 4166220 . . . 4169123 | NC_000913 (G) | 743 . . . 837 |
| 23S *E. coli* | 360 | 67 | 4166220 . . . 4169123 | NC_000913 (G) | 865 . . . 981 |
| rpoB *E. coli.* | 359 | 68 | 4178823 . . . 4182851 (complement strand) | NC_000913 (G) | 1591 . . . 1672 |
| rpoB *E. coli* | 362 | 68 | 4178823 . . . 4182651 (complement strand) | NC_000913 (G) | 2081 . . . 2167 |
| rpoC *E. coli* | 354 | 69 | 4182928 . . . 4187151 | NC_000913 (G) | 1810 . . . 1926 |
| rpoC *E. coli* | 363 | 69 | 4182928 . . . 4187151 | NC_000913 (G) | 2183 . . . 2279 |
| infB *E. coli* | 352 | 70 | 3313655 . . . 3310983 (complement strand) | NC_000913 (G) | 1692 . . . 1791 |
| tufB *E. coli* | 367 | 71 | 4173523 . . . 4174707 | NC_000913 (G) | 2400 . . . 2498 |
| rplB *E. coli* | 356 | 72 | 3449001 . . . 3448180 | NC_000913 (G) | 1945 . . . 2060 |
| rplB *E. coli* | 449 | 72 | 3449001 . . . 3448180 | NC_000913 (G) | 1986 . . . 2055 |
| valS *E. coli* | 358 | 73 | 4481405 . . . 4478550 (complement strand) | NC_000913 (G) | 1462 . . . 1572 |
| capC *B. anthracis* | 350 | 74 | 56074 . . . 55628 (complement strand) | AF188935 (P) | 2517 . . . 2616 |

TABLE 2-continued

Primer Pair Gene Coordinate References and Calibration Polynucleotide
Sequence Coordinates within the Combination Calibration Polynucleotide

| Bacterial Gene | Primer Pair No. | Gene Extraction SEQ ID NO: | Gene Extraction Coordinates of Genomic or Plasmid Sequence | GenBank Accession No. of Genomic (G) or Plasmid (P) Sequence | Coordinates of Calibration Sequence in Combination Calibration Polynucleotide (SEQ ID. NO: 9) |
|---|---|---|---|---|---|
| Cya B. anthracis | 351 | 75 | 156626 . . . 154288 (complement strand) | AF065404 (P) | 1338 . . . 1449 |
| Lef B. anchracis | 353 | 76 | 127442 . . . 129921 | AF065404 (P) | 1121 . . . 1234 |
| sspE B. anthracis | 355 | 77 | 226496 . . . 226783 | AE017025 (G) | 1007-1104 |

Example 4

Figure 3:
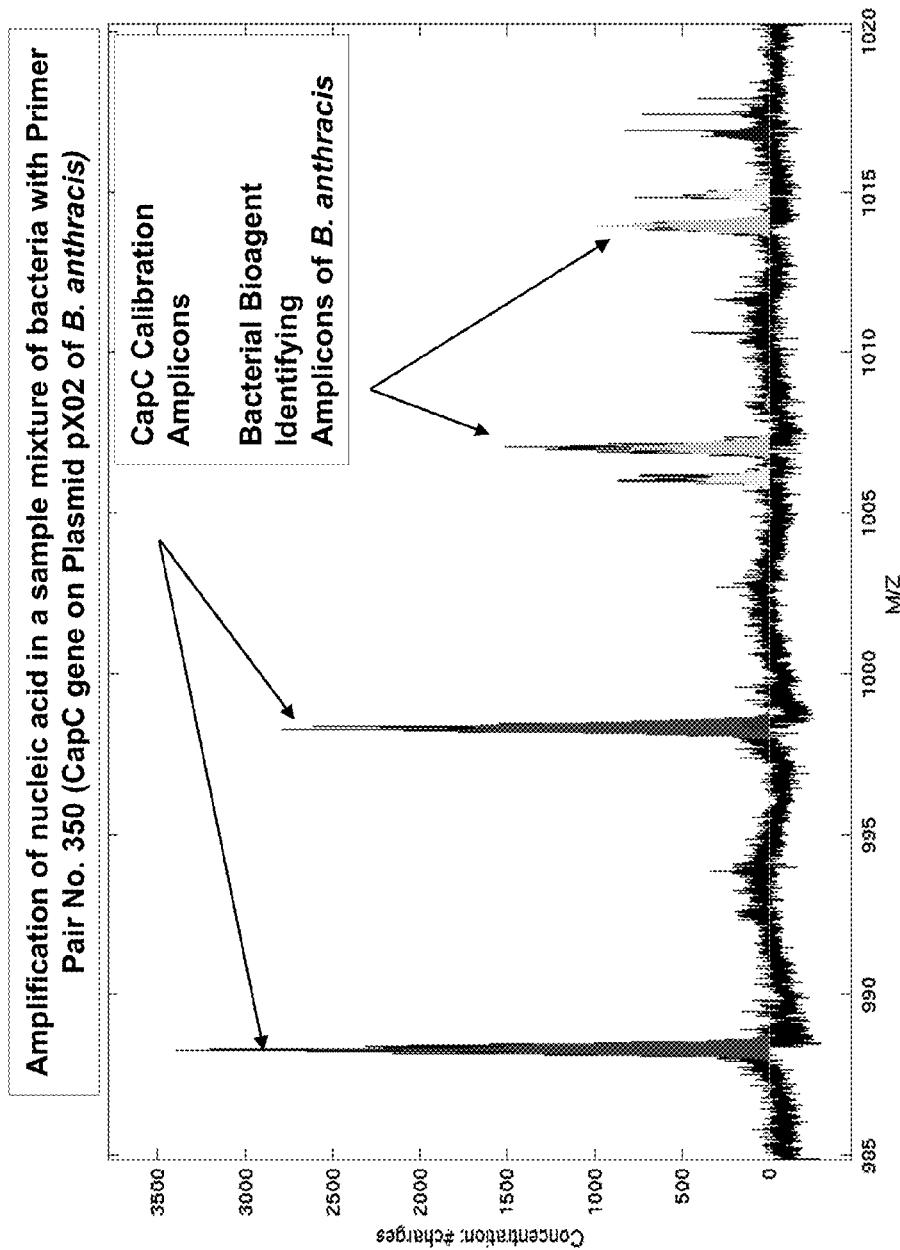
FIG. 3 shows a representative mass spectrum of an amplified nucleic acid mixture containing the Ames strain of *Bacillus anthracis*, a known quantity of combination calibration polynucleotide v an unknown bioagent are added primers (100) and a known quantity of a calibration polynucleotide (105). The total nucleic acid in the sample is then subjected to an amplification reaction (110) to obtain amplification products. The molecular masses of amplification products are determined (115) from which are obtained molecular mass and abundance data. The molecular mass of the bioagent identifying amplicon (120) provides the means for its identification (125) and the molecular mass of the calibration amplicon obtained from the calibration polynucleotide (130) provides the means for its identification (135). The abundance data of the bioagent identifying amplicon is recorded (140) and the abundance data for the calibration data is recorded (145), both of which are used in a calculation (150) which determines the quantity of unknown bioagent in the sample. Each of these features is described below in greater detail.

Use of a Calibration Polynucleotide for Determining the Quantity of Bacillus Anthracis in a Sample Containing a Mixture of Microbes The capC gene is a gene involved in capsule synthesis which resides on the pX02 plasmid of *Bacillus anthracis*. Primer pair no. 350 (see Tables 1 and 2) was designed to identify *Bacillus anthracis* via production of a bacterial bioagent identifying amplicon. Known quantities of the combination calibration polynucleotide vector described in Example 3 were added to amplification mixtures containing bacterial bioagent nucleic acid from a mixture of microbes which included the Ames strain of *Bacillus anthracis*. Upon amplification of the bacterial bioagent nucleic acid and the combination calibration polynucleotide vector with primer pair no. 350, bacterial bioagent identifying amplicons and calibration amplicons were obtained and characterized by mass spectrometry. A spectrum of an amplified nucleic acid mixture containing the Ames strain of *Bacillus anthracis*, a known quantity of combination calibration polynucleotide vector which includes the CapC calibration sequence for *Bacillus anthracis* and primer pair 350 is shown in FIG. 3. The molecular masses of the bioagent identifying amplicons provided the means for identification of the bioagent from which they were obtained (Ames strain of *Bacillus anthracis*) and the molecular masses of the calibration amplicons provided the means for their identification as well. The relationship between the abundance (peak height) of the calibration amplicon signals and the bacterial bioagent identifying amplicon signals provides the means of calculation of the copies of the pX02 plasmid of the Ames strain of *Bacillus anthracis*. Methods of calculating quantities of molecules based on internal calibration procedures are well known to those of ordinary skill in the art.

Calibration amplicons and bacterial bioagent identifying amplicons produced in the reaction are visible in the mass spectrum as indicated and abundance (peak height) data are used to calculate the quantity of the pX02 plasmid of the Ames strain of *Bacillus anthracis* in the sample. Averaging the results of 10 repetitions of the experiment described above, enabled a calculation that indicated that the quantity of Ames strain of *Bacillus anthracis* present in the sample corresponds to approximately 10 copies of pX02 plasmid.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A system, comprising:
   a) a nucleic acid amplification component, comprising a pair of primers designed to produce a bioagent identifying amplicon from a bioagent nucleic acid sequence acid under amplification conditions, a known quantity of a calibration polynucleotide comprising a calibration sequence designed to produce a calibration amplicon as a result of amplification with said primers under said amplification conditions wherein the 5' and 3' ends of said amplicons are the sequences of said pair of primers or complements thereof, and an amplification reaction vessel wherein said bioagent identifying amplicon and said calibration amplicon are concurrently amplified;
   b) a molecular mass determination component; and
   c) a molecular mass identification component comprising at least one computer comprising a processor and software, and a database of molecular masses of bioagent identifying amplicons from a plurality known bioagents wherein a match between the molecular mass of said bioagent identifying amplicon and the molecular mass of a bioagent identifying amplicon from a known bioagent in said database of molecular masses identifies said bioagent, a molecular mass of said calibration amplicon identifies said calibration amplicon, and molecular mass abundance data of said bioagent identifying ampicon and molecular mass abundance data of said calibration amplicon indicates the quantity of said bioagent.

2. The system of claim 1, wherein said calibration sequence: a) comprises a chosen standard sequence of a bioagent identifying amplicon with the exception of a deletion of about 2 to about 8 consecutive nucleotide residues of said standard sequence; b) comprises a chosen standard sequence of a bioagent identifying amplicon with the exception of an insertion of about 2 to about 8 consecutive nucleotide residues of said standard sequence; or c) has at least 80% sequence identity with a chosen standard sequence of a bioagent identifying amplicon.

3. The system of claim 1, wherein said molecular mass determination component comprises a mass spectrometer.

4. The system of claim 1, wherein said molecular mass abundance data of said calibration amplicon comprises a standard curve wherein the amount of said calibration polynucleotide in said amplification reaction vessel is varied.

5. The system of claim 1, wherein said nucleic acid amplification component comprises a plurality of primer pairs which amplify a corresponding plurality of bioagent nucleic acid sequences and calibration sequences.

6. The system of claim 5, wherein said plurality of primer pairs comprise survey primers, division-wide primers, clade group primers and sub-species characteristic primers.

7. The system of claim 5, wherein said plurality of primer pairs comprise a plurality of bioagent identifying primer pairs within a plurality of core gene primer pairs.

8. The system of claim 7, wherein said core gene primer pairs hybridize to conserved regions of nucleic acid of genes encoding 16S and 23S rRNAs, RNA polymerase subunits, t-RNA synthetases, elongation factors, ribosomal proteins, protein chain initiation factors, cell division proteins, chaperonin groEL, chaperonin dnaK, phosphoglycerate kinase, NADH dehydrogenase, DNA ligases, and DNA topoisomerases.

9. The system of claim 1, further comprising a nucleic acid purification component.

10. The system of claim 9, wherein said nucleic acid purification component comprises one or more buffer manipulations, one or more salt manipulations, one or more thermal manipulations, one or more pH manipulations, one or more mechanical manipulations, one or more centrifugation manipulations, or one or more magnetic manipulations.

11. The system of claim 1, wherein said nucleic acid amplification component comprises a thermocycler.

12. The system of claim 1, wherein said nucleic acid amplification component comprises one or more salts, one or more buffers, one or more purified oligonucleotide primers, one or more dNTPs, or one or more enzymes.

13. The system of claim 1, further comprising a computer program on a computer readable medium configured to direct said processor to coordinate the operation of said nucleic acid amplification component, said molecular mass determination component, and said molecular mass identification component.

14. A system, comprising:
   a) a nucleic acid amplification component, comprising a pair of primers designed to produce a bioagent identifying amplicon from a bioagent nucleic acid sequence acid under amplification conditions, a known quantity of a calibration polynucleotide comprising a calibration sequence designed to produce a calibration amplicon as a result of amplification with said primers under said amplification conditions wherein the 5' and 3' ends of said amplicons are the sequences of said pair of primers or complements thereof, and an amplification reaction vessel wherein said bioagent identifying amplicon and said calibration amplicon are concurrently amplified;
   b) a base composition determination component comprising a component that measures the molecular masses of said bioagent identifying amplicon and said calibration amplicon, and a computer comprising a processor and software that calculates the base compositions of said molecular masses; and
   c) a base composition identification component comprising at least one computer comprising a processor and software, and a database of base compositions of bioagent identifying amplions from a plurality of known bioagents wherein a match between the base composition of said bioagent identifying amplicon and the base composition of a bioagent identifying amplicon from a known bioagent in said database of base compositions identifies said bioagent, a base composition of said calibration amplicon identifies said calibration amplicon, and molecular mass abundance data of said bioagent identifying ampicon and molecular mass abundance data of said calibration amplicon indicates the quantity of said bioagent.

15. The system of claim 14, wherein said calibration sequence: a) comprises a chosen standard sequence of a bioagent identifying amplicon with the exception of a deletion of about 2 to about 8 consecutive nucleotide residues of said standard sequence; b) comprises a chosen standard sequence of a bioagent identifying amplicon with the exception of an insertion of about 2 to about 8 consecutive nucleotide residues of said standard sequence; or c) has at least 80% sequence identity with a chosen standard sequence of a bioagent identifying amplicon.

16. The system of claim 14, wherein said molecular mass determination component comprises a mass spectrometer.

17. The system of claim 14, wherein said molecular mass abundance data of said calibration amplicon comprises a standard curve wherein the amount of said calibration polynucleotide in said amplification reaction vessel is varied.

18. The system of claim 14, wherein said nucleic acid amplification component comprises a plurality of primer pairs which amplify a corresponding plurality of bioagent nucleic acid sequences and calibration sequences.

19. The system of claim 14, wherein said plurality of primer pairs comprise survey primers, division-wide primers, clade group primers and sub-species characteristic primers.

20. The system of claim 14, wherein said plurality of primer pairs comprise a plurality of bioagent identifying primer pairs within a plurality of core gene primer pairs.

* * * * *